(12) United States Patent
Hammons et al.

(10) Patent No.: US 11,839,531 B2
(45) Date of Patent: *Dec. 12, 2023

(54) NONWOVEN WEBS WITH HYDROPHOBIC AND HYDROPHILIC LAYERS

(71) Applicant: The Procter & Gamble Company, Cincinnati, OH (US)

(72) Inventors: John Lee Hammons, Hamilton, OH (US); Kelyn Anne Arora, Cincinnati, OH (US); Dean Larry DuVal, Lebanon, OH (US); Stephanie Michelle Niezgoda, Cincinnati, OH (US); Rajeev Chhabra, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/398,305

(22) Filed: Aug. 10, 2021

(65) Prior Publication Data

US 2021/0369508 A1 Dec. 2, 2021

Related U.S. Application Data

(63) Continuation of application No. 16/716,905, filed on Dec. 17, 2019, now Pat. No. 11,110,013, which is a
(Continued)

(51) Int. Cl.
*B32B 5/02* (2006.01)
*B32B 5/26* (2006.01)
(Continued)

(52) U.S. Cl.
CPC ........ *A61F 13/5116* (2013.01); *A61F 13/512* (2013.01); *A61F 13/5123* (2013.01);
(Continued)

(58) Field of Classification Search
None
See application file for complete search history.

(56) References Cited

U.S. PATENT DOCUMENTS

| 3,093,612 A | 6/1963 | Cox, Jr. |
| 3,139,412 A | 6/1964 | Sterling |
| (Continued) | | |

FOREIGN PATENT DOCUMENTS

| CN | 1722999 A | 1/2006 |
| CN | 1728979 A | 2/2006 |
| (Continued) | | |

OTHER PUBLICATIONS

Machine Translation of JP-02109561-A, Apr. 1990 (Year: 1990).*
(Continued)

*Primary Examiner* — Jeffrey A Vonch
(74) *Attorney, Agent, or Firm* — Sarah M. DeCristofaro; Melissa G. Krasovec; George Henry Leal

(57) ABSTRACT

A nonwoven web for use in an absorbent article is described. The nonwoven web has first and second nonwoven layers. The first nonwoven layer has a first plurality of fibers, an additive disposed, at least in part, on a portion of the first plurality of fibers, a first side and an opposing second side, wherein second side has a plurality of discontinuities. The second nonwoven layer has a second plurality of fibers, a first surface and an opposing second surface, and a plurality of tufts extending through at least a portion of the discontinuities in the first nonwoven layer, wherein the second nonwoven layer is attached to the first nonwoven layer such that at least a portion of the second plurality of fibers are in liquid communication with the first nonwoven layer, wherein the first nonwoven layer is hydrophobic and the second nonwoven layer is hydrophilic.

10 Claims, 27 Drawing Sheets

Related U.S. Application Data continuation of application No. 14/849,630, filed on Sep. 10, 2015, now abandoned.

(60) Provisional application No. 62/048,316, filed on Sep. 10, 2014.

(51) Int. Cl.
  *B32B 7/02* (2019.01)
  *B32B 3/30* (2006.01)
  *A61F 13/511* (2006.01)
  *A61F 13/512* (2006.01)
  *A61F 13/84* (2006.01)
  *D04H 11/08* (2006.01)
  *B32B 3/26* (2006.01)
  *B32B 27/02* (2006.01)
  *D04H 3/11* (2012.01)
  *B32B 3/24* (2006.01)
  *A61F 13/513* (2006.01)
  *D04H 1/4374* (2012.01)
  *B32B 27/16* (2006.01)
  *B32B 27/32* (2006.01)
  *B32B 27/18* (2006.01)
  *B32B 7/04* (2019.01)
  *D04H 3/007* (2012.01)
  *D04H 3/005* (2012.01)

(52) U.S. Cl.
  CPC .... *A61F 13/51113* (2013.01); *A61F 13/8405* (2013.01); *B32B 3/266* (2013.01); *B32B 3/30* (2013.01); *B32B 5/022* (2013.01); *B32B 5/26* (2013.01); *B32B 7/02* (2013.01); *B32B 27/02* (2013.01); *D04H 3/11* (2013.01); *D04H 11/08* (2013.01); *A61F 13/511* (2013.01); *A61F 13/5125* (2013.01); *A61F 2013/51178* (2013.01); *A61F 2013/51338* (2013.01); *A61F 2013/51366* (2013.01); *A61F 2013/8432* (2013.01); *B32B 7/04* (2013.01); *B32B 27/16* (2013.01); *B32B 27/18* (2013.01); *B32B 27/32* (2013.01); *B32B 2250/02* (2013.01); *B32B 2250/24* (2013.01); *B32B 2262/0253* (2013.01); *B32B 2262/04* (2013.01); *B32B 2262/12* (2013.01); *B32B 2305/20* (2013.01); *B32B 2307/404* (2013.01); *B32B 2307/4026* (2013.01); *B32B 2307/728* (2013.01); *B32B 2307/73* (2013.01); *B32B 2555/02* (2013.01); *D04H 1/4374* (2013.01); *D04H 3/005* (2013.01); *D04H 3/007* (2013.01); *Y10T 428/2395* (2015.04); *Y10T 428/23914* (2015.04); *Y10T 428/24182* (2015.01); *Y10T 428/24289* (2015.01); *Y10T 428/24322* (2015.01); *Y10T 428/24331* (2015.01); *Y10T 428/24479* (2015.01); *Y10T 428/24612* (2015.01); *Y10T 442/638* (2015.04); *Y10T 442/641* (2015.04); *Y10T 442/642* (2015.04); *Y10T 442/659* (2015.04); *Y10T 442/66* (2015.04); *Y10T 442/666* (2015.04); *Y10T 442/668* (2015.04); *Y10T 442/681* (2015.04); *Y10T 442/689* (2015.04)

(56) References Cited

U.S. PATENT DOCUMENTS

| | | | |
|---|---|---|---|
| 3,423,491 A | 1/1969 | Mclain | |
| 3,489,148 A | 1/1970 | Duncan et al. | |
| 3,643,738 A | 2/1972 | Dreher | |
| 3,785,918 A | 1/1974 | Kawai | |
| 3,870,567 A | 3/1975 | Palmer | |
| 4,020,230 A | 4/1977 | Mahoney | |
| 4,077,410 A | 3/1978 | Butterworth et al. | |
| 4,304,234 A | 12/1981 | Hartmann | |
| 4,345,907 A * | 8/1982 | Wegele | D06B 1/02 8/444 |
| 4,377,615 A | 3/1983 | Suzuki | |
| 4,503,098 A | 3/1985 | Potts | |
| 4,578,414 A | 3/1986 | Sawyer et al. | |
| 4,666,763 A | 5/1987 | King | |
| 4,668,566 A | 5/1987 | Braun | |
| 4,704,112 A | 11/1987 | Suzuki et al. | |
| 4,789,588 A | 12/1988 | Suzuki et al. | |
| 4,818,594 A | 4/1989 | Albien | |
| 4,874,567 A | 10/1989 | Lopatin | |
| 4,923,914 A | 5/1990 | Nohr et al. | |
| 5,009,651 A | 4/1991 | Kamishioiri et al. | |
| 5,045,387 A | 9/1991 | Schmalz | |
| 5,143,779 A * | 9/1992 | Newkirk | D04H 1/43918 442/364 |
| 5,171,238 A | 12/1992 | Kajander | |
| 5,198,292 A | 3/1993 | Lerner | |
| 5,273,596 A | 12/1993 | Newkirk | |
| 5,283,023 A | 2/1994 | Nohr | |
| 5,300,167 A | 4/1994 | Nohr | |
| 5,369,858 A * | 12/1994 | Gilmore | B32B 5/26 28/104 |
| 5,437,653 A | 8/1995 | Gilman et al. | |
| 5,449,352 A | 9/1995 | Nishino et al. | |
| 5,470,326 A | 11/1995 | Dabi | |
| 5,520,875 A | 5/1996 | Wnuk et al. | |
| 5,593,768 A | 1/1997 | Gessner | |
| 5,653,930 A | 8/1997 | Noda | |
| 5,658,639 A * | 8/1997 | Curro | A61F 13/00991 604/382 |
| 5,667,750 A | 9/1997 | Nohr et al. | |
| 5,722,966 A | 3/1998 | Christon et al. | |
| 5,750,256 A * | 5/1998 | Ito | D06M 13/224 442/79 |
| 5,763,334 A | 6/1998 | Gupta et al. | |
| 5,780,155 A | 7/1998 | Ishizawa et al. | |
| 5,780,368 A | 7/1998 | Noda | |
| 5,885,267 A | 3/1999 | Mishima et al. | |
| 5,935,682 A | 8/1999 | Wallstroem | |
| 5,961,505 A | 10/1999 | Coe et al. | |
| 5,969,026 A | 10/1999 | Mor et al. | |
| 5,972,497 A | 10/1999 | Hirwe et al. | |
| 5,989,478 A | 11/1999 | Ouellette et al. | |
| 6,117,801 A | 9/2000 | Mcginty | |
| 6,203,889 B1 | 3/2001 | Quincy, III | |
| 6,258,196 B1 | 7/2001 | Suzuki et al. | |
| 6,258,997 B1 | 7/2001 | Johansson et al. | |
| 6,274,218 B1 | 8/2001 | Shimizu | |
| 6,300,258 B1 | 10/2001 | Stano | |
| 6,353,149 B1 | 3/2002 | Stone | |
| 6,395,957 B1 * | 5/2002 | Chen | A61F 13/51305 442/79 |
| 6,498,284 B1 * | 12/2002 | Roe | A61L 15/20 604/378 |
| 6,602,386 B1 | 8/2003 | Takeuchi | |
| 6,686,303 B1 | 2/2004 | Haynes | |
| 6,699,806 B1 | 3/2004 | Takeuchi | |
| 6,713,011 B2 | 3/2004 | Chu | |
| 6,746,755 B2 | 6/2004 | Morrison | |
| 6,746,766 B2 | 6/2004 | Bond | |
| 6,767,498 B1 | 7/2004 | Talley, Jr. | |
| 6,818,295 B2 | 11/2004 | Bond | |
| 6,855,422 B2 | 2/2005 | Magill | |
| 6,890,649 B2 | 5/2005 | Hobbs | |
| 6,890,872 B2 | 5/2005 | Bond | |
| 6,916,969 B1 | 7/2005 | Helmfridsson et al. | |
| 6,946,506 B2 | 9/2005 | Bond | |
| 7,005,558 B1 | 2/2006 | Johansson et al. | |
| 7,150,912 B2 | 12/2006 | Mizutani | |
| 7,241,497 B2 | 7/2007 | Magill | |
| 7,267,789 B2 | 9/2007 | Chhabra | |
| 7,271,209 B2 | 9/2007 | Li | |
| 7,291,300 B2 | 11/2007 | Chhabra | |

(56) References Cited

U.S. PATENT DOCUMENTS

| | | | |
|---|---|---|---|
| 7,371,919 B1 | 5/2008 | Busam | |
| 7,781,353 B2 | 8/2010 | Snowden | |
| 7,981,226 B2 | 7/2011 | Pourdeyhimi | |
| 8,026,188 B2 | 9/2011 | Mor | |
| 8,168,550 B2 | 5/2012 | Collias | |
| 8,173,553 B2 | 5/2012 | Aoki | |
| 9,205,006 B2* | 12/2015 | Cheng | A61F 13/51113 |
| 10,271,999 B2 | 4/2019 | Arora | |
| 11,110,013 B2* | 9/2021 | Hammons | B32B 7/02 |
| 2002/0063364 A1 | 5/2002 | Taylor et al. | |
| 2002/0123731 A1 | 9/2002 | Yang et al. | |
| 2002/0160085 A1 | 10/2002 | Tokita et al. | |
| 2002/0168912 A1 | 11/2002 | Bond | |
| 2002/0169429 A1 | 11/2002 | Li | |
| 2003/0004436 A1 | 1/2003 | Schmidt et al. | |
| 2003/0045845 A1 | 3/2003 | Yoshioka | |
| 2003/0050618 A1 | 3/2003 | Kondo et al. | |
| 2003/0082968 A1* | 5/2003 | Sharma | B05D 1/045 |
| | | | 442/79 |
| 2003/0091803 A1 | 5/2003 | Bond | |
| 2003/0093046 A1* | 5/2003 | Kim | D04H 1/498 |
| | | | 604/367 |
| 2003/0104748 A1* | 6/2003 | Brown | D04H 1/55 |
| | | | 442/352 |
| 2003/0143376 A1 | 7/2003 | Toyoshima et al. | |
| 2003/0178166 A1 | 9/2003 | Takeuchi | |
| 2003/0203695 A1 | 10/2003 | Polanco | |
| 2003/0206943 A1 | 11/2003 | Hammons | |
| 2004/0005457 A1 | 1/2004 | Delucia | |
| 2004/0087924 A1 | 5/2004 | Sroda | |
| 2004/0092902 A1 | 5/2004 | Hoffman | |
| 2004/0116018 A1 | 6/2004 | Fenwick et al. | |
| 2004/0119207 A1 | 6/2004 | Stone | |
| 2004/0127128 A1 | 7/2004 | Thomas | |
| 2004/0131820 A1* | 7/2004 | Turner | B32B 5/12 |
| | | | 442/337 |
| 2004/0161994 A1 | 8/2004 | Arora | |
| 2004/0170816 A1 | 9/2004 | Watanabe | |
| 2004/0192818 A1 | 9/2004 | Oriani | |
| 2004/0209067 A1 | 10/2004 | Muth et al. | |
| 2004/0229008 A1 | 11/2004 | Hoying | |
| 2004/0265534 A1 | 12/2004 | Curro et al. | |
| 2005/0095695 A1 | 5/2005 | Schindler | |
| 2005/0096614 A1 | 5/2005 | Perez et al. | |
| 2005/0130539 A1 | 6/2005 | Allen et al. | |
| 2005/0154362 A1 | 7/2005 | Warren et al. | |
| 2005/0164587 A1 | 7/2005 | Melik | |
| 2005/0281978 A1 | 12/2005 | Cabell | |
| 2006/0008643 A1 | 1/2006 | Lin | |
| 2006/0019056 A1 | 1/2006 | Turner et al. | |
| 2006/0062816 A1* | 3/2006 | Gatto | A61F 13/472 |
| | | | 424/404 |
| 2006/0087053 A1 | 4/2006 | Odonnell | |
| 2006/0147804 A1 | 7/2006 | Yamamoto | |
| 2006/0154548 A1 | 7/2006 | Sheehan | |
| 2006/0172641 A1 | 8/2006 | Hennige | |
| 2006/0189956 A1 | 8/2006 | Catalan | |
| 2007/0023217 A1 | 2/2007 | Ishida | |
| 2007/0026753 A1 | 2/2007 | Neely | |
| 2007/0048498 A1 | 3/2007 | Cree | |
| 2007/0073256 A1 | 3/2007 | Ponomarenko et al. | |
| 2007/0077427 A1 | 4/2007 | Dugan | |
| 2007/0082573 A1 | 4/2007 | Noda | |
| 2007/0093770 A1* | 4/2007 | Ecker | A61F 13/4758 |
| | | | 604/385.01 |
| 2007/0135777 A1 | 6/2007 | Greene et al. | |
| 2007/0212545 A1 | 9/2007 | Cree | |
| 2008/0045638 A1 | 2/2008 | Chapman | |
| 2008/0070994 A1 | 3/2008 | Li | |
| 2008/0179777 A1 | 7/2008 | Wild | |
| 2008/0213587 A1 | 9/2008 | Kajita et al. | |
| 2009/0133446 A1 | 5/2009 | Burrow et al. | |
| 2009/0233046 A1 | 9/2009 | Iulianetti | |
| 2010/0024281 A1 | 2/2010 | Lemke | |
| 2010/0028638 A1 | 2/2010 | Reichardt | |
| 2010/0035014 A1 | 2/2010 | Hammons | |
| 2010/0036338 A1 | 2/2010 | Hammons | |
| 2010/0036346 A1 | 2/2010 | Hammons | |
| 2010/0036349 A1 | 2/2010 | Hammons | |
| 2010/0041292 A1 | 2/2010 | Kim | |
| 2010/0069864 A1 | 3/2010 | Berland et al. | |
| 2010/0201024 A1 | 8/2010 | Gibson | |
| 2010/0272938 A1 | 10/2010 | Mitchell | |
| 2010/0322989 A1 | 12/2010 | Martin | |
| 2010/0330326 A1* | 12/2010 | Turner | B32B 5/022 |
| | | | 428/88 |
| 2010/0330861 A1* | 12/2010 | Mor | D04H 1/00 |
| | | | 427/322 |
| 2011/0117176 A1 | 5/2011 | Klun | |
| 2011/0130430 A1 | 6/2011 | Sonneck | |
| 2011/0189916 A1 | 8/2011 | Haubruge et al. | |
| 2011/0196330 A1 | 8/2011 | Hammons | |
| 2011/0196332 A1 | 8/2011 | Cheng | |
| 2011/0217894 A1* | 9/2011 | Coslett | D04H 3/14 |
| | | | 442/382 |
| 2011/0306260 A1 | 12/2011 | Katsuya | |
| 2012/0009090 A1 | 1/2012 | Gadewar | |
| 2012/0064280 A1 | 3/2012 | Hammons | |
| 2012/0100350 A1 | 4/2012 | Shim | |
| 2012/0100772 A1 | 4/2012 | Hummelgaard et al. | |
| 2012/0109090 A1 | 5/2012 | Reichardt et al. | |
| 2012/0122363 A1 | 5/2012 | Owens | |
| 2012/0204760 A1 | 8/2012 | Puhala | |
| 2012/0209233 A1* | 8/2012 | Steffen | A61L 15/24 |
| | | | 604/370 |
| 2012/0296036 A1 | 11/2012 | Allen et al. | |
| 2012/0321869 A1 | 12/2012 | Allen | |
| 2012/0321870 A1 | 12/2012 | Allen | |
| 2012/0321871 A1 | 12/2012 | Bond | |
| 2012/0328804 A1 | 12/2012 | Allen | |
| 2013/0004691 A1 | 1/2013 | Allen et al. | |
| 2013/0008974 A1 | 1/2013 | Lange | |
| 2013/0012093 A1 | 1/2013 | Bond et al. | |
| 2013/0053478 A1 | 2/2013 | Bond | |
| 2013/0053480 A1 | 2/2013 | Allen | |
| 2013/0053901 A1 | 2/2013 | Cormier | |
| 2013/0158169 A1 | 6/2013 | Bond | |
| 2014/0066873 A1* | 3/2014 | Kawakami | D01F 8/06 |
| | | | 442/353 |
| 2014/0087941 A1 | 3/2014 | Allen, Jr. et al. | |
| 2014/0127459 A1 | 5/2014 | Xu | |
| 2014/0257216 A1 | 9/2014 | Gatto et al. | |
| 2014/0272261 A1 | 9/2014 | Udengaard et al. | |
| 2014/0272359 A1 | 9/2014 | Cheng et al. | |
| 2014/0276512 A1* | 9/2014 | Cheng | A61L 15/34 |
| | | | 604/366 |
| 2014/0343523 A1* | 11/2014 | Viens | A61L 15/225 |
| | | | 162/146 |
| 2015/0038933 A1 | 2/2015 | Day | |
| 2016/0067118 A1 | 3/2016 | Hammons et al. | |
| 2016/0153128 A1* | 6/2016 | Xie | D04H 1/559 |
| | | | 156/252 |
| 2016/0167334 A1 | 6/2016 | Arora et al. | |
| 2016/0220421 A1 | 8/2016 | Kuramochi | |
| 2020/0129345 A1 | 4/2020 | Hammons et al. | |

FOREIGN PATENT DOCUMENTS

| | | | | |
|---|---|---|---|---|
| CN | 101554487 A | | 10/2009 | |
| CN | 101892557 A | * | 11/2010 | ........... A61F 13/472 |
| CN | 201692175 U | | 1/2011 | |
| CN | 102673030 A | * | 9/2012 | |
| CN | 102673030 A | | 9/2012 | |
| CN | 202864521 U | * | 4/2013 | |
| CN | 103966684 A | | 8/2014 | |
| CN | 104873335 A | | 9/2015 | |
| DE | 3309530 C1 | | 10/1984 | |
| DE | 4437165 A1 | | 4/1996 | |
| DE | 19846857 C1 | * | 3/2000 | ........... A61F 13/512 |
| DE | 19846857 C1 | | 3/2000 | |
| DE | 19945548 C1 | | 1/2001 | |
| EP | 521016 B1 | * | 6/1995 | ........ A61F 13/51121 |

(56) References Cited

FOREIGN PATENT DOCUMENTS

| | | |
|---|---|---|
| EP | 0735089 A2 | 10/1996 |
| EP | 862402 | 9/1998 |
| EP | 0985392 A1 | 3/2000 |
| EP | 1086676 A1 | 3/2001 |
| EP | 2266514 A1 | 12/2010 |
| EP | 2411061 B1 | 11/2014 |
| FR | 2789690 A1 | 8/2000 |
| GB | 1225824 A | 3/1971 |
| GB | 200205029 | 4/2002 |
| JP | S55163044 A | 12/1980 |
| JP | 56011058 A | 2/1981 |
| JP | 62129054 | 6/1987 |
| JP | 62133164 | 6/1987 |
| JP | 62268861 | 11/1987 |
| JP | 1272861 | 10/1989 |
| JP | 02109561 A * | 4/1990 ............... F04D 1/08 |
| JP | H02168950 A | 6/1990 |
| JP | 2191759 | 7/1990 |
| JP | H03146755 A | 6/1991 |
| JP | H03185168 A | 8/1991 |
| JP | 3279452 | 12/1991 |
| JP | 04061857 A | 2/1992 |
| JP | 4091224 | 3/1992 |
| JP | 4136251 | 5/1992 |
| JP | H04300546 A | 10/1992 |
| JP | H04316673 A | 11/1992 |
| JP | 5051818 | 3/1993 |
| JP | H05115504 A | 5/1993 |
| JP | H05156557 A | 6/1993 |
| JP | 6070954 | 3/1994 |
| JP | H06280150 A | 4/1994 |
| JP | 6245952 | 9/1994 |
| JP | 7258964 | 10/1995 |
| JP | H08131941 A | 5/1996 |
| JP | 8158229 | 6/1996 |
| JP | 9049160 | 2/1997 |
| JP | 9111630 | 4/1997 |
| JP | 9273061 | 10/1997 |
| JP | 1025420 A1 | 1/1998 |
| JP | 10080445 A | 3/1998 |
| JP | 2000178865 | 6/2000 |
| JP | 2002061060 | 2/2002 |
| JP | 2002263137 | 9/2002 |
| JP | 2003012490 A | 1/2003 |
| JP | 2003138428 | 5/2003 |
| JP | 2004166832 A | 6/2004 |
| JP | 2004169261 | 6/2004 |
| JP | 2004209715 A | 7/2004 |
| JP | 2004229767 A | 8/2004 |
| JP | 2004285538 | 10/2004 |
| JP | 2004324025 A | 11/2004 |
| JP | 2005509468 A | 4/2005 |
| JP | 2005139594 A * | 6/2005 |
| JP | 2005324010 A * | 11/2005 |
| JP | 2005330637 | 12/2005 |
| JP | 2006510466 A | 3/2006 |
| JP | 2006255051 A | 9/2006 |
| JP | 2007113145 | 5/2007 |
| JP | 2007154380 A | 6/2007 |
| JP | 2007211376 A | 8/2007 |
| JP | 2008002037 | 1/2008 |
| JP | 2008095254 | 4/2008 |
| JP | 2008161584 | 7/2008 |
| JP | 200915005 | 7/2009 |
| JP | 2009228157 | 10/2009 |
| JP | 200301358 | 10/2013 |
| JP | 2013220286 A | 10/2013 |
| JP | 2014231666 A | 12/2014 |
| KR | 200377539 Y1 | 3/2005 |
| WO | 9515138 A1 | 6/1995 |
| WO | 1995023249 | 8/1995 |
| WO | 1995023250 | 8/1995 |
| WO | 9700656 A1 | 1/1997 |
| WO | 1998008475 | 3/1998 |
| WO | 1999006207 | 2/1999 |
| WO | 1998031735 | 10/1999 |
| WO | 2001090230 | 11/2001 |
| WO | 0209491 A2 | 2/2002 |
| WO | 2004014997 A2 | 2/2004 |
| WO | 2004058214 A1 | 7/2004 |
| WO | 2005042824 | 5/2005 |
| WO | 2010149239 A1 | 12/2010 |
| WO | 2011090425 A1 | 7/2011 |
| WO | 2012162083 A1 | 11/2012 |
| WO | 2012162085 A1 | 11/2012 |
| WO | 2012162092 A1 | 11/2012 |
| WO | 2012162130 A1 | 11/2012 |
| WO | 2012162135 | 11/2012 |
| WO | 2012162146 A1 | 11/2012 |
| WO | 2012162149 A1 | 11/2012 |
| WO | 2012162084 A3 | 3/2013 |

OTHER PUBLICATIONS

Machine Translation of JP-2005139594-A, Jun. 2005 (Year: 2005).*
Machine Translation of CN-101892557-A, Nov. 2010 (Year: 2010).*
Machine Translation of CN-102673030-A, Sep. 2012 (Year: 2012).*
Machine Translation of CN-202864521-U, Apr. 2013 (Year: 2013).*
International Search Report and Written Opinion, PCT/US2014/023252) dated Jun. 17, 2014.
All Office Actions, U.S. Appl. No. 13/833,311.
All Office Actions, U.S. Appl. No. 13/833,456.
All Office Actions, U.S. Appl. No. 13/833,503.
All Office Actions, U.S. Appl. No. 14/849,630.
All Office Actions, U.S. Appl. No. 14/861,004.
All Office Actions, U.S. Appl. No. 14/247,588.
Devesh, Tripathi, "Practical Guide to Polypropylene", Smithers RAPRA Technology, 2002.
Drexel University, Fiber Spinning—Drexel University Chemical Engineering Department, Feb. 16, 1999.
Flow Polymers Effect of SureFlo (TM) on Polypropylene Contamination in Nylon, 2011 Flow Polymers, LLC.
International Search Report and Written Opinion; Application Ser. No. PCT/US2015/049404; dated Mar. 17, 2016; 12 pages.
Kim, "Effects of Nucleating Agents on Preparation of Polypropylene Hollow Fiber Membranes by Melt Spinning Process", Maromolecular Research, vol. 10, No. 2, 127-134 pgs. (2002).
Kim, Microporous Membrane Formation Via Thermally Induced Phase Separation, Journal of Membrane Science, 64, (1991) 13-29.
Kim, Operation Parameters of Melt Spinning of Polypropylene Hollow Fiber Membranes, Journal of Membrane Science 108 (1995) 25-36, 12 pages.
Krupa, Polypropylene as a Potential Matrix for the Creation of Shape Stabilized Phase Change Materials, European Polymer Journal 43 (2007) 895-907, 13 pages.
Krupa, Thermal Properties of Polypropylene/Wax Blends, Thermochimica Acta 372 (2001) 137-141, 5 pages.
Mpanza, Comparison of Different Waxes as Processing Agents for Low-Density Polyethylene, Polymer Testing 25 (2006) 436-442, 7 pages.
Tolinski, Additives for Polyolefins, 2009, pp. 158-168.
Xiaofan, Flow Polymers, Effects of SureFlo® on the Crystallization and Melting Behavior of Semi-Crystalline Polyethylene (PE) and Polypropylene (PP) Systems, Flow Polymers, LLC, 3 pages.
Yoo, Effects of the Diluent Mixing Ratio and Conditions of the Thermally Induced Phase-Separation Process on the Pore Size of Microporous Polyethylene Membranes, Journal of Applied Polymer Science, vol. 108, 3154-3162 (2008).
"All Office Actions, U.S. Appl. No. 16/716,905".

* cited by examiner

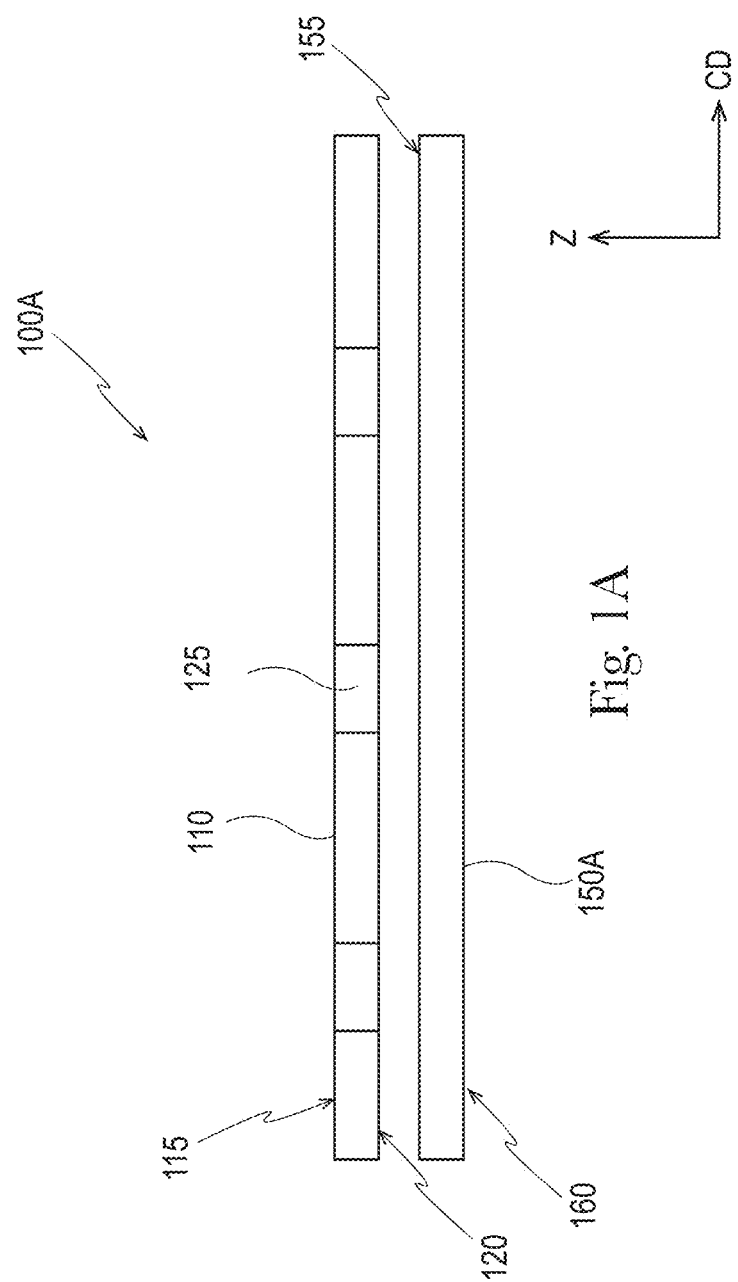

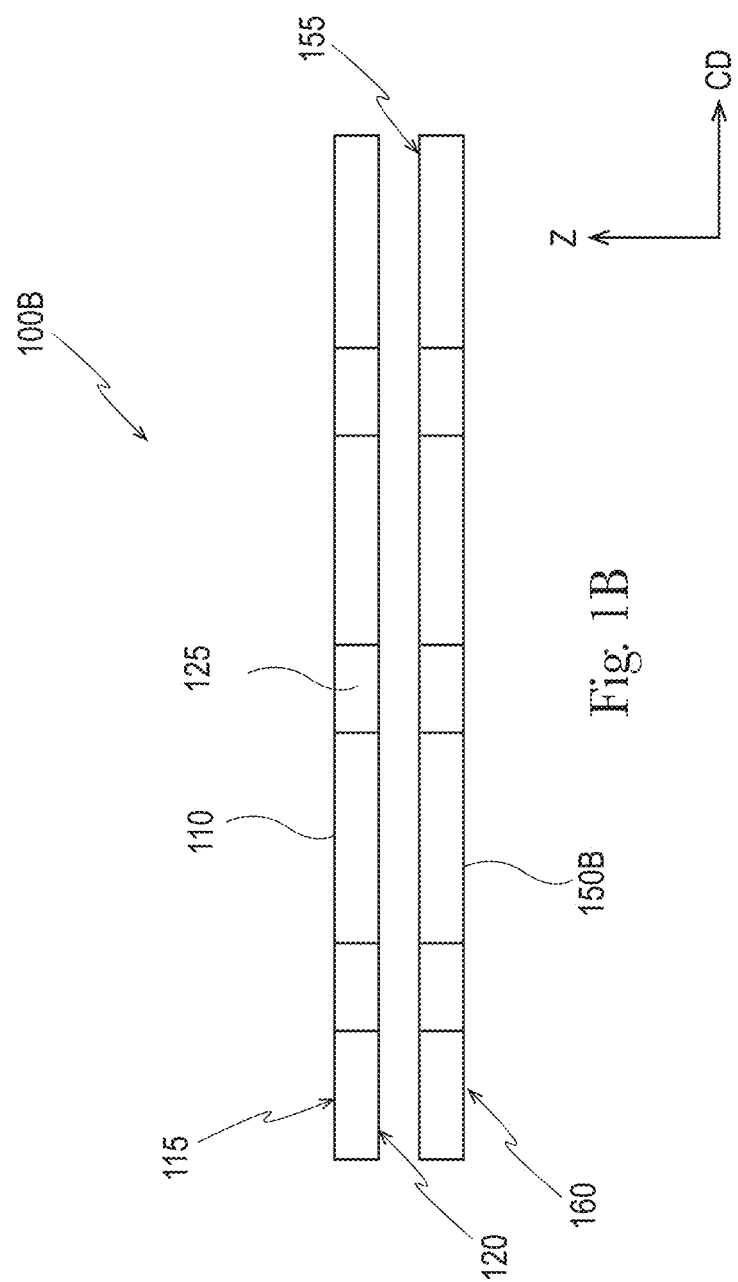

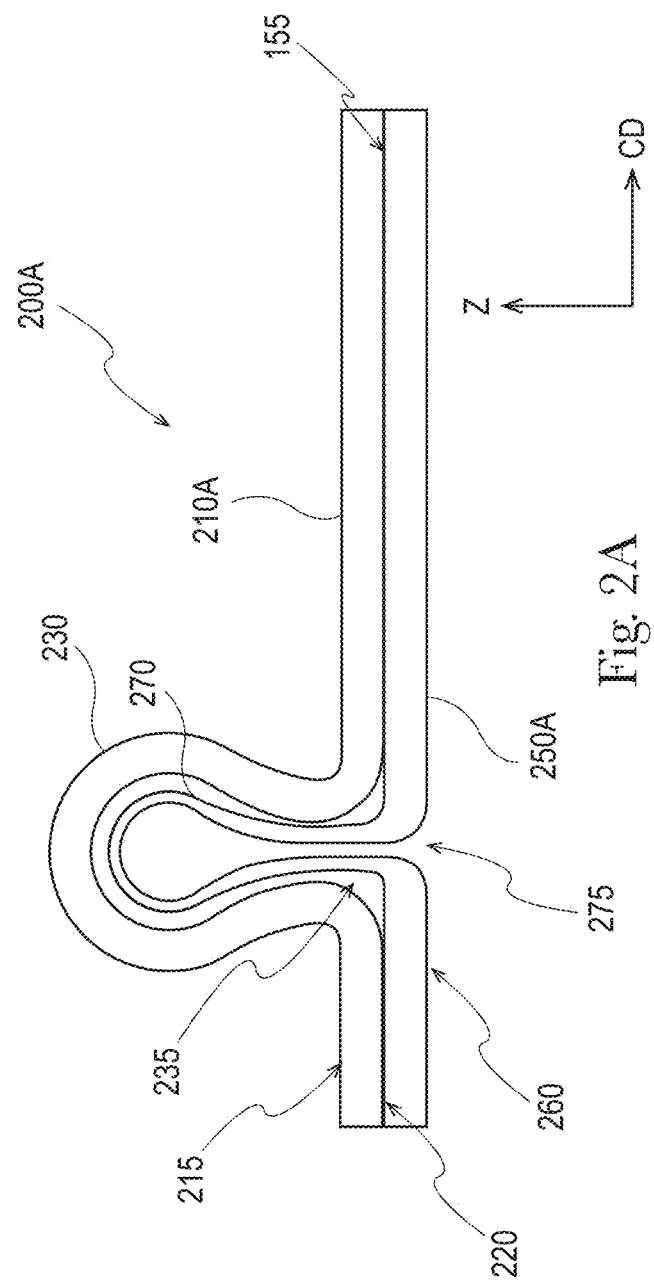

NONWOVEN WEBS WITH HYDROPHOBIC AND HYDROPHILIC LAYERS

FIELD OF THE INVENTION

The disclosure herein relates generally to a nonwoven web and an article incorporating the nonwoven web.

BACKGROUND OF THE INVENTION

Topsheets of disposable absorbent articles perform a valuable function. Topsheets are typically the interface between the disposable absorbent article and the user. As such, topsheets should be tactilely appealing to the user. Additionally, particularly in the context of hygiene articles, topsheets should blur/mask staining caused by menses and/or urine. If the topsheet does not successfully blur/mask the staining caused by menses/urine, the user may be left with the impression that the disposable absorbent article did not perform well.

There are a variety of top sheets known in the art. For example, in some conventional feminine hygiene articles, topsheets may comprise a film. Films are typically desirable because they provide good blurring/masking benefits regarding menses/urine staining. However, films are generally not considered to be soft without additional processing. Additionally, even with the additional processing, some users describe the film topsheet as having a "plastic feel". And, films can sometimes leave residual liquid, e.g. menses and/or urine, in contact with the skin of the wearer which can create an unpleasant feel as well as create an "unclean" perception in the mind of the user.

Other conventional feminine hygiene articles comprise nonwoven topsheets. Nonwoven topsheets can provide a soft feel to the user; however, nonwoven topsheets typically do not have good blurring/masking capability with regard to menses/urine stains.

Based on the foregoing, there is a need for a topsheet which can provide a soft feel to the user while also providing good masking of menses/urine stains.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1A is an exploded view of a nonwoven web of the present invention;

FIG. 1B is an exploded view of another embodiment of a nonwoven web of the present invention;

FIG. 2A is a side view of another embodiment of a nonwoven web of the present invention;

DETAILED DESCRIPTION OF THE INVENTION

Figure 2B:
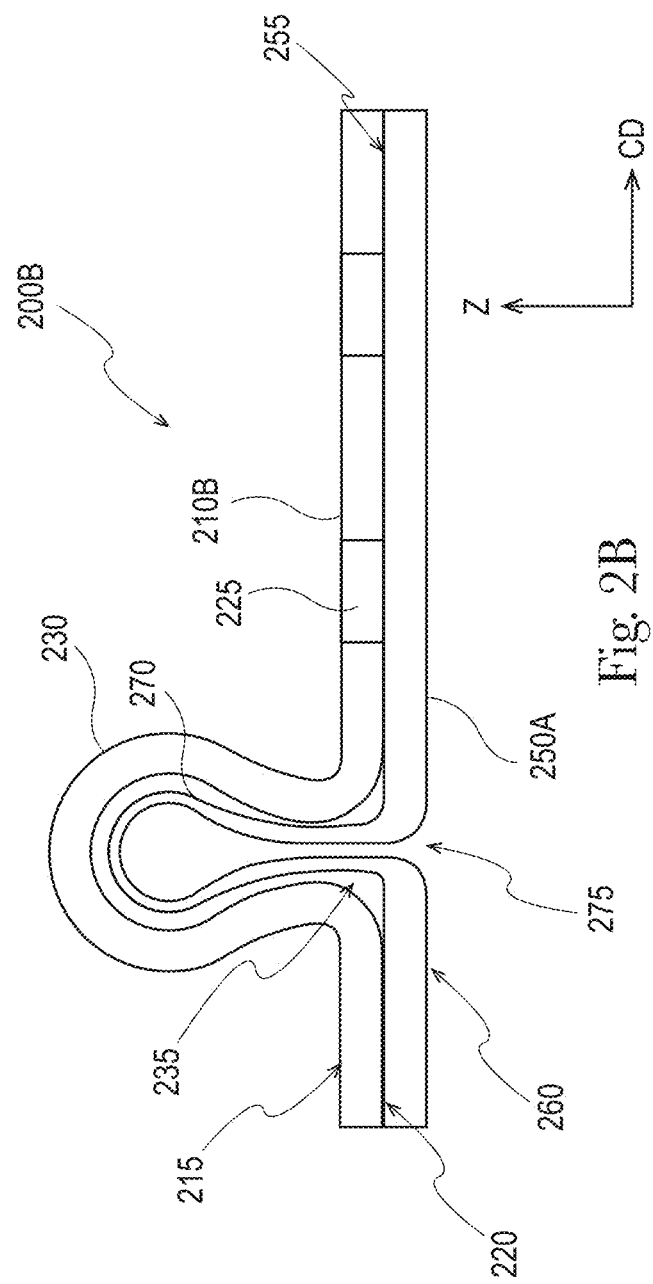
FIG. 2B is a side view of another embodiment of a nonwoven web of the present invention.

The term "fibrils" refers to projections, elongate projections, bumps that extend outwardly from a surface or generally radially outwardly from an outer surface of a fiber. In some instances, the projections, elongate projections, or bumps may extend radially outwardly relative to a longitudinal axis of the fiber. Radially outwardly means in the range of 1 to 89 degrees relative to the longitudinal axis. In still other instances, the projections, elongate projections, or bumps may extend radially outwardly from a surface of a fiber at least in a longitudinal central third of the fiber. The projections, elongate projections, or bumps comprise, consist of, or consist essentially of (e.g., 51% to 100% or 51% to 99%), melt additives. The projections, elongate projections, or bumps grow from the fibers post-nonwoven substrate formation only after a time period (e.g., 6-100 hours) under ambient conditions. Fibrils can be viewed using an SEM at, at least 1,000 times magnification.

As used herein, the term "nonwoven web" refers to a web having a structure of individual fibers or threads which are interlaid, but not in a repeating pattern as in a woven or knitted fabric, which do not typically have randomly oriented fibers. The basis weight of nonwoven fabrics is usually expressed in grams per square meter (gsm). The basis weight of a nonwoven web is the combined basis weight of the constituent layers and any other added components. Fiber diameters are usually expressed in microns; fiber size can also be expressed in denier, which is a unit of weight per length of fiber.

As used herein "philic" and "phobic" have meanings as well established in the art with respect to the contact angle of a referenced liquid on the surface of a material. Thus, a material having a liquid contact angle of greater than about 75 degrees is considered phobic, and a material having a liquid contact angle of less than about 75 degrees is considered philic.

By "substantially randomly oriented" it is meant that, due to processing conditions of a nonwoven layer, there may be a higher amount of fibers oriented in the machine direction (MD) than the cross direction (CD), or vice-versa.

The present invention pertains to a nonwoven web that is suitable for use in a disposable absorbent article. In some embodiments, the nonwoven web of the present invention is suitable for use as a topsheet in a disposable absorbent article. The nonwoven webs of the present invention comprise multiple layers of nonwoven material which can be integral or discrete as discussed herein. In some embodiments, the nonwoven web may comprise caps and tufts which provide a softness benefit and a masking benefit. Additionally, at least one of the nonwoven layers may comprise an additive which blooms at the surface of at least a portion of the constituent fibers of the at least one nonwoven layer. The inventors have found that the additive can provide masking benefits such that menses stains are less visible to a user of the disposable absorbent article. Additionally, the inventors have found that the additive can provide the treated nonwoven layer with better draining capability such that less fluid sticks to the fibers and/or interstices between intersecting fibers. The additive and its application to the nonwoven are similarly discussed hereafter. The better draining capability can lead to an increased feeling of dryness for the consumer.

In addition to tufts and/or caps or independently therefrom, webs of the present invention may comprise ridges and/or grooves. Ridges and/or grooves generally have a much greater length than do tufts and/or caps. For example, ridges and/or grooves may extend across a width of a web in the cross machine direction. In other forms, ridges and/or grooves may extend parallel with a machine direction to a larger extent than tufts. Still in other examples, ridges and/or grooves may have a length which s greater than a tuft and/or cap. In some forms, a plurality of discontinuous ridges and/or grooves may be provided. Methods of forming ridges and/or grooves are discussed further in U.S. Pat. No. 7,954,213; U.S. Patent Application Publication Nos. US2012/0045620; US2012/0196091; US2012/0321839; US2013/0022784; and US2013/0017370; and PCT Patent Application Publication Nos. WO2011/125893; and WO2012/137553.

Nonwoven Web

Nonwoven webs of the present invention have a machine direction (MD) (perpendicular to the plane of the sheet showing FIGS. 1A, 1B, 2A-2C, and 7-9), a cross machine direction (CD), and a Z direction, as is commonly known in the art of web manufacture. As stated previously, the nonwoven webs of the present invention comprise a laminate structure where the nonwoven web comprises a plurality of nonwoven material layers. The material layers may be discrete or may be integral as discussed hereafter. Additionally, each of the nonwoven webs of the present invention comprises at least two nonwoven material layers which are referred to herein as generally planar, two-dimensional webs. Also, each of the constituent nonwoven layers is a fibrous nonwoven web.

FIG. 1A shows an exploded view of a first embodiment of a nonwoven web 100A of the present invention. The first nonwoven layer 110 has a first surface 115 and a second surface 120, each of which are generally planar. Similarly, the second nonwoven layer 150A has a first surface 155 and a second surface 160 each of which are generally planar. The first surface 115 and 155 of the first nonwoven layer 110 and the second nonwoven layer 150A, respectively, can be body-facing surfaces and the second surfaces 120 and 160 of the first nonwoven layer 110 and the second nonwoven layer 150A, respectively, can be garment-facing surfaces.

The first nonwoven layer 110 and second nonwoven layer 150A can be a nonwoven web comprised of substantially randomly oriented fibers. For example, the first nonwoven layer 110 comprises a first plurality of substantially randomly oriented fibers, and the second nonwoven layer 150A comprises a second plurality of substantially randomly oriented fibers.

In one embodiment, the first nonwoven layer 110 may comprise a first plurality of apertures 125 that extend through the first nonwoven layer 110 from the first surface 115 to the second surface 120. In another embodiment, as shown in FIG. 1B, nonwoven web 100B may comprise the first nonwoven layer 110 comprising the first plurality of apertures 125 and a second nonwoven layer 150B comprising a second plurality of apertures 165. The second nonwoven layer 150B may otherwise be constructed similar to the second nonwoven layer 150A.

In some embodiments, the second plurality of apertures 165 may be substantially aligned with the first plurality of apertures 125. The aperturing of the first nonwoven layer 110 and the second nonwoven layer 150A or 150B may be by any suitable method; however, in order to provide the blurring/masking benefits described heretofore, the second nonwoven layer 150A, 150B should be in liquid communication with the first plurality of apertures. Liquid communication means that liquid insults to the first nonwoven layer are transferred to the second nonwoven layer. Generally, more interaction between the constituent fibers of the second nonwoven layer with the first nonwoven layer, can result in better liquid communication between the first nonwoven layer and the second nonwoven layer.

Preferable methods of aperturing nonwoven webs are described hereafter. The first nonwoven layer 110 and the second nonwoven layer 150A, 150B, may be joined about the periphery of each of the first plurality of apertures 125. For example, for those embodiments where apertures are created by melting fibers of the first nonwoven layer 110 typically an aperture periphery is formed. Additionally during the melting, the melted fiber material can form bonds with surrounding fibers including the fibers of the second nonwoven layer 150A or 150B. Where the constituent fibers of the first nonwoven layer 150A and the second nonwoven layer 150B are melted together, liquid communication between the first nonwoven layer 150A and the second nonwoven layer 150B can be enhanced. The same can occur with regard to the embodiment where both the first nonwoven layer 110 and the second nonwoven layer 150B comprise apertures. In some embodiments, the first nonwoven layer 110 and the second nonwoven layer 150A, 150B are attached to one another about at least a portion of the periphery of each of the first plurality of apertures 125. In some embodiments, the first nonwoven layer 110 and the second nonwoven layer 150A, 150B are attached to one another about at least a portion of the periphery of each of the second plurality of apertures 165.

The resultant nonwoven webs 100A and 100B of FIGS. 1A and 1B can provide a soft feel to a user of an absorbent article incorporating either of the nonwoven webs 100A or 100B as the topsheet of the absorbent article. An additional softness benefit and/or masking benefits can be gained by the structures described with regard to FIGS. 2A-2C and 8-10.

With regard to FIG. 2A, nonwoven web 200A constructed in accordance with the present invention is shown. The nonwoven web 200A may comprise a first nonwoven layer 210A having a generally planar first surface 215 and a generally planar second surface 220 opposed to the first surface 215 and a second nonwoven layer 250A having a generally planar first surface 255 and a generally planar second surface 260. The first nonwoven layer 210A comprises a first plurality of substantially randomly oriented fibers, and the second nonwoven layer 250A comprises a second plurality of substantially randomly oriented fibers. At least a portion of the second plurality of fibers in the second nonwoven layer 250A is in liquid communication with the first nonwoven layer 210A. Similar to the first nonwoven layer 110 and second nonwoven layers 150A and 150B (shown in FIGS. 1A and 1B), the respective surfaces of the first nonwoven layer 210A and second nonwoven layer 250A, can be arranged such that the first surfaces 215 and 255, respectively, are body-facing surfaces, and the second surfaces 220 and 260, respectively, can be arranged as garment-facing surfaces.

As shown, in some embodiments, the second surface 220 of the first nonwoven layer 210A may comprise a first plurality of discontinuities 235. The first plurality of discontinuities 235 are formed when localized areas of constituent fibers of the first nonwoven layer 210A are urged in the Z-direction such that these constituent fibers are disposed superjacent to the first surface 215 of the first nonwoven layer 210A. The disposition of the constituent fibers, may, in some embodiments, form a cap 230. The first nonwoven layer 210A may comprise a plurality of caps 230 positioned above the first surface 215. Each of the plurality of caps 230 can partially overlie at least one of the first plurality of discontinuities 235. For example, a first cap may at least partially overly a first discontinuity, and a second cap may at least partially overly a second discontinuity and so on. Caps 230 are discussed in additional detail hereafter.

Similarly, in some embodiments, the second surface 260 of the second nonwoven layer 250A may comprise a second plurality of discontinuities 275. The second plurality of discontinuities 275 can be formed as provided above with regard to the first plurality of discontinuities 235 in the first nonwoven layer 210A. Namely, localized areas of constituent fibers of the second nonwoven layer 250A are urged in the Z-direction such that these constituent fibers are disposed superjacent to the first surface 255 of the second nonwoven layer 250A. In some embodiments, this Z-direction urging also forces these constituent fibers to extend through the first plurality of discontinuities 235 in the second surface 220 of the first nonwoven layer 210A. The urging of the constituent fibers of the second nonwoven layer 250A forms tufts 270.

Tufts 270 extend through at least a portion of the first plurality of discontinuities 235 in the first nonwoven layer 210A. For example, tufts 270 may extend through at least one of the plurality of discontinuities 235 in the second surface 220 of the first nonwoven layers 210A and 210B. In other examples, tufts 270 may extend through each of the plurality of discontinuities 235. Embodiments are contemplated where tufts 270 of the second nonwoven layers 250A and 250B extend through more than about 90 percent of the plurality of discontinuities 235 in the second surface 220. In other embodiments, tufts 270 of the second nonwoven layer 250A and 250B extend through more than about 80 percent of the plurality of discontinuities 235, more than about 70 percent of the plurality of discontinuities 235, more than about 60 percent of the plurality of discontinuities 235, more than about 50 percent of the plurality of discontinuities 235, more than about 40 percent of the plurality of discontinuities 235, more than about 30 percent of the plurality of discontinuities 235, more than about 20 percent of the plurality of discontinuities, and/or less than about 100 percent, or less than about any of the above mentioned values or any number within the range of the values above or any range within the values above. Tufts 270 are discussed in additional detail hereafter.

Figure 3:
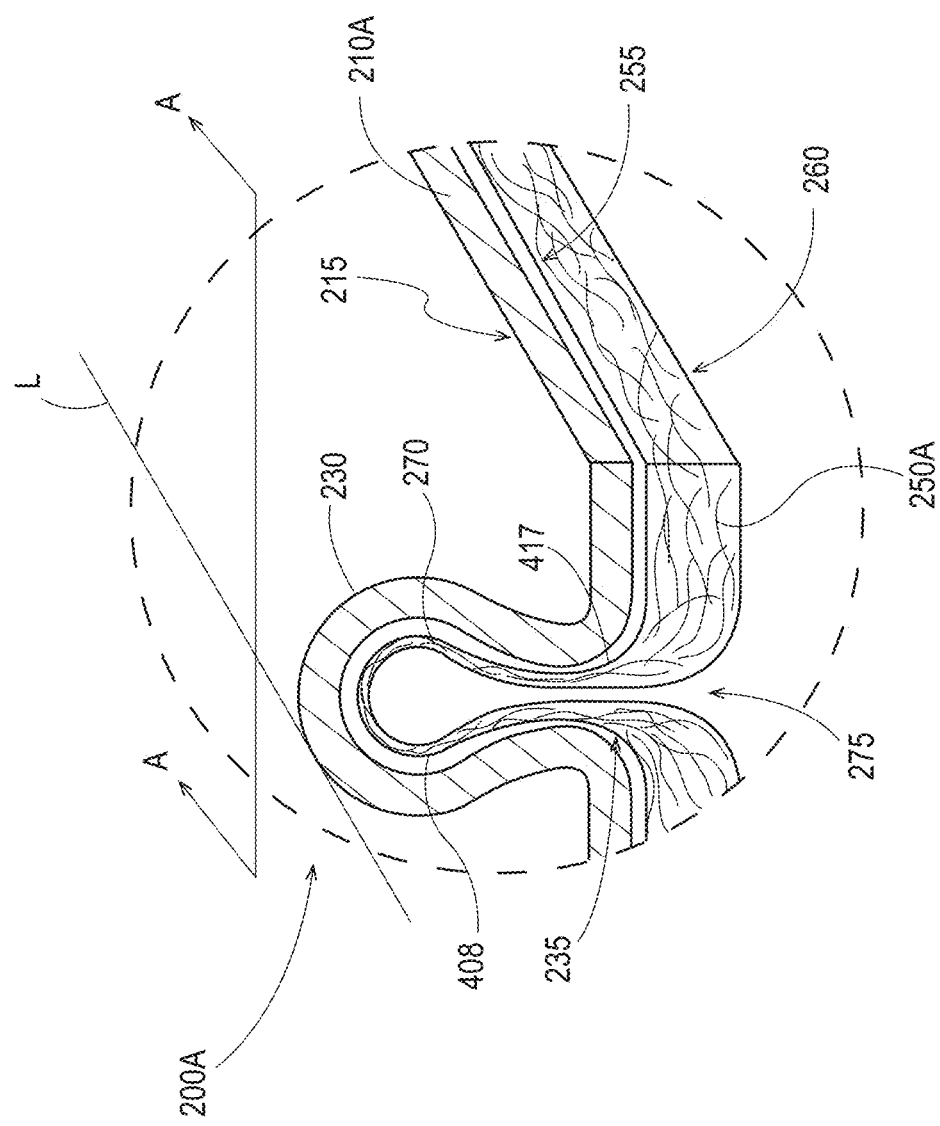
FIG. 3 is a close up view of a tuft and cap of the embodiments of FIGS. 2A-2C.

The abrupt change of orientation exhibited by the previously randomly-oriented fibers of the first nonwoven layer 210A and the second nonwoven layer 250A, define the first plurality of discontinuities 235 and the second plurality of discontinuities 275, respectively. Each of the first plurality of discontinuities 235 and the second plurality of discontinuities 275 exhibit a linearity that can be described as having a longitudinal axis generally parallel to longitudinal axis L (shown in FIG. 3) of the cap 230 and tuft 270.

With regard to FIG. 2B, a nonwoven web 200B may comprise a first nonwoven layer 210B which is constructed similar to the first nonwoven layer 210A but may additionally comprise a first plurality of apertures 225. The nonwoven web 200B may be constructed similar to the nonwoven web 200A except as provided with regard to the first nonwoven layer 210B. Similarly, with regard to FIG. 2C, a nonwoven web 200C may comprise the first nonwoven layer 210B and a second nonwoven layer 250B which comprises a second plurality of apertures 265. The second nonwoven layer 250B may otherwise be constructed similar to the second nonwoven layer 250A. The nonwoven web 200C may be constructed similar to the nonwoven web 200A and 200B except as provided with regard to the second nonwoven layer 250B. Additional embodiments are contemplated where the second nonwoven layer 250B comprises apertures in the absence of apertures in the first nonwoven layer 210A.

Referring again to FIGS. 2B-2C, the nonwoven webs 200B and 200C, the second plurality of fibers of the second nonwoven layers 250A and 250B can be in liquid communication with a first plurality of apertures 225 in the first nonwoven layer 210B and/or can be in liquid communication with the first nonwoven layer 210B. In some embodiments, at least a portion of the second plurality of apertures 265 may be substantially aligned with the first plurality of apertures 225 in the first nonwoven layer 210B.

The first nonwoven layer 210B and the second nonwoven layer 250B may be joined about the periphery of each of the first plurality of apertures 225. For example, for those embodiments where apertures are created by melting fibers of the first nonwoven layer 210B or the first nonwoven layer 210B together with the second nonwoven layer 250B, a bond may be created between the first nonwoven layer 210B and the second nonwoven layer 250B where the constituent fibers were melted. In some embodiments, the first nonwoven layer 210B and the second nonwoven layers 250A or 250B are attached to one another about at least a portion of the periphery of each of the first plurality of apertures 225. In some embodiments, the first nonwoven layer 210B and the second nonwoven layer 250B are attached to one another about at least a portion of the periphery of each of the second plurality of apertures 265. The second nonwoven layer 250A may be joined about the periphery of each of the first plurality of apertures 225 of the first nonwoven layer 210B.

While the first nonwoven layer 210A, the second nonwoven layer 250A, and the nonwoven web 200A are referenced below, the disclosure below is applicable for the nonwoven webs 200B, 200C, and first nonwoven layer 210B and second nonwoven layer 250B unless otherwise expressly stated.

Referencing FIGS. 3-6, caps 230 and tufts 270 alike can comprise a plurality of looped fibers that are substantially aligned such that each of the caps 230 and tufts 270 have a distinct linear orientation and a longitudinal axis L. By "looped" fibers it is meant to refer to fibers of the caps 230 that are integral with and begin and end in the first nonwoven layer 210A but extend generally outwardly in the Z-direction from the first surface 215 of the first nonwoven layer 210A. Similarly, "looped" fibers with regard to tufts 270 is meant to refer to fibers of the tufts 270 that are integral with and begin and end in the second nonwoven layer 250A but extend generally outwardly in the Z-direction from the first surface 255 of the second nonwoven layer 250A and extend beyond the first surface 215 of the first nonwoven layer 210A. By "aligned", it is meant that looped fibers are all generally oriented such that, if viewed in plan view as in FIG. 5, each of the looped fibers has a significant vector component parallel to a transverse axis T, and can have a major vector component parallel to the transverse axis T. The transverse axis T is generally orthogonal to longitudinal axis L in the MD-CD plane and the longitudinal axis L is generally parallel to the MD.

While the looped fibers of caps 230 are not shown as are the looped fibers 408 of the tufts 270, the looped fibers of the caps 230 may be similarly disposed as with regard to the looped fibers 408 of the tufts 270 except that as shown the looped fibers of the caps 230 may be disposed superjacent to the looped fibers of the tufts 270. As such, reference to the looped fibers herein shall be applicable to the looped fibers of the caps 230 and the looped fibers of the tufts 270 unless otherwise noted.

Figure 5:
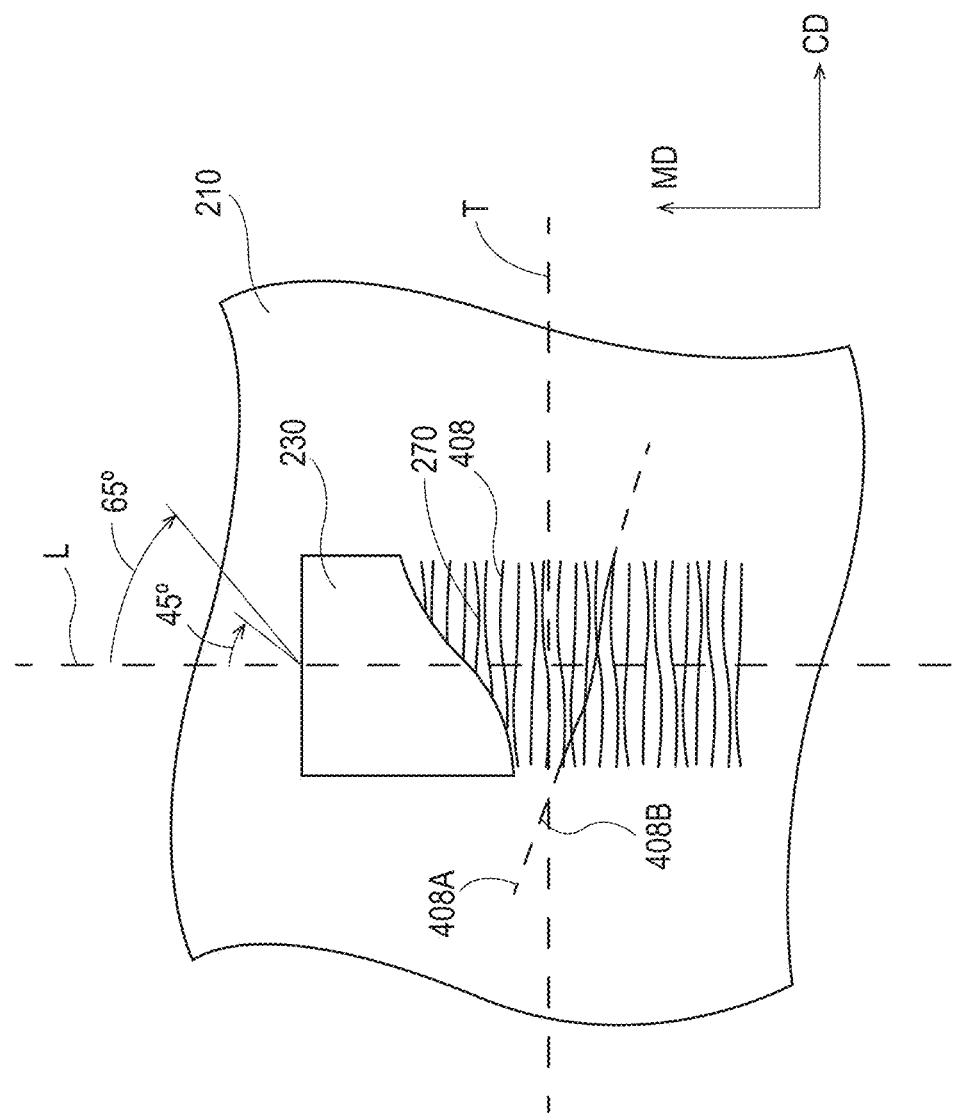
FIG. 5 is a plan view of the tuft and cap shown in FIG. 3.

As used herein, a looped fiber 408 oriented at an angle of greater than 45 degrees from the longitudinal axis L when viewed in plan view, as in FIG. 5, can have a significant vector component parallel to the transverse axis T. As used herein, a looped fiber 408 oriented at an angle of greater than 60 degrees from longitudinal axis L when viewed in plan view, can have a major vector component parallel to the transverse axis T. In some embodiments, at least 50%, at least 70%, and at least 90% of looped fibers 408 of tuft 270 have a significant or a major vector component parallel to transverse axis T. Fiber orientation can be determined by use of magnifying means if necessary, such as a microscope fitted with a suitable measurement 45 scale. In general, for a non-linear segment of fiber viewed in plan view, a straight-line approximation for both longitudinal axis L and the looped fibers 408 can be used for determining angle of looped fibers 408 from longitudinal axis L. For example, as shown in FIG. 5, one fiber 408A is shown emphasized by a heavy line, and its linear approximation 408B is shown as a dashed line. This fiber makes an angle of approximately 80 degrees with the longitudinal axis (measured counterclockwise from L).

In one embodiment, tufts 270 may be spaced apart from adjacent tufts 270, and similarly caps 230 may be spaced apart from adjacent caps 230. In some embodiments, each of the spaced apart tufts 270 and/or spaced apart caps 230 have generally parallel longitudinal axes L. The number of tufts 270 and/or caps 230 per unit area of a nonwoven web of the present invention, i.e., the area density of tufts 270 and/or caps 230, can be varied from one tuft per unit area, e.g., square centimeter to as high as 100 tufts per square centimeter or similarly with regard to caps 230. There can be at least 10, or at least 20 tufts 270 and/or caps 230 per square centimeter, depending on the end use. In general, the area density need not be uniform across the entire area of nonwoven webs of the present invention, and, in some embodiments, tufts 270 and/or caps 230 can be only in certain regions of nonwoven webs of the present invention, such as in regions having predetermined shapes, such as lines, stripes, bands, circles, and the like. In some embodiments, tufts 270 and/or caps 230 can be spaced sufficiently closely so as to effectively cover the first surface 215 of the first nonwoven 210A.

Tufts 270 are, in a sense, "punched above" the first nonwoven 210A and can be "locked" in place by frictional engagement with discontinuities 235 of the second surface 220. In some embodiments, for example, the lateral width of a discontinuity 235 (i.e., the dimension measured parallel to its transverse axis) can be less than the maximum width of the tooth that formed the discontinuity (per the process described below). This indicates a certain amount of recovery at the discontinuity that tends to constrain tuft 270 from pulling back out through discontinuity 235. The frictional engagement of the tufts 270 and discontinuities 235 can provide a structure having permanent tufting on one side that can be formed without adhesives or thermal bonding. This tufting can provide a softness benefit to the user of the article incorporating the nonwoven web.

Figure 2C:
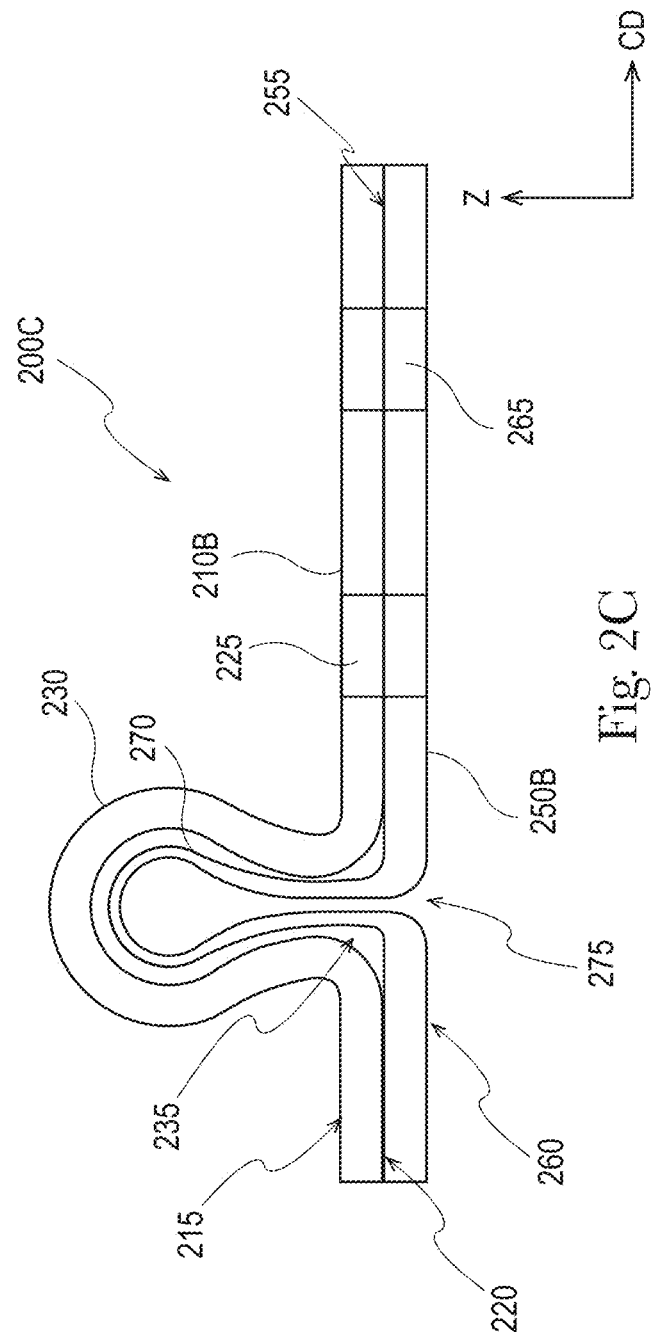
FIG. 2C is a side view of another embodiment of a nonwoven web of the present invention.

While the embodiments described with regard to FIGS. 2A-2C, have longitudinal axes L of tufts 270 and/or caps 230 generally aligned in the MD, tufts 270 and/or caps 230 and, therefore, longitudinal axes L, can, in principle, be aligned in any orientation with respect to the MD or CD. Therefore, in general, it can be said that for each tuft 270 and/or cap 230, the looped aligned fibers 408 (shown in FIGS. 3 and 4) are aligned generally orthogonal to the longitudinal axis L such that they have a significant vector component parallel to transverse axis T, and can have a major vector component parallel to transverse axis T.

Figure 4:
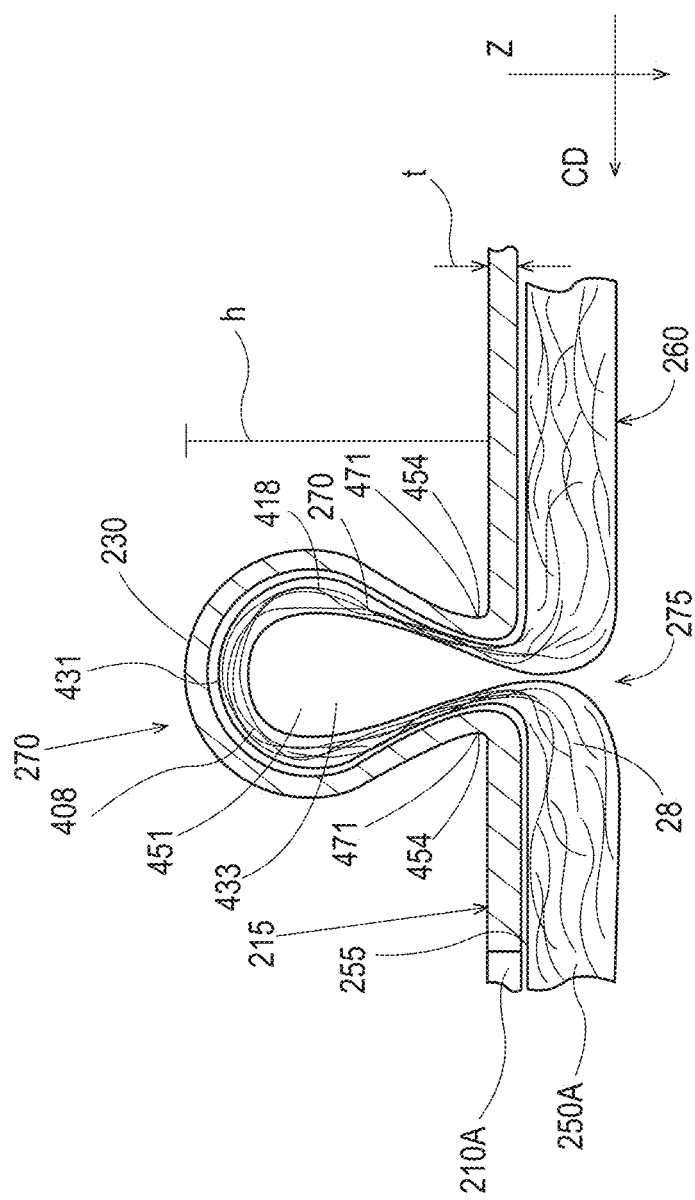
FIG. 4 is a cross sectional view showing the tuft and cap of FIG. 3 and taken along line 4-4 of FIG. 3.

Referring again to FIGS. 3 and 4, in some embodiments, as described below, another characteristic of tufts 270 can be their generally open structure characterized by open void area 433 defined interiorly of tufts 270. The void area 433 may have a shape that is wider or larger at a distal portion 431 of the tuft 270 and narrower at the tuft base 417 of the tuft 270. This is opposite to the shape of the tooth which is used to form the tuft 270 which is discussed hereafter. The term "void area" is not meant to refer to an area completely free of any fibers. Rather, the term is meant as a general description of the general appearance of tufts 270. Therefore, it may be that in some tufts 270 a non-looped fiber 418 or a plurality of loose non-looped fibers 418 may be present in the void area 433. By "open" void area is meant that the two longitudinal ends of tuft 270 are generally open and free of fibers, such that tuft 270 can form something like a "tunnel" structure in an uncompressed state, as shown in FIG. 4. Generally, discontinuities 275 at the tuft base 417 are narrow. The closing or narrowing or squeezing of other fibers at the tuft base 417 can help to stabilize the tufts 270. The general shape of the caps 230 may be similar to that of the tufts 270; however, as shown in FIGS. 2A-2C, void space of a cap 230 may be occupied, in part, by a tuft 270.

Due to the nature of many nonwoven webs useful as second nonwoven layer 250A (shown in FIG. 2A) discontinuities 275 may not be as distinctly noticeable as tufts 270. For this reason, the discontinuities 275 on the second surface 260 of the second nonwoven layer 250A can go unnoticed and may be generally undetected unless nonwoven web 200A (shown in FIG. 2A) is closely inspected. As such, the second surface 260 of the second nonwoven 250A can have the look and feel of an un-tufted first nonwoven layer. Thus in some embodiments, nonwoven webs 200A can have the textured look and feel of terry cloth on one surface, and a relatively smooth, soft look and feel on second surface. In other embodiments, discontinuities 275 can appear as apertures, and may be apertures through the second nonwoven 250A via the ends of the tunnel-like tufts 270.

Looped fibers 408 and/or non-looped fibers 418 of tuft 270 can originate and extend from either the first surface 255 or the second surface 260 of second nonwoven layer 250A. Of course the looped fibers 408 or non-looped fibers 418 of tuft 270 can also extend from an interior of second nonwoven layer 250A. In general, with regard to tufts 270, the looped fibers 408 and non-looped fibers 418 comprise fibers that are integral with and extend from the fibers of the second nonwoven layer 250A.

Similarly, caps 230 may comprise looped fibers and/or non-looped fibers which originate and extend from either the first surface 215 or the second surface 220 of the first nonwoven layer 210A. The looped fibers and/or non-looped fibers may also extend from an interior of the first nonwoven layer 210A. The looped fibers and/or non-looped fibers of the caps 230 are integral with and extend from the fibers of the first nonwoven layer 210A.

In some embodiments, the extension and/or urging of looped fibers 408 and non-looped fibers 418 can be accompanied by a general reduction in fiber cross sectional dimension (e.g., diameter for round fibers) due to plastic deformation of the fibers and Poisson's ratio effects. Therefore, the aligned looped fibers 408 of caps 230 and/or tufts 270 can have a tuft average fiber diameter less than the average fiber diameter of the fibers of the first nonwoven layer 210A and the second nonwoven layer 250A, respectively. It is believed that this reduction in fiber diameter can contribute to the perceived softness. Still in other embodiments, the fibers/nonwoven material may be selected such that there is little to no reduction in fiber cross section when fibers are urged either in the Z-direction or negative Z-direction due to fiber mobility. Embodiments are contemplated where the first and/or second nonwoven layers are chosen to reduce the likelihood of thinning of the fibers and enhance fiber mobility.

Fiber-to-fiber mobility can be increased by reducing or eliminating the fiber-to-fiber bonds (e.g. with lower bond area or higher bond spacing or lower bond temperature in point bonded nonwovens or via reduced temperature or air flow in through-air bonded nonwovens). Thermal bonds can be completely eliminated (i.e. avoided by not bonding) or significantly reduced in certain nonwoven webs to increase fiber-to-fiber mobility. Similarly, hydroentangled webs can be less entangled to increase fiber-to-fiber mobility. For any web, lubricating it prior to processing as disclosed herein can also increase fiber-to-fiber mobility. For example, a mineral oil or silicone lubricant can be applied. Additionally a slip agent or plasticizing agent can be added to some synthetic fiber webs, such as polyethylene or polypropylene.

Figure 6:
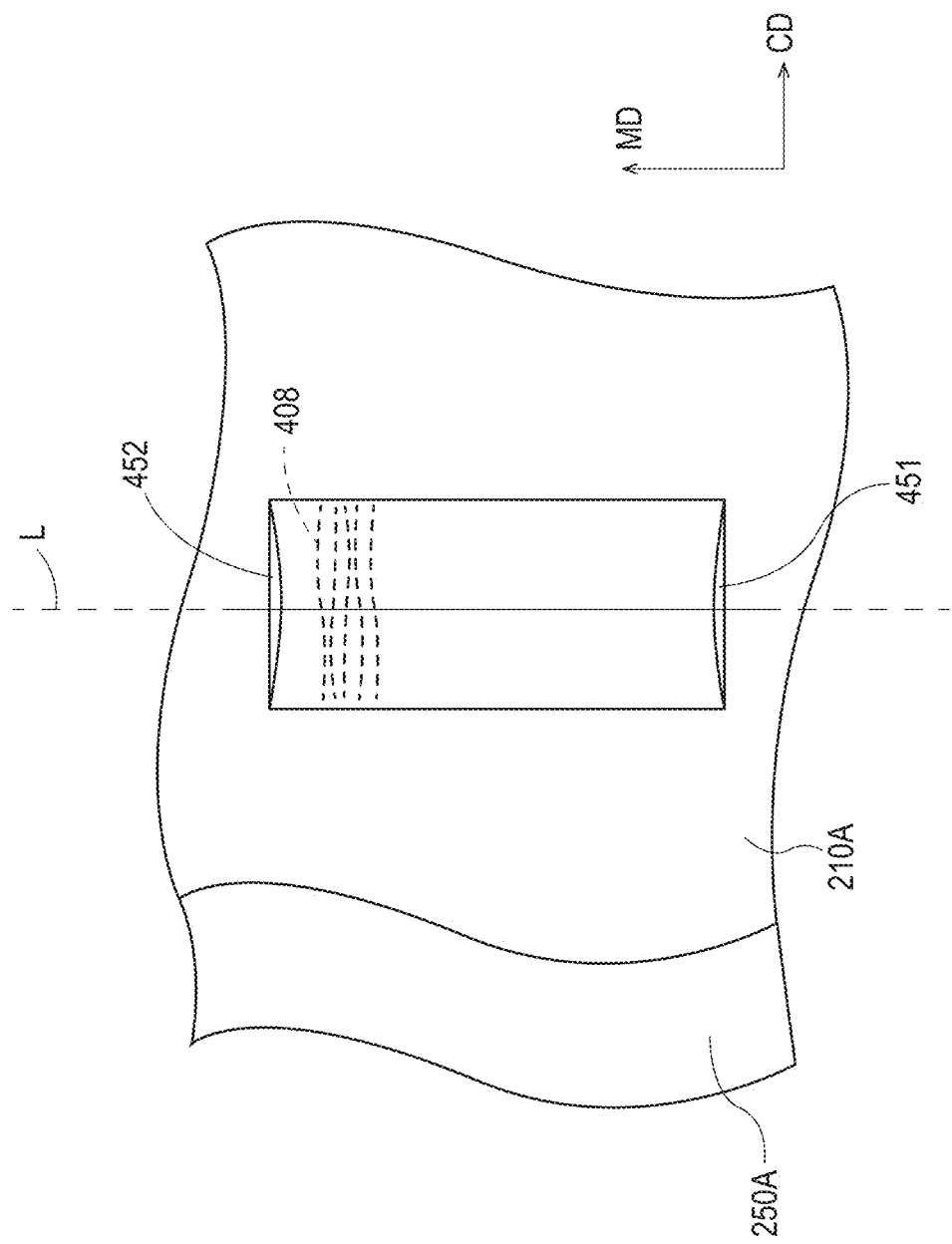
FIG. 6 is a plan view of the tuft and cap shown in FIG. 3.

Referencing FIGS. 4 and 6, in some embodiments, the void space 433 of tufts 270 may comprise a first void space opening 451 which can be arch shaped such that the first void space opening 451 is broadest proximal the first surface 215 of the first nonwoven layer 210A and generally becomes narrower towards the portion of the cap covering the distal portion 431 of the tuft 270. The cap 230 can have a cap base 471 proximal the first surface 215 of the first nonwoven layer 210A, 210B. The cap base 471 can be narrower than a portion of the cap 230 away from the cap base 471. That is, the distance between extension locations 454 can be less than maximum lateral extent of the cap 230 away (i.e. above) from the cap base 471. In some embodiments, the first void space opening 451 can be uppercase omega shaped ($\Omega$) such the first void space opening 451 is narrower proximal the first surface 215 of the first nonwoven layer 210A than at a location midway between the tuft base 417 and the distal portion 431 of tuft 270. Similarly, if a second void space opening 452 is present, the second void space opening 452 can be arch shaped such that the second void space opening 452 is broadest proximal the first surface 215 of the first nonwoven layer 210A and generally narrows towards the portion of the cap 230 covering the distal portion 431 of the tuft 270. The second void space opening 452 can be uppercase omega shaped ($\Omega$) such that the second void space opening 452 is narrower proximal the first surface 215 of the first nonwoven layer 210A than at a location midway between the tuft base 417 and the distal portion 431 of tuft 270. The second void space opening 452 can oppose the first void space opening 451 in that at least part of the tuft 270 is between second void space opening 452 and first void space opening 451. The first void space opening 451, the second void space opening 452, and any additional openings can make the nonwoven web 200A liquid pervious. In some forms, the tufts 270 and/or caps 230 may have a shape which is similar to an inverted capital "U"—specifically for those forms where the tufts 270 and/or caps 230 are provided in the positive Z-direction. In other forms, where the tufts and/or caps are provided in the negative Z-direction, the tufts and/or caps may have the shape of a capital "U". The "U" shaped tufts and/or caps may appear like a plurality of bumps on the web.

If there is a first void space opening 451 and a second void space opening 452, the cap 230 can integrally extend from the first nonwoven layer 210A at at least two extension locations 454 spaced apart from one another by the first void space opening 451 and second void space opening 452. The at least two extension locations 454 can be at opposing positions on opposing sides of the tuft 270. The cap 230 can integrally extend from the first nonwoven layer 210A at at least two extension locations 454.

Caps of the present invention are thought to mask or partially mask fluid that is collected by the nonwoven web and remains in the capillaries between fibers 408 of the tufts. Such a nonwoven web employed in an absorbent article such as a wipe, a sanitary napkin, a tampon, or a diaper can be appealing to the user (or caregiver) in that potentially unsightly fluids retained in the capillaries between fibers 408 of the tufts will be obscured or partially obscured from the viewer. The caps cover or partially cover tufts in which fluids can be held and can make the nonwoven web appear less soiled.

Figure 7:
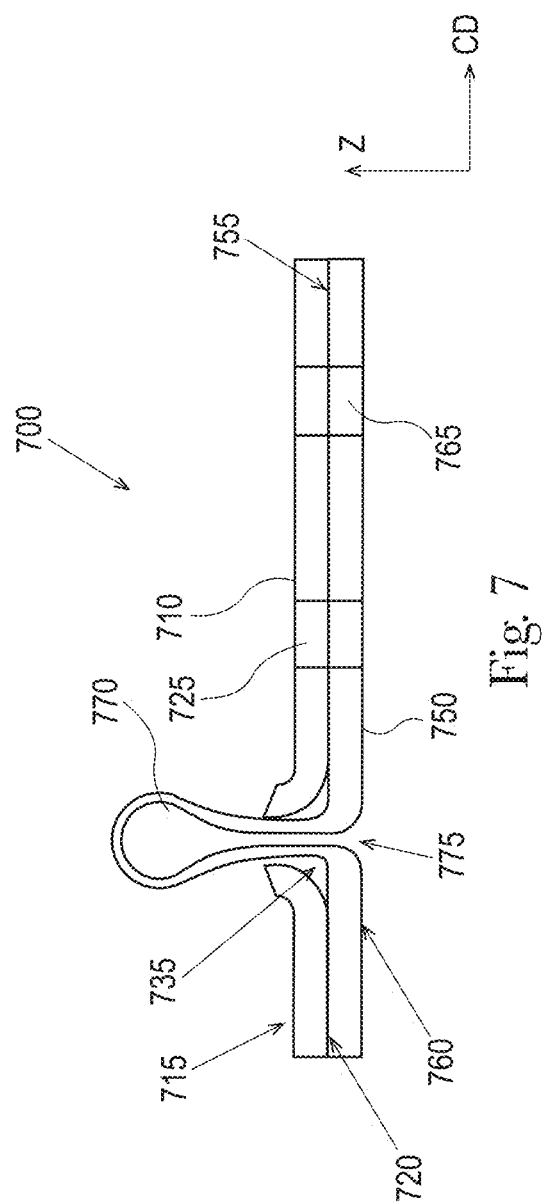
FIG. 7 is a side view of another embodiment of a nonwoven web of the present invention.
Figure 8:
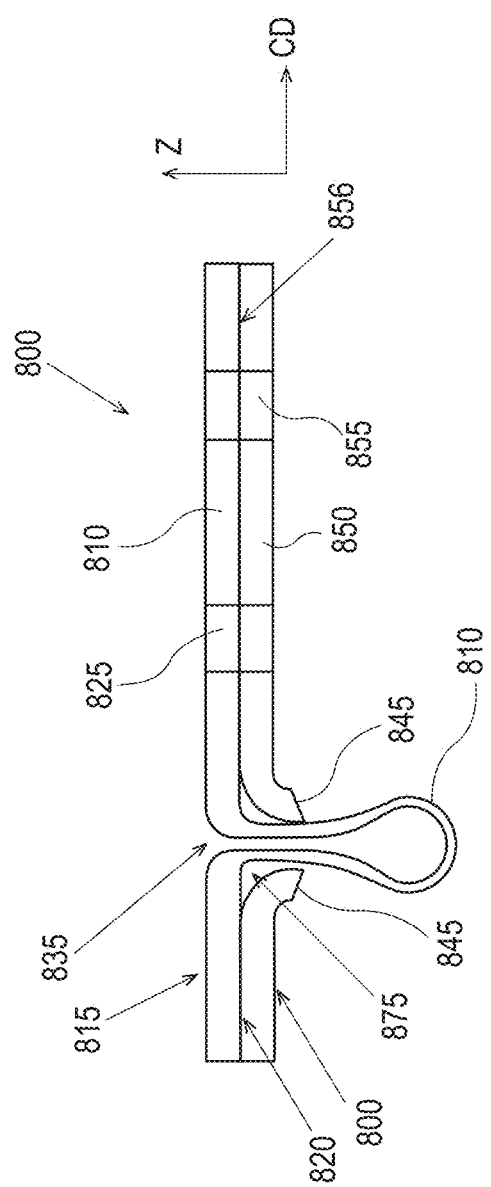
FIG. 8 is a side view of another embodiment of a nonwoven web of the present invention.
Figure 9:
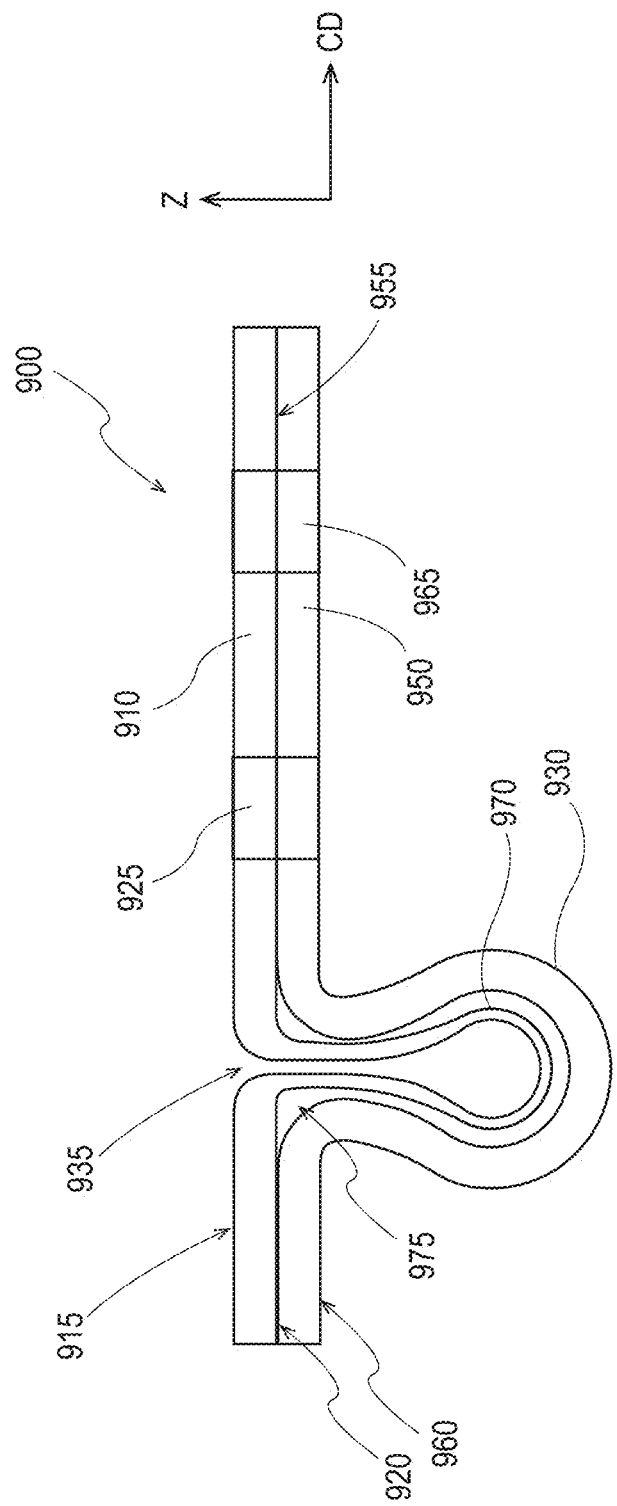
FIG. 9 is a side view of another embodiment of a nonwoven web of the present invention.

Embodiments including additional arrangements of caps and/or tufts are provided with respect to FIGS. 7-9. With regard to FIG. 7, a nonwoven web 700 is shown which comprises a first nonwoven layer 710 and a second nonwoven layer 750. The first nonwoven layer 710 comprises a generally planar first surface 715 and a generally planar second surface 720 opposed to the first surface 715, and the second nonwoven layer 750 has a generally planar first surface 755 and a generally planar second surface 760. The first nonwoven layer 710 comprises a first plurality of substantially randomly oriented fibers, and the second nonwoven layer 750 comprises a second plurality of substantially randomly oriented fibers. At least a portion of the second plurality of fibers in the second nonwoven layer 750 is in liquid communication with the first nonwoven layer 710. Similar to the first nonwoven layer 110 and second nonwoven layers 150A and 150B (shown in FIGS. 1A and 1B), the respective surfaces of the first nonwoven layer 710 and second nonwoven layer 750, can be arranged such that the first surfaces 715 and 755, respectively, are body-facing surfaces, and the second surfaces 720 and 760, respectively, can be arranged as garment-facing surfaces.

While the embodiment shown in FIG. 7 depicts the first nonwoven layer 710 having a first plurality of apertures 725 and the second nonwoven layer 750 with a second plurality of apertures, these are optional. For example, embodiments are contemplated where the first nonwoven layer 710 comprises the first plurality of apertures 725 while the second nonwoven layer 750 does not comprise apertures. As another example, the second nonwoven layer 750 may comprise the second plurality of apertures 765 while the first nonwoven layer 710 does not comprise apertures. Additional embodiments are contemplated where both the first nonwoven layer 710 and the second nonwoven layer 750 are sans apertures.

As shown, in some embodiments, the second surface 720 of the first nonwoven layer 710 may comprise a first plurality of discontinuities 735. The first plurality of discontinuities 735 are formed when localized areas of constituent fibers of the first nonwoven layer 210A are urged in the Z-direction such that these constituent fibers are disposed superjacent to the first surface 715 of the first nonwoven layer 710. However, instead of forming a cap 230 (shown in FIGS. 2A-2C and 3-6), the urging in the Z-direction of the constituent fibers of the first nonwoven layer 710 may be such that a plurality of fibers break thereby forming the first plurality of discontinuities 735.

As shown, in some embodiments, the second surface 760 of the second nonwoven layer 750 may comprise a second plurality of discontinuities 775 which may be configured as described with regard to the second plurality of discontinuities 275 (shown in FIGS. 2A-2C and 3-4). Namely, localized areas of constituent fibers of the second nonwoven layer 750 are urged in the Z-direction such that these constituent fibers are disposed superjacent to the first surface 755 of the second nonwoven layer 750. This Z-direction urging also forces these constituent fibers to extend through the first plurality of discontinuities 735 in the second surface 720 of the first nonwoven layer 710. The extension of the constituent fibers of the second nonwoven layer 750 forms tufts 770.

Tufts 770 extend through at least a portion of the first plurality of discontinuities 735 in the first nonwoven layer 710. Tufts 770 may be configured as described herein with regard to tufts 230 (shown in FIGS. 2A-2C and 3-4). As shown, in some embodiments, tufts 770 may be uncovered by a corresponding cap formed by the constituent fibers of the first nonwoven layer 710.

With regard to FIG. 8, a nonwoven web 800 constructed in accordance with the present invention is shown. The nonwoven web 800 may comprise a first nonwoven layer 810 having a generally planar first surface 815 and a generally planar second surface 820 opposed to the first surface 815 and a second nonwoven layer 850 having a generally planar first surface 855 and a generally planar second surface 860. The first nonwoven layer 810 comprises a first plurality of substantially randomly oriented fibers, and the second nonwoven layer 850 comprises a second plurality of substantially randomly oriented fibers. At least a portion of the second plurality of fibers in the second nonwoven layer 850 is in liquid communication with the first nonwoven layer 810. Similar to the first nonwoven layer 110 and second nonwoven layers 150A and 150B (shown in FIGS. 1A and 1B), the respective surfaces of the first nonwoven layer 810 and second nonwoven layer 850, can be arranged such that the first surfaces 815 and 855, respectively, are body-facing surfaces, and the second surfaces 820 and 860, respectively, can be arranged as garment-facing surfaces.

While the embodiment shown in FIG. 8 depicts the first nonwoven layer 810 having a first plurality of apertures 825 and the second nonwoven layer 850 with a second plurality of apertures, these are optional. For example, embodiments are contemplated where the first nonwoven layer 810 comprises the first plurality of apertures 825 while the second nonwoven layer 750 does not comprise apertures. As another example, the second nonwoven layer 850 may comprise the second plurality of apertures 865 while the first nonwoven layer 810 does not comprise apertures. Additional embodiments are contemplated where both the first nonwoven layer 810 and the second nonwoven layer 850 are sans apertures.

As shown, in some embodiments, the first surface 815 of the first nonwoven layer 810 may comprise a first plurality of discontinuities 835. The first plurality of discontinuities 835 are formed when localized areas of constituent fibers of the first nonwoven layer 810 are urged in the negative Z-direction such that these constituent fibers are disposed subjacent to the first surface 815 of the first nonwoven layer 810 thereby forming tufts 870. In some embodiments, the tufts 870 may extend beyond the second surface 860 of the second nonwoven layer 850 such that at least a portion of the tuft 870 is subjacent to the second surface 860.

The second nonwoven layer 850 may comprise a second plurality of discontinuities 875. As shown, in some embodiments, the plurality of tufts 870 may extend through the second plurality of discontinuities 875. The second plurality of discontinuities 875 may be created when localized areas of constituent fibers of the second nonwoven layer 850 are urged in the negative Z-direction such that these constituent fibers are disposed subjacent to the first surface 855 of the second nonwoven layer 850. However, instead of forming a cap 230 (shown in FIGS. 2A-2C and 3-6), the urging in the Z-direction of the constituent fibers of the second nonwoven layer 850 may be such that a plurality of fibers break thereby forming the second plurality of discontinuities 875.

Tufts 870 extend through at least a portion of the second plurality of discontinuities 875 in the second nonwoven layer 850. For example, tufts 870 may extend through at least one of the plurality of discontinuities 875 in the second surface 860 of the second nonwoven layer 850. Tufts 870 may be configured as described herein with regard to tufts 230 (shown in FIGS. 2A-2C and 3-4). As shown, in some embodiments, tufts 870 may be uncovered by a corresponding cap formed by the constituent fibers of the second nonwoven layer 860. The nonwoven web 800 can provide a softness benefit as well as improve fluid communication to an absorbent core of a disposable absorbent article incorporating such nonwoven web 800.

With regard to FIG. 9, nonwoven web 900, constructed in accordance with the present invention, is shown. The nonwoven web 900 may comprise a first nonwoven layer 910 having a generally planar first surface 915 and a generally planar second surface 920 opposed to the first surface 915 and a second nonwoven layer 950 having a generally planar first surface 955 and a generally planar second surface 960. The first nonwoven layer 910 comprises a first plurality of substantially randomly oriented fibers, and the second nonwoven layer 950 comprises a second plurality of substantially randomly oriented fibers. At least a portion of the second plurality of fibers in the second nonwoven layer 950 is in liquid communication with the first nonwoven layer 910. Similar to the first nonwoven layer 910 and second nonwoven layers 150A and 150B (shown in FIGS. 1A and 1B), the respective surfaces of the first nonwoven layer 910 and second nonwoven layer 950, can be arranged such that the first surfaces 915 and 955, respectively, are body-facing surfaces, and the second surfaces 920 and 960, respectively, can be arranged as garment-facing surfaces.

While the embodiment shown in FIG. 9 depicts the first nonwoven layer 910 having a first plurality of apertures 925 and the second nonwoven layer 950 with a second plurality of apertures 965, these are optional. For example, embodiments are contemplated where the first nonwoven layer 910 comprises the first plurality of apertures 925 while the second nonwoven layer 950 does not comprise apertures. As another example, the second nonwoven layer 950 may comprise the second plurality of apertures 965 while the first nonwoven layer 910 does not comprise apertures. Additional embodiments are contemplated where both the first nonwoven layer 910 and the second nonwoven layer 950 are sans apertures.

As shown, in some embodiments, the first surface 955 of the second nonwoven layer 950 may comprise a second plurality of discontinuities 975. The second plurality of discontinuities 975 are formed when localized areas of constituent fibers of the second nonwoven layer 950 are urged in the negative Z-direction such that these constituent fibers are disposed subjacent to the second surface 960 of the second nonwoven layer 950. The disposition of the constituent fibers, may, in some embodiments, form a cap 930. The second nonwoven layer 950 may comprise a plurality of caps 930 extending below the second surface 960. Each of the plurality of caps 930 can partially overlie at least one of the second plurality of discontinuities 975. For example, a first cap at least partially overlies a first discontinuity, and a second cap at least partially overlies a second discontinuity and so on.

Similarly, in some embodiments, the first surface 915 of the first nonwoven layer 910 may comprise a first plurality of discontinuities 935. The first plurality of discontinuities 935 can be formed when localized areas of constituent fibers of the first nonwoven layer 910 are urged in the negative Z-direction such that these constituent fibers are disposed subjacent to the second side 920 of the first nonwoven layer 910. This negative Z-direction urging also forces these constituent fibers to extend through the second plurality of discontinuities 975 in the first surface 955 of the second nonwoven layer 950. The extension of the constituent fibers of the first nonwoven layer 910 forms tufts 970.

Tufts 970 extend through at least a portion of the second plurality of discontinuities 975 in the second nonwoven layer 950. Tufts 970 may be configured similarly as described with regard to tufts 270 (shown in FIGS. 2A-2C and 3-4).

Additionally, embodiments are contemplated where the nonwoven web comprises a single nonwoven layer which is provided with an additive. The additive, similar to the embodiments above, can be provided to the nonwoven as part of the master batch or may be applied post fiber production via spraying, slot coating or the like. The single nonwoven layer may be subjected to processing as described herein. For example, the single nonwoven layer may have a portion of its fibers urged in a Z-direction and/or urged in a negative Z-direction. In conjunction with the Z-direction urging and/or negative Z-direction urging, or independently therefrom, the single nonwoven layer may also comprise a plurality of apertures. The single nonwoven layer may comprise multiple nonwoven substrates as described hereafter.

Nonwoven Web Processing

Figure 10:
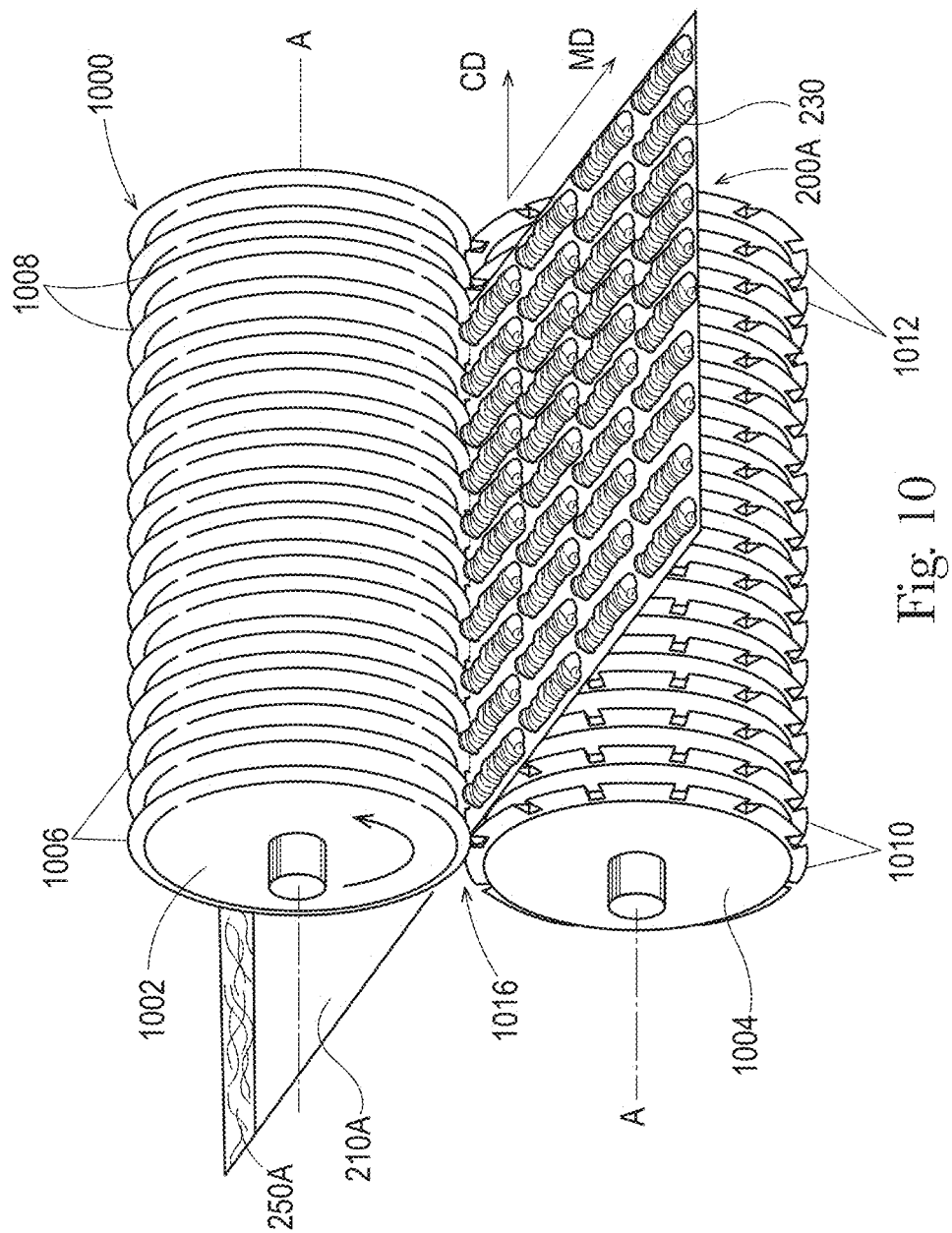
FIG. 10 is a perspective view showing an apparatus for producing some of the nonwoven webs of the present invention.

Depending on the orientations of caps and tufts described heretofore, processing of nonwoven webs of the present invention can vary. Referring to FIG. 10, there is shown an apparatus 1000 and method for producing the nonwoven webs of the present invention. The apparatus 1000 comprises a pair of intermeshing rolls 1002 and 1004, each rotating about an axis A—the axes A being parallel and in the same plane. Roll 1002 comprises a plurality of ridges 1006 and corresponding grooves 1008 which extend unbroken about the entire circumference of roll 1002.

Roll 1004 is similar to roll 1002, but rather than having ridges that extend unbroken about the entire circumference, roll 1004 comprises a plurality of rows of circumferentially-extending ridges that have been modified to be rows of circumferentially-spaced teeth 1010 that extend in spaced relationship about at least a portion of roll 1004. The individual rows of teeth 1010 of roll 1004 are separated by corresponding grooves 1012. In operation, rolls 1002 and 1004 intermesh such that the ridges 1006 of roll 1002 extend into the grooves 1012 of roll 1004 and the teeth 1010 of roll 1004 extend into the grooves 1008 of roll 1002. A nip 1016 is formed between the counter-rotating intermeshing rolls 1002 and 1004. Both or either of rolls 1002 and 1004 can be heated by means known in the art such as by using hot oil filled rollers or electrically-heated rollers.

The apparatus 1000 is shown in a configuration having one patterned roll, e.g., roll 1004, and one non-patterned grooved roll 1002. However, in certain embodiments it may be preferable to use two patterned rolls similar to roll 1004 having either the same or differing patterns, in the same or different corresponding regions of the respective rolls. Such an apparatus can produce webs with tufts protruding from both sides of the nonwoven web.

Nonwoven webs of the present invention can be made by mechanically deforming the first nonwoven layer 210A and the second nonwoven layer 250A that can each be described as generally planar and two dimensional prior to processing by the apparatus shown in FIG. 10. By "planar" and "two dimensional" is meant simply that the webs start the process in a generally flat condition relative to the finished nonwoven web 200A that has distinct, out-of-plane, Z-direction three-dimensionality due to the formation of tufts 270 and/or caps 230. "Planar" and "two-dimensional" are not meant to imply any particular flatness, smoothness or dimensionality. Additionally, nonwoven web 700 (shown in FIG. 7) can be processed as described above.

The nonwoven webs 800 and 900 (shown in FIGS. 8 and 9, respectively) can be processed as described above with some variation described hereafter. For example, in order to accomplish the negative Z-direction urging as described herein, the nonwoven layers may be provided to the apparatus 1000 such that the second nonwoven layer 850 or 950 is disposed superjacent to the first nonwoven layer 810 or 910. However, flipping the resultant nonwoven web at rapid production speeds for processing is difficult to manage and would introduce much complexity into the production of such nonwoven webs. In some embodiments, particularly for those where the desired resultant nonwoven web is as described with regard to nonwoven webs 800 and 900, the rolls 1002 and 1004 of apparatus 1000 can be inverted. For example, the patterned roll 1004 may be positioned superjacent to the non-patterned grooved roll 1002.

The number, spacing, and dimensions of tufts and/or caps can be varied to give varying texture to nonwoven webs of the present invention. For example, if tufts and/or caps are sufficiently closely spaced the resultant nonwoven web can have a terry cloth-like feel. Alternatively, tufts and/or caps can be arranged in patterns such as lines or filled shapes to create portions of a web having greater texture, softness, bulk, absorbency or visual design appeal. For example, when tufts and/or caps are arranged in a pattern of a line or lines, the tufts and/or caps can have the appearance of stitching. Likewise, the size dimensions, such as the height, length and width of individual tufts can be varied.

Single tufts and/or caps can be as long as about 3 cm in length and can be made alone or dispersed among tufts and/or caps of various sizes. In some embodiments, the tufts and/or caps may have a length ranging from about 1 mm to about 10 mm. In some embodiments, the tufts and/or caps may have a length ranging from about 2 mm to about 8 mm; from about 3 mm to about 7 mm, or any ranges within the values recited or any numbers within the values recited.

Additionally, embodiments are contemplated where a nonwoven web includes a plurality of tufts and/or caps which are configured differently. For example, a nonwoven web of the present invention may comprise a tuft 270 and a cap 230 (shown in FIGS. 2A-2C) in a first area of the nonwoven web and may comprise a tuft 770 (shown in FIG. 7) in a second area of the nonwoven web. In other embodiments, a nonwoven web may comprise a tuft 770 (shown in FIG. 7) in a first area of a nonwoven web and may comprise a tuft 970 and a cap 930 (shown in FIG. 9) in a second area of the nonwoven web. In other embodiments, a nonwoven web may comprise a tuft 770 (shown in FIG. 7) in a first area of the nonwoven web and a tuft 870 (shown in FIG. 8) in a second area of the nonwoven web. In other embodiments, a nonwoven web may comprise a tuft 270 and a cap 230 (shown in FIGS. 2A-2C) in a first area of the nonwoven web and a tuft 870 (shown in FIG. 8) in a second area of the nonwoven web. In some embodiments, a nonwoven web may comprise a tuft 270 and a cap 230 (shown in FIGS. 2A-2C) in a first area of the nonwoven web and a tuft 970 and a cap 930 (shown in FIG. 9) in a second area of the nonwoven web. Still in other embodiments, a nonwoven web may comprise a tuft 970 and a cap 930 (shown in FIG. 9) in a first area of the nonwoven web and may comprise a tuft 870 (shown in FIG. 8) in a second area of the nonwoven web. Nonwoven webs of the present invention may utilize any and all combinations of the tufts and/or caps described with regard to FIGS. 2A-2C, 7, 8, and 9) in accordance with the foregoing embodiments, e.g. first area with first set of tufts and/or caps, second area with second set of tufts and/or caps, third area with third set of tufts and/or caps, and so on, wherein each of the first, second and third sets of tufts and/or caps are different.

While the first nonwoven layer and the second nonwoven layer are referred to as 210A and 250A, it should be understood that any of the first nonwoven layers and second nonwoven layers described herein may be processed similarly. The first nonwoven layer 210A and the second nonwoven layer 250A are provided either directly from their respective web making processes or indirectly from supply rolls (neither shown) and moved in the machine direction to the nip 1016 of counter-rotating intermeshing rolls 1002 and 1004. The first nonwoven layer 210A and the second nonwoven layer 250A are preferably held in a sufficient web tension so as to enter the nip 1016 in a generally flattened condition by means well known in the art of web handling. As each of the first nonwoven layer 210A and the second nonwoven layer 250A goes through the nip 1016, the teeth 1010 of roll 1004—which are intermeshed with grooves 1008 of roll 1002—simultaneously urge fibers of the first nonwoven layer 210A out of the plane of the first nonwoven layer 210A thereby forming caps 230 and urge fibers of the second nonwoven layer 250A out of the plane of the second nonwoven layer 250A and through the plane of the first nonwoven layer 210A to form tufts 270.

The number, spacing, and size of tufts 270 and/or caps 230 (shown in FIGS. 3 and 4) can be varied by changing the number, spacing, and size of teeth 1010 and making corresponding dimensional changes as necessary to roll 1004 and/or roll 1002. This variation, together with the variation possible in first nonwoven layer 210A and the second nonwoven layer 250A permits many varied nonwoven webs 200A to be made for many purposes. The size of teeth as well as additional details regarding processing of nonwovens and laminates comprising nonwovens can be found in U.S. Pat. Nos. 7,410,683; 7,789,994; 7,838,099; 8,440,286; and 8,697,218.

As stated previously, the first nonwoven layer and the second nonwoven layer, as described herein, may be provided as discrete layers. For example, embodiments are contemplated where the first nonwoven layer is derived from a first supply roll having a first specific fiber makeup while the second nonwoven layer is derived from a second supply roll having a second specific fiber makeup. In some embodiments, the fiber makeup between the first supply roll and the second supply roll can be different as described below.

Embodiments are contemplated where the first nonwoven layer and the second nonwoven layer are both spunbonded nonwoven materials. In some embodiments, the first nonwoven and the second nonwoven are produced by different spin beams on a single spunbond nonwoven manufacturing line. As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 8 and 40 microns. For example, the first nonwoven layer may be produced by a first spin beam while the second nonwoven layer is produced by a second spin beam.

In some embodiments, the first nonwoven layer and/or the second nonwoven layer may comprise meltblown nonwoven materials. In some embodiments, the first nonwoven layer and/or the second nonwoven layer may comprise finer fibers, including fibers with average diameters less than one micron or 1000 nanometers (an "N-fiber"), may comprise melt fibrillation, advanced meltblowing technology, or electrospinning. Advanced melt-blowing technology is described, for example, in U.S. Pat. No. 4,818,464 to Lau, U.S. Pat. No. 5,114,631 to Nyssen et al., U.S. Pat. No. 5,620,785 to Watt et al., and U.S. Pat. No. 7,501,085 to Bodaghi et al. Melt film fibrillation technology, as example of melt fibrillation, is a general class of making fibers defined in that one or more polymers are molten and are extruded into many possible configurations (e.g., hollow tubes of films, sheets of films, co-extrusion, homogeneous or bi-component films or filaments) and then fibrillated or fiberized into filaments. Examples of such processes are described in U.S. Pat. No. 4,536,361 to Torobin, U.S. Pat. No. 6,110,588 to Perez et al., U.S. Pat. No. 7,666,343 to Johnson et al., U.S. Pat. No. 6,800,226 to Gerking. Electrospinning processes useful to make fine fibers are described in U.S. Pat. No. 1,975,504 to Formhals et al., U.S. Pat. No. 7,585,437, to Jirsak et al., U.S. Pat. No. 6,713,011 to Chu et al., U.S. Pat. No. 8,257,641 to Qi et al.; and also in "Electrospinning", by A. Greiner and J. Wendorff, in *Angew. Chem. Int. Ed.*, 2007, 46(30), 5670-5703.

In some embodiments, the first nonwoven layer and/or the second nonwoven layer may comprise spunlaid or spunbond nonwoven materials. The spunlaid or spunbond fibers typically have an average diameter in the range of about 8 microns to about 40 microns, or a fiber titer in the range from 0.5 to 10 denier. The meltblown fibers have a diameter of typically in the range from 0.5 microns to 10 microns on average, or 0.001 denier to 0.5 denier, and range from about 0.1 microns to over 10 microns. Fine fibers range in average or median diameter from 0.1 microns to 2 microns, and some fine fibers have a number-average diameter of less than about 1 micron, a mass-average diameter of less than about 1.5 microns, and a ratio of the mass-average diameter to the number-average diameter less than about 2.

Dry-Laid and Wet-Laid Nonwoven Substrates

In addition to nonwoven substrates made from the fiber spinning technologies of molten materials, the first nonwoven layer and/or the second nonwoven layer may be made by other means from pre-formed fibers (including natural fibers), such as by drylaid or wetlaid technologies. Drylaid technologies include carding and airlaying. These technologies may be combined with each other, e.g., drylaid with meltspun, to form multi-layer, functional nonwoven substrates.

The carding process uses fibers cut into discrete lengths called staple fiber. The type of fiber and the desired end product properties determine the fiber length and denier. Typical staple fibers have a length in the range of 20 mm to 200 mm and a linear density in the range of 1 dpf to 50 dpf (denier per fiber), though staple fibers beyond this range have also been used for carding. The carding technology processes these staple fibers into a formed substrate. Staple fibers are typically sold in compressed bales that need to be opened to make uniform nonwoven substrates. This opening process may be done through a combination of bale opening, coarse opening, fine opening, or by a similar process. Staple fibers are often blended in order to mix different fiber types and/or to improve uniformity. Fibers may be blended by blending fiber hoppers, bale openers, blending boxes, or by similar methods. The opened and blended fibers are transported to a chute that deposits the fibers across the width of the card and with a density as uniform as practical in order to make a nonwoven substrate with the desired basis weight uniformity. The card contains a series of parallel rollers and/or fixed plates that are covered with metallic clothing, rigid saw-toothed wires with specific geometry that staple fibers are processed between. Carding takes place when fiber tufts transport between the tangent points of two surfaces that have a differential surface speed and opposing angle directions on the metallic clothing. Cards may have a single main cylinder to card with or multiple cylinders. Cards may have a single doffer or multiple doffers to remove the carded fibers and the cards may contain randomizing rollers or condenser rollers to reduce the highly isotropic orientation of the individual fibers in the web. The carding process may contain a single card or multiple cards in line with one another, where the fibers of a subsequent card are deposited on top of the fibers from a preceding card and thus can form multiple layers, e.g., of different fiber compositions. The orientation of these cards may be parallel to the downstream operation or perpendicular to the downstream operation by means of turning or cross-lapping.

The airlaid process also uses fibers of discrete length, though these fibers are often shorter than the staple fibers used for carding. The length of fibers used in airlaying typically ranges from 2 mm to 20 mm, though lengths beyond this range may also be used. Particles may also be deposited into the fibrous structure during the airlaying process. Some fibers for airlaying may be prepared similarly as for carding, i.e., opening and blending as described above. Other fibers, such as pulp, may use mills, such as hammer mills or disc mills, to individualize the fibers. The various fibers may be blended to improve the uniformity of properties of the finished nonwoven substrate. The airlaying forming device combines external air and the fibers and/or particles so that the fibers and/or particles are entrained in the airsteam. After entrainment, the fibers and/or particles are collected as a loose web upon a moving foraminous surface, such as a wire mesh conveyor belt, for example. The airlaying process may contain a single airlaying forming device or multiple airlaying forming devices in line with one another, where the fibers and/or particles of the subsequent airlaying forming device are deposited on top of the fibers and/or particles from a preceding airlaying forming device, thereby allowing manufacture of a multi-layered nonwoven substrate.

Wet-laid nonwovens are made with a modified papermaking process and typically use fibers in the range of 2 mm to 20 mm, though lengths beyond this range have also been used. Some fibers for wetlaying may be prepared similarly as for carding, i.e., opening and blending as described above. Other fibers, such as pulp, may use mills, such as hammer mills or disc mills, to individualize the fibers. The fibers are suspended in water, possibly with other additives like bonding agents, and this slurry is typically added to a headbox from where it flows onto a wetlaid forming device to create a sheet of material. After initial water removal, the web is bonded and dried.

Spunlace nonwovens are typically carded and hydroentangled. The fibers of the spunlace nonwoven are first carded. In order to provide the carded fibers with integrity in the Z-direction and in CD, the carded fibers are then subjected to hydroentangling. Instead of carded nonwovens, spunlace nonwovens may be air-laid or wet-laid and subsequently hydroentangled.

Embodiments are contemplated where the first nonwoven layer and/or the second nonwoven layer comprise a plurality of constituent nonwoven substrates. For the examples below, spunbonded shall be referred to with an "S"; meltblown shall be referred to with an "M"; spunlace shall be referred to with an "SL"; carded shall be referred to with a "C"; and fine fiber layers shall be referred to with an "N". The first nonwoven layer and/or the second nonwoven layer may comprise an S first substrate and an M second substrate. Additional substrates may be added for example, an SMS structure may be created. In other examples, the constituent substrates of the first nonwoven layer and/or the second nonwoven layer may comprise an S and a C substrate; an S and SL substrates; an SNMS substrates or any combination thereof. In some embodiments, the first nonwoven layer and/or the second nonwoven layer may comprise a spunbond fine fiber laminate, "SNL".

The constituent substrates of the first nonwoven layer and/or the second nonwoven layer may be provided with structural integrity via a variety of different processes. Some examples include thermal point bonding, air through bonding, hydroentangling, and needlepunching each of which is well known in the art. Similarly, the attachment of the first nonwoven layer to the second nonwoven layer may be achieved by a variety of different processes. Examples of such processes are discussed hereafter.

Embodiments are contemplated where the constituent substrates of the first nonwoven layer and the second nonwoven layer are subjected to similar attachment processes. For example, the constituent substrates of the first nonwoven layer and the second nonwoven layer may each be subjected to a hydroentangling process, a through air bonding process, a needlepunching process, or a thermal bonding process. In such embodiments, the attachment processes for the first nonwoven and/or the second nonwoven may be different. For example, the constituent substrates of the first nonwoven layer may be subjected to a first hydroentangling process while the constituent substrates of the second nonwoven layer are subjected to a second hydroentangling process. The first hydroentangling process, in some embodiments, may provide a higher degree of structural integrity in the first nonwoven layer versus that provided to the second nonwoven layer via the second hydroentangling process. Alternatively, in some embodiments, the first hydroentangling process may provide a lesser degree of structural integrity in the first nonwoven layer versus that provided to the second nonwoven layer via the second hydroentangling process. Similar embodiments are contemplated with regard to through air bonding, needlepunching, and thermal point bonding.

Additionally, embodiments are contemplated where the constituent substrates of the first nonwoven layer and the second nonwoven layer are subjected to disparate forming or bonding processes. For example, the constituent substrates of the first nonwoven layer may be subjected to a hydroentangling process while the constituent substrates of the first nonwoven layer are subjected to a through air bonding process. Other examples include subjecting one of the first nonwoven layer or the second nonwoven layer to hydroentangling and the other nonwoven layer to needlepunching, through air bonding, or thermal point bonding. Another example includes subjecting one of the first nonwoven layer or the second nonwoven layer to needlepunching and the other nonwoven layer to through air bonding or thermal point bonding. Yet another example includes subjecting one of the first nonwoven layer or the second nonwoven layer to through air bonding and the other to thermal point bonding. Embodiments are contemplated where the forming or bonding process of the first nonwoven layer provides a higher degree of structural integrity than that provided to the second nonwoven layer. Alternatively, embodiments are contemplated where the forming or bonding process of the first nonwoven layer provides a lesser degree of structural integrity than that provided to the second nonwoven layer.

It can be appreciated that in some embodiments, suitable first and second nonwoven layers should comprise fibers capable of experiencing sufficient plastic deformation and tensile elongation, or are capable of sufficient fiber mobility, such that looped fibers 408 (shown in FIGS. 3 and 4) are formed. However, it is recognized that a certain percentage of fibers urged out of the plane of the first surface of second nonwoven layer will not form a loop, but instead will break and form loose ends. Such fibers are referred to herein as "loose" fibers or non-looped fibers (i.e. loose fiber ends) 418 (shown in FIGS. 3 and 4).

In some embodiments, most or all of the fibers of tufts can be non-looped fibers. Non-looped fibers can also be the result of forming tufts from nonwoven webs consisting of, or containing, cut staple fibers. In such a case, some number of the staple fiber ends may protrude into the tuft, depending upon such things as the number of staple fibers in the web, the staple fiber cut length, and the height of the tufts. In some instances, it may be desired to use a blend of fibers of different lengths in a precursor web or fibers of different lengths in different layers. This may be able to selectively separate the longer fibers from the shorter fibers. The longer fibers may predominately form the tuft while the shorter fibers predominately remain in the portion of the web not forming the tuft. A mixture of fiber lengths can include fibers of approximately 2 to 8 centimeters for the longer fibers and less than about 1 centimeter for the shorter fibers.

Regarding the nonwoven webs 200A, 200B, and 200C (shown in FIGS. 2A-2C), for those embodiments where the nonwoven web is utilized as a topsheet for a disposable absorbent article, it may be desirable to increase the likelihood of the occurrence of non-looped fibers 418 in the caps. The increase of non-looped fibers 418 in the caps can increase the comfort to the wearer of the absorbent article. Accordingly, shorter fibers may be utilized for the first nonwoven layer or in those areas of the first nonwoven layer that will urged into caps than those of the second nonwoven layer. Similarly, in some embodiments, the fibers of the first nonwoven layer may be more capable of experiencing more plastic deformation before fracturing than the fibers of the second nonwoven layer. In some embodiments, a combination of the above approaches may be utilized with regard to the constituent fibers of the first nonwoven layer versus the constituent fibers of the second nonwoven layer.

Similarly, with regard to FIG. 7, as the tuft 770 may form a portion of the user facing surface of a disposable absorbent article, appropriate selection of fibers for the second nonwoven layer 750 may be desirable to increase the likelihood of non-looped fibers 418 in the tufts 770. Additionally, non-looped fibers 418 may be beneficial for the nonwoven webs 800 and 900 (shown in FIGS. 8 and 9). For example, since the tufts 870 and 970 are oriented in the negative Z-direction, a large number of non-looped fibers 418 in the first nonwoven layer 810 or 910 may increase the permeability of the first nonwoven layer 810 or 910. This increase in permeability may reduce the need for apertures or in some embodiments, fewer apertures may be required for adequate liquid transfer to subjacent layers of a disposable absorbent article.

The first nonwoven layer and the second nonwoven layer, as discussed previously, comprise, in some embodiments, a plurality of randomly oriented fibers. The plurality of randomly oriented fibers of the first nonwoven layer and/or the second nonwoven layer may comprise any suitable thermoplastic polymer.

Suitable thermoplastic polymers, as used in the disclosed compositions, are polymers that melt and then, upon cooling, crystallize or harden, but can be re-melted upon further heating. Suitable thermoplastic polymers used herein have a melting temperature (also referred to as solidification temperature) from about 60° C. to about 300° C., from about 80° C. to about 250° C., or from 100° C. to 215° C. And, the molecular weight of the thermoplastic polymer should be sufficiently high to enable entanglement between polymer molecules and yet low enough to be melt spinnable.

In some embodiments, the thermoplastic polymers can be derived from renewable resources or from fossil minerals and oils. The thermoplastic polymers derived from renewable resources are bio-based, for example such as bio produced ethylene and propylene monomers used in the production polypropylene and polyethylene. These material properties are essentially identical to fossil based product equivalents, except for the presence of carbon-14 in the thermoplastic polymer. Renewable and fossil based thermoplastic polymers can be combined together in the present invention in any ratio, depending on cost and availability.

Recycled thermoplastic polymers can also be used, alone or in combination with renewable and/or fossil derived thermoplastic polymers. The recycled thermoplastic polymers can be pre-conditioned to remove any unwanted contaminants prior to compounding or they can be used during the compounding and extrusion process, as well as simply left in the admixture. These contaminants can include trace amounts of other polymers, pulp, pigments, inorganic compounds, organic compounds and other additives typically found in processed polymeric compositions. The contaminants should not negatively impact the final performance properties of the admixture, for example, causing spinning breaks during a fiber spinning process.

Some suitable examples of thermoplastic polymers include polyolefins, polyesters, polyamides, copolymers thereof, and combinations thereof. In some embodiments, the thermoplastic polymer can be selected from the group consisting of polypropylene, polyethylene, polypropylene co-polymer, polyethylene co-polymer, polyethylene terephthalate, polybutylene terephthalate, polylactic acid, polyhydroxyalkanoates, polyamide-6, polyamide-6,6, and combinations thereof. The polymer can be polypropylene based, polyethylene based, polyhydroxyalkanoate based polymer systems, copolymers and combinations thereof.

In some embodiments, the thermoplastic polymers include polyolefins such as polyethylene or copolymers thereof, including low density, high density, linear low density, or ultra low density polyethylenes such that the polyethylene density ranges between 0.90 grams per cubic centimeter to 0.97 grams per cubic centimeter, between 0.92 and 0.95 grams per cubic centimeter or any values within these ranges or any ranges within these values. The density of the polyethylene may be determined by the amount and type of branching and depends on the polymerization technology and co-monomer type. Polypropylene and/or polypropylene copolymers, including atactic polypropylene; isotactic polypropylene, syndiotactic polypropylene, and combination thereof can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin and may be used in some embodiments.

Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; polyacrylates, polymethacrylates, and their copolymers such as poly(m-ethyl methacrylates). Other nonlimiting examples of polymers include polycarbonates, polyvinyl acetates, poly (oxymethylene), styrene copolymers, polyacrylates, polymethacrylates, poly(methyl methacrylates), polystyrene/methyl methacrylate copolymers, polyetherimides, polysulfones, or combinations thereof. In some embodiments, thermoplastic polymers include polypropylene, polyethylene, polyamides, polyvinyl alcohol, ethylene acrylic acid, polyolefin carboxylic acid copolymers, polyesters, and combinations thereof.

Biodegradable thermoplastic polymers also are contemplated for use herein. Biodegradable materials are susceptible to being assimilated by microorganisms, such as molds, fungi, and bacteria when the biodegradable material is buried in the ground or otherwise contacts the microorganisms (including contact under environmental conditions conducive to the growth of the microorganisms). Suitable biodegradable polymers also include those biodegradable materials which are environmentally-degradable using aerobic or anaerobic digestion procedures, or by virtue of being exposed to environmental elements such as sunlight, rain, moisture, wind, temperature, and the like. The biodegradable thermoplastic polymers can be used individually or as a combination of biodegradable or non-biodegradable polymers. Biodegradable polymers include polyesters containing aliphatic components. Among the polyesters are ester polycondensates containing aliphatic constituents and poly(hydroxycarboxylic) acid. The ester polycondensates include diacids/diol aliphatic polyesters such as polybutylene succinate, polybutylene succinate co-adipate, aliphatic/aromatic polyesters such as terpolymers made of butylenes diol, adipic acid and terephthalic acid. The poly(hydroxycarboxylic) acids include lactic acid based homopolymers and copolymers, polyhydroxybutyrate (PHB), or other polyhydroxyalkanoate homopolymers and copolymers. Such polyhydroxyalkanoates include copolymers of PHB with higher chain length monomers, such as $C_6$-$C_{12}$, and higher, polyhydroxyalkanaotes, such as those disclosed in U.S. Pat. Nos. RE 36,548 and 5,990,271.

An example of a suitable commercially available polylactic acid is NATUREWORKS from Cargill Dow and LACEA from Mitsui Chemical. An example of a suitable commercially available diacid/diol aliphatic polyester is the polybutylene succinate/adipate copolymers sold as BIONOLLE 1000 and BIONOLLE 3000 from the Showa High Polymer Company, Ltd. (Tokyo, Japan). An example of a suitable commercially available aliphatic/aromatic copolyester is the poly(tetramethylene adipate-co-terephthalate) sold as EASTAR BIO Copolyester from Eastman Chemical or ECOFLEX from BASF.

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), Mosten NB425 (a 25 melt flow rate Ziegler-Natta isotactic polypropylene from Unipetrol), Danimer 27510 (a polyhydroxyalkanoate polypropylene from Danimer Scientific LLC), Dow Aspun 6811A (a 27 melt index polyethylene polypropylene copolymer from Dow Chemical), and Eastman 9921 (a polyester terephthalic homopolymer with a nominally 0.81 intrinsic viscosity from Eastman Chemical).

Polypropylene can have a melt flow index of greater than 5 g/10 min, as measured by ASTM D-1238, used for measuring polypropylene. Other contemplated melt flow indices for polypropylene include greater than 10 g/10 min, greater than 20 g/10 min, or about 5 g/10 min to about 50 g/10 min.

The thermoplastic polymer component can be a single polymer species as described above or a blend of two or more thermoplastic polymers as described above.

In some embodiments, the first nonwoven layer and second nonwoven layer may be fibrous woven or nonwoven webs comprising elastic or elastomeric fibers. Elastic or elastomeric fibers can be stretched at least about 50% and return to within 10% of their original dimension. Tufts can be formed from elastic fibers if the fibers are simply displaced due to the mobility of the fiber within the nonwoven, or if the fibers are stretched beyond their elastic limit and are plastically deformed.

In some embodiments, the constituent fibers of the first nonwoven layer can be comprised of polymers such as polypropylene and blends of polypropylene and polyethylene. In some embodiments, the second nonwoven layer may comprise fibers selected from polypropylene, polypropylene/polyethylene blends, and polyethylene/polyethylene teraphthalate blends. In some embodiments, the second nonwoven layer may comprise fibers selected from cellulose rayon, cotton, other hydrophilic fiber materials, or combinations thereof. The fibers can also comprise a super absorbent material such as polyacrylate or any combination of suitable materials.

In one embodiment, the constituent fibers of the first nonwoven layer are selected such that the first nonwoven layer is hydrophobic, and the constituent fibers of the second nonwoven layer are selected such that the second nonwoven layer is hydrophilic. For example, in some embodiments, the fibers of the first nonwoven layer may comprise polypropylene, while the fibers of the second nonwoven layer comprise rayon. In one specific embodiment, the fibers of the second nonwoven layer comprise thermoplastic fibers that are treated with a topical surfactant or comprise a hydrophilic melt additive that blooms to the surface in order to render the second nonwoven layer hydrophilic. In such embodiments, the second nonwoven layer may comprise the fibers as mentioned previously for the first nonwoven layer. Some examples of suitable hydrophilic treatments include Silastol PH26 available from Schill & Seilacher or Stantex S6327 available from Pulcra Chemicals GmbH each of which is a post fiber production hydrophilic treatment. Suitable hydrophilic melt additives are available from Polyvel, Inc. sold under the trade name VW351 wetting agent and from Goulston Technologies Inc. under the trade name Hydrosorb 1001. Other suitable hydrophilic additives are available from Techmer PM, LLC under the trade names PPM15560, TPM12713, PPM19913, PPM19441, PPM 19914 (for polypropylene) and PPM19668 (for polyethylene). Additional examples of hydrophilic additives whether as a master batch or post fiber production are described in U.S. Patent Application No. 2012/0077886; U.S. Pat. Nos. 5,969,026; and 4,578,414.

The fibers of the nonwoven layer and/or the second nonwoven layer can be monocomponent, bi-component, and/or bi-constituent, round or non-round (e.g., capillary channel fibers), and can have major cross-sectional dimensions (e.g., diameter for round fibers) ranging from 0.1-500 microns. For example, one type of fibers suitable for the nonwoven web includes nanofibers. Nanofibers are described as fibers having a mean diameter of less than 1 micron. Nanofibers can comprise all of the fibers in a nonwoven web or a portion of the fibers in a nonwoven web. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers can range from about 0.1 denier to about 100 denier.

Embodiments are contemplated where the first plurality of fibers and/or the second plurality of fibers comprise agents in addition to their constituent chemistry. For example, suitable additives include additives for coloration, antistatic properties, lubrication, hydrophilicity, and the like and combinations thereof. These additives, for example titanium dioxide for coloration, are generally present in an amount less than about 5 weight percent and more typically about 2 weight percent.

As used herein, the term "monocomponent" fiber refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fibers" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which can be used in the first nonwoven layer include polyethylene/polypropylene side-by-side bi-component fibers. Another example, is a polypropylene/polyethylene bi-component fiber where the polyethylene is configured as a sheath and the polypropylene is configured as a core within the sheath. Still another example, is a polypropylene/polypropylene bi-component fiber where two different propylene polymers are configured in a side-by-side configuration. Additionally, embodiments are contemplated where the constituent fibers of the first nonwoven layer are crimped.

As used herein, the term "bi-constituent fibers" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers.

As used herein, the term "non-round fibers" describes fibers having a non-round cross-section, and includes "shaped fibers" and "capillary channel fibers." Such fibers can be solid or hollow, and they can be tri-lobal, delta-shaped, and can be fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, TN. T-401 fiber is a polyethylene terephthalate (PET polyester).

In some embodiments, the first nonwoven layer and/or second nonwoven layer is a nonwoven web in which there are minimal fiber-to-fiber bonds. For example, the first nonwoven layer and/or second nonwoven layer can be a nonwoven web having a pattern of discrete thermal point bonds, as is commonly known in the art for nonwoven webs. In general, however, it is desirable to minimize the number of bond points and maximize the spacing so as to allow for maximum fiber mobility and dislocation during formation of tufts and/or caps. In general, using fibers having relatively high diameters, and/or relatively high extension to break, and/or relatively high fiber mobility, might result in better and more distinctly formed tufts and/or caps. In another embodiment, the first nonwoven layer and/or the second nonwoven layer can be through air bonded nonwoven material.

Although nonwoven webs of the present invention disclosed herein are described as a two layer web made from two nonwoven layers, it is not necessary that it be limited to two layers. For example, a three-layer or more laminate can be made from three nonwoven layer. Embodiments are contemplated where there are three or more layers of nonwoven material.

The first nonwoven layer and the second nonwoven layer of the nonwoven webs 200A, 200B, 200C, 700, 800, and 900, (shown in FIGS. 2A-2C and 7-9, respectively), can be held in a face-to-face laminated relationship by virtue of the "locking" effect of the tufts that extend through the discrepancies in first nonwoven layer or second nonwoven layer as described herein. In some embodiments (including the nonwoven webs 100A and 100B shown in FIGS. 1A and 1B) it may be desirable to use adhesives or thermal bonding or other bonding means, depending on the end use application of the nonwoven web. Additionally, it may be desirable to apply adhesive to at least a portion of one of the first nonwoven layer and/or the second nonwoven layer. For example, in some embodiments adhesive, chemical bonding, resin or powder bonding, or thermal bonding between layers can be selectively applied to certain regions or all of the nonwoven layers. In the case of adhesive application, for example, adhesive can be applied in a continuous manner, such as by slot coating, or in a discontinuous manner, such as by spraying, extruding, and the like. Discontinuous application of adhesive can be in the form of stripes, bands, droplets, and the like. Any suitable adhesive may be utilized.

In one embodiment, after tufts and/or caps are formed, the nonwoven material (the constituents of the first nonwoven layer, and/or the constituents of the second nonwoven layer, and/or the resultant nonwoven web that is a combination of the first nonwoven layer and the second nonwoven layer) may be attached as described in U.S. Pat. No. 7,682,686. For example, the first nonwoven layer and the second nonwoven layer may be attached adjacent the cap base 471 (shown in FIG. 4). As another example, the first nonwoven layer and the second nonwoven layer may be attached adjacent an apex of the cap. In yet another example, the first nonwoven layer and the second nonwoven layer may be attached adjacent the cap base 471 and adjacent the apex of the cap. Regarding the above embodiments, attachment may be provided for each cap present or provided to less than the totality of caps.

Any suitable process for aperturing the first nonwoven layer and/or the second nonwoven layer may be utilized. However, the aperturing process selected should not preclude the liquid communication relationship between the first nonwoven layer and the second nonwoven layer. Some suitable aperturing processes for the first nonwoven layer and/or the second nonwoven layer are described in U.S. Pat. Nos. 5,628,097; 5,916,661; 5,658,639; 6,884,494; and 7,037,569. Additional suitable processes are described in U.S. Pat. Nos. 8,679,391; 8,241,543; and 8,158,043. Additionally, in some embodiments, aperturing may be achieved via a spunlacing process. For example, the first nonwoven layer and/or the second nonwoven layer may transported to a hydroentangling apparatus. A carrier transporting the first and/or second nonwoven layer, may comprise large openings which allow fluid to pass therethrough. During the hydroentangling process, the constituent fibers of the first and/or second nonwoven layers may be moved via the water jets of the hydroentangling and generally mimic the pattern of the carrier. As such, the first and/or second nonwoven layer may comprise apertures which mimic the openings in the carrier.

The aperturing of the first and/or second nonwoven layers may be done separately or contemporaneously where the first nonwoven layer and the second nonwoven layer are configured as a laminate web. The area of each of the individual apertures of the present invention may be about 0.8 mm$^2$ to about 4.0 mm$^2$ or, in some embodiments, from about 1.5 mm$^2$ to about 2.5 mm$^2$, specifically including any values within these ranges or any ranges created thereby. In some embodiments, the overall open area of the first nonwoven layer and/or the second nonwoven layer may be from about 9 percent to about 30 percent, specifically including all values within this range and any ranges created thereby. The percentage open area is defined as a ratio of the sum of the area of apertures divided by the total area of the layer (apertures plus land areas).

It is worth noting that care should be exercised in selecting both the aperture area and overall open area. For example, while larger apertures may facilitate fluid acquisition into lower layers of an absorbent article, larger apertures can create a problem from a rewet standpoint. Additionally, larger aperture sizes can weaken the nonwoven to such an extent as to introduce tearing issues during manufacture or during use by the wearer.

Hydrophobic Additive

As mentioned previously, the first nonwoven layers described herein, comprise a first plurality of substantially randomly oriented fibers. Additionally, the first nonwoven layers described herein may comprise an additive which blooms on a surface of at least a portion of the first plurality of fibers. The additive may be applied on the fibers post production or may be added directly or as master batch to the polymer melt during spinning of the filaments as a melt additive. For those embodiments where the additive is melt blended into the filaments, the additive can bloom to the surface of the fibers and create a film covering a portion of the external surface of the fiber and/or can create fibrils, flakes, particles, and/or other surface features. For those embodiments where the additive is applied to the fibers post production, the additive can form particles, films, flakes, and/or droplets. For those fibers comprising fibrils, the fibrils may extend outwardly, or radially outwardly, from the surface.

While the fibrils extend outwardly from surfaces of individual fibers, the fibrils may also extend to or from (i.e., contact) other fibers within the same layer or a different layer of a nonwoven substrate and/or to fibrils extending from fibers within the same layer or a different layer of the nonwoven substrate. When the fibrils extend between fibers and/or other fibrils, the nonwoven substrate may achieve a greater liquid contact angle for polar and non-polar liquids. A similar effect may be obtained for additives which are applied to the first plurality of fibers post production. Without wishing to be bound by theory, it is believed that the additive, regardless of whether a melt additive or applied post fiber production, changes the surface energy of the constituent fibers. The change in surface energy increases the hydrophobic nature of the constituent fibers and therefore the first nonwoven layer. Additionally, it is believed that the additive, whether a melt additive or applied post fiber production, increases the surface roughness of the constituent fibers which can increase hydrophobicity. It is believed that an increase in hydrophobicity due to surface roughness is achieved by metastable Wenzel and stable Cassie-Baxter non-wetting states.

The additive suitable for the present invention may be any suitable hydrophobic additive. Thus, the additives may increase the hydrophobicity of the fibers upon whose surface they bloom. This can lead to increased low surface tension fluid strikethrough times and higher hydrophobicity for the first nonwoven layer and/or when compared to the second nonwoven layer.

Some examples of suitable additives include fatty alcohols and fatty acid esters. Non-limiting examples of suitable fatty alcohols having from about 12 to about 24 carbon atoms include saturated, un-substituted, monohydric alcohols or combinations thereof, which have a melting point less than about 110° C., preferably from about 45° C. to about 110° C. Specific examples of fatty alcohol carriers for use in the skin care compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol are Stenol 1822 and behenyl alcohol is Lanette 22, both of which are available from the Cognis Corporation located in Cincinnati, Ohio.

Non-limiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

In some embodiments, the additives of the present disclosure, may have a melting point in the range of about 40 degrees C. to about 80 degrees C., about 55 degrees C. to about 75 degrees C., about 60 degrees C. to about 73 degrees C., specifically reciting all one degree C. increments within the specified ranges and all ranges formed therein or thereby. In various embodiments, the additives of the present disclosure may have a melting temperature above 30° C., above 40° C., or above 50° C., but less than 80 degrees C., including all ranges within the values expressed and all numbers within the ranges created by the values expressed.

In some embodiments, the additive may have a hydrophilic/lipophilic balance ("HLB") value of less than about 4. In some embodiments, the HLB value may be greater than about 0 and less than about 4, between about 1 and about 3.5, between about 2 and about 3.3, or any ranges within the values provided or any value within the ranges provided. It is believed that above an HLB value of about 4, the additive will start to take on more surfactant-like hydrophilic properties and would thereby reduce the benefit provided by the highly hydrophobic additive. Namely, as mentioned previously, the hydrophobic additive can provide a masking benefit which makes the disposable absorbent article utilizing the nonwoven web of the present invention appear more "clean" after a liquid insult has occurred.

In some embodiments, the additive may have an IOB (inorganic value/organic value) value of greater than about 0 and less than about 0.4, between about 0.1 and about 0.35, between about 0.2 and 0.33, specifically including all values within these ranges and any ranges created thereby. The IOB value is discussed in additional detail in EP Patent Application Publication No. 2517689.

The additives used, may comprise fatty acid derivatives, such as a fatty acid ester; typically an ester formed from an alcohol with two or more hydroxyl groups and one or more fatty acids having between at least 12 carbon atoms to 22 carbon atoms, or at least 14 carbon atoms, whereby within one ester compound, different fatty acid-derived groups may be present (herein referred to as fatty acid ester).

The fatty acid ester compound may be an ester of an alcohol carrying two or more, or three or more, functional hydroxyl group per alcohol molecule, whereby all of the hydroxyl groups form an ester bond with fatty acids (either the fatty acid or mixtures thereof).

In an embodiment, the alcohol may have three functional hydroxyl groups. It is understood that in a fatty acid ester having more than one ester bond, such as in di- or triglycerides, the fatty acid-derived group may be the same, or they may be two or even three different fatty acids-derived groups. It is further understood that the additive component may comprise a mixture of mono- di- and/or tri-fatty acid ester (e.g. mono- di-, and/or triglyceride) esters with the same fatty-acid derived group per molecule, and/or with different fatty acid-derived groups without exceeding the scope of the invention. Preferred fatty acids in at least one embodiment may range from a C8 fatty acid to a C30 fatty acid; or, in another embodiment range from a C12 fatty acid to a C22 fatty acid. Suitable vegetable fatty acids typically include unsaturated fatty acids. The fatty acid may suitably be selected from the group comprising an arachidec acid, a stearic acid, a palmitic acid, a myristic acid, a myristoleic acid, an oleic acid, a limoleic acid, a linolenic acid, and an arachidonic acid. In another further embodiment, a substantially saturated fatty acid is preferred, particularly when saturation arises as a result of hydrogenation of fatty acid precursor. The fatty acids may range from a C12 fatty acid to a C22 fatty acid as illustrated in [1],

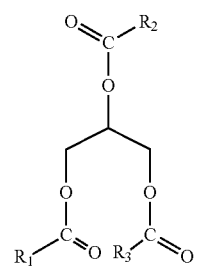

[1]

where R1' R2, and R3 each have a number of carbon atoms ranging from 11 to 21. In at least one other embodiment, the fatty acids may range from a C16 fatty acid to a C20 fatty acid.

In at least one further embodiment, a substantially saturated fatty acid is preferred, particularly when saturation arises as a result of hydrogenation of fatty acid precursor. In at least one further embodiment, a C18 fatty acid, stearic acid, is preferred. An example of the stearic acid-substituted fatty acid is [2-octadecanoyloxy-1-(octadecanoyloxymethyl)ethyl]octadecanoate having a CAS registry number of 555-43-1. It should be understood that the preferred triglyceride ester has an esterified glycerol backbone having no non-hydrogen sub-stitutents on the glycerol backbone.

In an embodiment, the one or more additives may comprise a mono- and/or di-glyceride ester, and/or a triglyceride ester, (with one, two or three fatty acid-derived groups). It should be understood that while [1] illustrates a simple triglyceride in which all three pendent fatty acids may be the same, other embodiments may include a mixed triglyceride in which two or even three different pendent fatty acids are present without exceeding the scope of the invention. It should be further understood that while the triglyceride ester is illustrated in [1] is a single triglyceride ester formulation, the triglyceride ester used in the preparation of the master batch may include a plurality of triglyceride esters having different pendent fatty acid groups and/or one or more derivatives of the fatty acid, without exceeding the scope of the invention. It should be further understood that while the triglyceride ester illustrated in [1] is a monomer, the triglyceride ester used in the preparation of the master batch may include a polymerized triglyceride ester, such as a polymerized, saturated glyceride ester without exceeding the scope of the invention. It should be further understood that the polymerized triglyceride ester may comprise a mixture of polymers having different numbers of monomeric units included in the polymer. For example the polymerized triglyceride ester may include a mixture of monoesters, diesters, and the like.

The fatty acids used to form the ester compounds include fatty acid derivatives for the purpose of the present disclosure. A mono-fatty acid ester, or for example, amonoglyceride, comprises a single fatty acid, e.g., connected a glycerol; a di-fatty acid ester, or e.g., di-glyceride, comprises two fatty acids, e.g., connected to the glycerol; a tri-fatty acid ester, or e.g. tri-glyceride, comprises three fatty acids, e.g., connected to a glycerol. In an embodiment, the additive may comprise at least a triglyceride ester of fatty acids (i.e., the same or different fatty acids).

It should be understood that the triglyceride ester may have an esterified glycerol backbone having no nonhydrogen substituents on the glycerol backbone; however, the glycerol backbone may also comprise other substituents.

In an embodiment, the glycerol backbone of the glycerol ester may only comprise hydrogen. The glyceride esters may also comprise polymerized (e.g., tri) glyceride esters, such as a polymerized, saturated glyceride esters.

In a fatty acid ester having more than one ester bond, such as in di- or tri-glycerides, the fatty acid-derived group may be the same, or they may be two or even three different fatty acids-derived groups.

The additive may comprise a mixture of mono-, di-, and/or tri-fatty acid ester (e.g., mono- di- and/or triglyceride) esters with the same fatty-acid derived group per molecule, and/or with different fatty acid-derived groups.

The fatty acids may originate from vegetable, animal, and/or synthetic sources. Some fatty acids may range from a C8 fatty acid to a C30 fatty acid, or from a C12 fatty acid to a C22 fatty acid. Suitable vegetable fatty acids typically include unsaturated fatty acids such as oleic acid, palmitic acid, linoleic acid, and linolenic acid. The fatty acid may be arachidec, stearic, palmitic, myristic, myristoleic, oleic, limoleic, linolenic, and/or arachidonic acid.

In another embodiment, a substantially saturated fatty acid may be used, particularly when saturation arises as a result of hydrogenation of fatty acid precursor. In an embodiment, a C18 fatty acid, or octadecanoic acid, or more commonly called stearic acid may be used to form an ester bond of the fatty acid ester herein; stearic acid may be derived from animal fat and oils as well as some vegetable oils. The stearic acid may also be prepared by hydrogenation of vegetable oils, such as cottonseed oil. The fatty acid ester herein may comprise fatty acids of mixed hydrogenated vegetable oil, such as one having CAS registration number 68334-28-1.

At least one stearic acid, at least two, or three stearic acids are connected to a glycerol, to form a glycerol tristearate, for the additive herein. In an embodiment, the additive may comprise a glycerol tristearate (CAS No. 555-43-1), also known by such names as tristearin or 1,2,3-Trioctadecanoylglycerol. (In the following, the name glycerol tristearate will be used, and in case of doubt the CAS No., shall be seen as the primary identifier).

In other embodiments, additives with chemical structures similar to glycerol tristearate or tristearin such as triacylglycerols (triglycerides) including but not limited to trimyristin, tripalmitin, trilaurin, trimargarine, and waxes such as distearin, and mixtures of saturated and unsaturated glycerides, such as 1,3-distearoyl-2-oleoylglycerol (SOS) may be utilized. Non-limiting examples additives having molecular and crystallite structures as similar to tristearin include Alkylketene dimers (AKD), inorganic and organic salts of fatty acids (also known as alkyl carboxylic acids) that comprise of alkyl chains that are mostly saturated, and contain between 12 and 22 carbon atoms. Non-limiting examples of salts of fatty acids include zinc stearate, calcium stearate, magnesium stearate, titanium stearate, silver stearate, aluminum di- and tri-stearates, aluminum tripalmitate, aluminum trimyristate, aluminum trilaurate, sorbitan tristearate, sorbitan tripalmitate, sorbitan trimyristate, sorbitan trilaurate, and combinations thereof, which are believed to form flaky and fibrillar lamellar structures on surfaces due to blooming.

In an embodiment, the fatty acid ester of the additive may have a number-averaged molecular weight ranging from 500 to 2000, from 650 to 1200, or from 750 to 1000, specifically reciting all whole integer increments within the above-specified ranges and any ranges formed therein or thereby.

The additive may comprise very little or no halogen atoms; for example, the additive may comprise less than 5 wt. % halogen atoms (by weight of the additive), or less than 1 wt. %, or less than 0.1 wt. % of the additive; the additive may be substantially halogen-free.

In an embodiment, the additive may be or may comprise a lipid ester or glycerol tristearate. In various embodiments, the fibrils may comprise, consist of, or consist essentially of (i.e., 51% to 100%, 51% to 99%, 60% to 99%, 70% to 95%, 75% to 95%, 80% to 95%, specifically including all 0.1% increments within the specified ranges and all ranges formed therein or thereby) of the additive.

Nonlimiting examples of suitable alkyl ethoxylates include $C_{12}$-$C_{22}$ fatty alcohol ethoxylates having an average degree of ethoxylation of from about 2 to about 30. Non-limiting examples of suitable lower alcohols having from about 1 to about 6 carbon atoms include ethanol, isopropanol, butanediol, 1,2,4-butanetriol, 1,2 hexanediol, ether propanol, and mixtures thereof. Non-limiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole), and mixtures thereof.

The master batch added to the composition from which the fibers of the present disclosure are formed may be the master batch disclosed in U.S. Pat. No. 8,026,188 to Mor- In an embodiment, the fibrils may grow out of the fibers post-nonwoven substrate formation under ambient conditions. The fibrils may be noticeable using an SEM after about 6 hours post-nonwoven substrate formation under ambient conditions. Fibril growth may reach a plateau after about 50 hours, 75 hours, 100 hours, 200 hours, or 300 hours post-nonwoven substrate formation under ambient conditions. In some embodiments, fibril growth may continue well beyond 300 hours. The time range of noticeable fibril growth post-nonwoven substrate formation may be in the range of 1 minute to 300 hours, 5 hours to 250 hours, 6 hours to 200 hours, 6 hours to 100 hours, 6 hours to 24 hours, 6 hours to 48 hours, or 6 hours to 72 hours, under ambient conditions, specifically reciting all 1 minute increments within the above specified ranges and all ranges formed therein or thereby. The time to allow full fibril growth post-nonwoven substrate formation may be 12 hours, 24 hours, 48 hours, 60 hours, 72 hours, 100 hours, or 200 hours, for example, under ambient conditions. In some embodiments, fibril growth may occur almost immediately post nonwoven production.

Typical size scale of fibril or flake or other surface structures protruding from surface due to blooming may be of the order of few nanometers to few tens of micrometers. For example, the average length of the bloomed surface structures can range from about 5 nanometers to about 50 micrometers, from about 100 nanometers to about 30 micrometers, or from about 500 nanometers to about 20 micrometers. Preferred average width of the bloomed surface structures can range from about 5 nanometers to about 50 micrometers, from about 100 nanometers to about 20 micrometers, or from about 500 nanometers to about 5 micrometers. Preferred average thickness of the bloomed surface structures would range from about 5 nanometers to about 10 micrometers, more preferably from about 50 nanometers to about 5 micrometers, and most preferably from about 100 nanometers to about 1 micrometers. Preferred average hydraulic diameter, calculated as 4*(Cross-sectional Area)/(Cross-sectional Perimeter) of the bloomed surface structure can range from about 5 nanometers to about 20 micrometers, from about 50 nanometers to about 10 micrometers, or from about 100 nanometers to about 1.5 micrometers. In a specific embodiment, the average hydraulic diameter of a fibril is in the range of from about 100 nanometers to about 800 nanometers. Average separation of the bloomed surface structures from one another can range from about 100 nanometers to about 20 micrometers, from about 500 nanometers to about 10 micrometers, or from about 500 nanometers to about 5 micrometers.

The nonwoven substrates of the present disclosure having at least one layer comprising fibers comprising fibrils may be configured to be softer or harder than, or have the same softness as, conventional nonwoven substrates and/or may have a rougher, smoother, or the same tactile property as compared to conventional nonwoven substrates. The softness, hardness, and/or tactile property of the nonwoven substrates may vary depending on the type and amount of lipid esters present in the composition used to form the fibers and the length of the fibrils, for example. The softness, hardness, and/or texture may also vary depending on where the one or more layers of fibers having fibrils are positioned within a nonwoven substrate.

In an embodiment, the fibrils/droplets may have a different color than the fibers from which they grow. Stated another way, the fibrils may have a first color and the fibers from which they grow may have a second color in non-fibril areas of the fibers. The first color may be different than the second color (e.g., the fibers in non-fibril areas may be white and the fibrils may be blue or the fibers in non-fibril areas may be light blue and the fibrils may be dark blue). This color variation can be accomplished by adding a colorant, such as a pigment or dye to the lipid esters before they are mixed into the composition used to form the fibers. When the additive blooms from the fibers, they can be a different color than the fibers from which they grow, thereby producing a color contrast between the fibrils and the fibers from which they grow. In an embodiment, the first nonwoven layer comprising the fibers comprising the fibrils may appear to change color over a period of time (i.e., the period of time in which the fibrils grow or a portion thereof) due to the contrasting color of the fibrils with respect to the fibers from which they grow. Different layers of fibers may have different colored fibrils and/or fiber therein within the same nonwoven substrate. In an embodiment, the colorant added to the lipid esters may be dissolvable in urine, menses, runny BM, other bodily fluid, or other fluid (e.g., water). In various embodiments, the dissolving colorant in the fibrils may be used as a wetness indicator in an absorbent article, for example.

For those embodiments where the hydrophobic additive is applied post fiber production, the additive may be selectively applied. For example, the additive may be applied in a first area of the nonwoven web and may not be applied in a second area. As another example, the additive may be applied in specific patterns with void spaces to encourage fluid drainage to the second nonwoven layer. The additive may be applied at a basis weight of from about 0.1 gsm to 10 gsm, preferably <1 gsm. The additive may be blended with other melt additive or topical ingredients, for example in a lotion composition. The additive may be applied uniformly throughout the nonwoven material or alternatively be applied in zones or layers or gradients, for example preferentially in the center portion of a topsheet. For those embodiments where bi-component fibers are utilized, the additive may be present at the same level in each of the constituents of the bi-component fiber, may be at different levels with regard to the constituents of the bi-component fiber, or may be preset in one constituent but not the other of a bi-component fiber.

For those embodiments where the hydrophobic additive is provided as a melt additive, e.g. part of the master batch, preferably between 0.5 percent by weight to about 20 percent by weight, preferably less than 10 percent by weight or any range within these values or any value within these ranges.

The additive may be applied to the fibers of the nonwoven web by any suitable process. Some examples include spraying, slot coating, or the like. Other suitable hydrophobic additives are available from Techmer PM, LLC.

Embodiments are contemplated where the first nonwoven layer and/or the second nonwoven layer include compositions in addition to the additive. Some examples include lotions, skin care actives, odor absorbing or inhibiting or masking, fragrances, pigments, dyes, agents affecting the coefficient of friction, antimicrobial/antibacterial agents, the like or combinations thereof.

EXAMPLES

Figure 11:
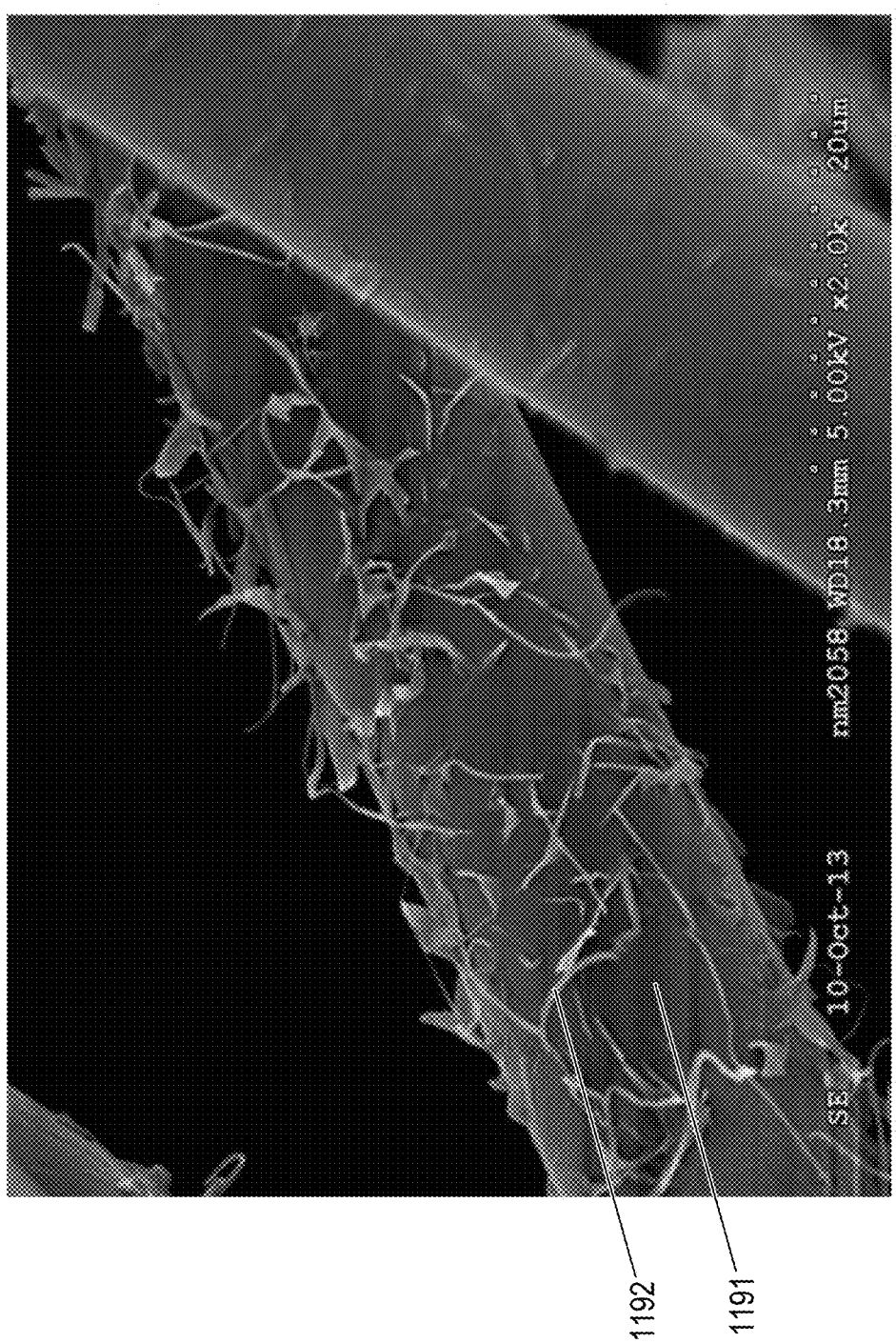
FIG. 11 is a scanning electron micrograph ("SEM") photo showing a nonwoven fiber with additive that has bloomed on the surface of the fiber.

FIG. 11 is an SEM photo of a polypropylene fiber with glycerol tristearate additive added to the fibers as a master batch (8 wt % Techmer PPM17000 High Load Hydrophobic). The masterbatch comprised about 60 percent by weight polypropylene and about 40 percent by weight glycerol tristearate. As shown the fiber 1191 comprise a plurality of fibrils 1192 extending from the surface thereof.

Figure 12:
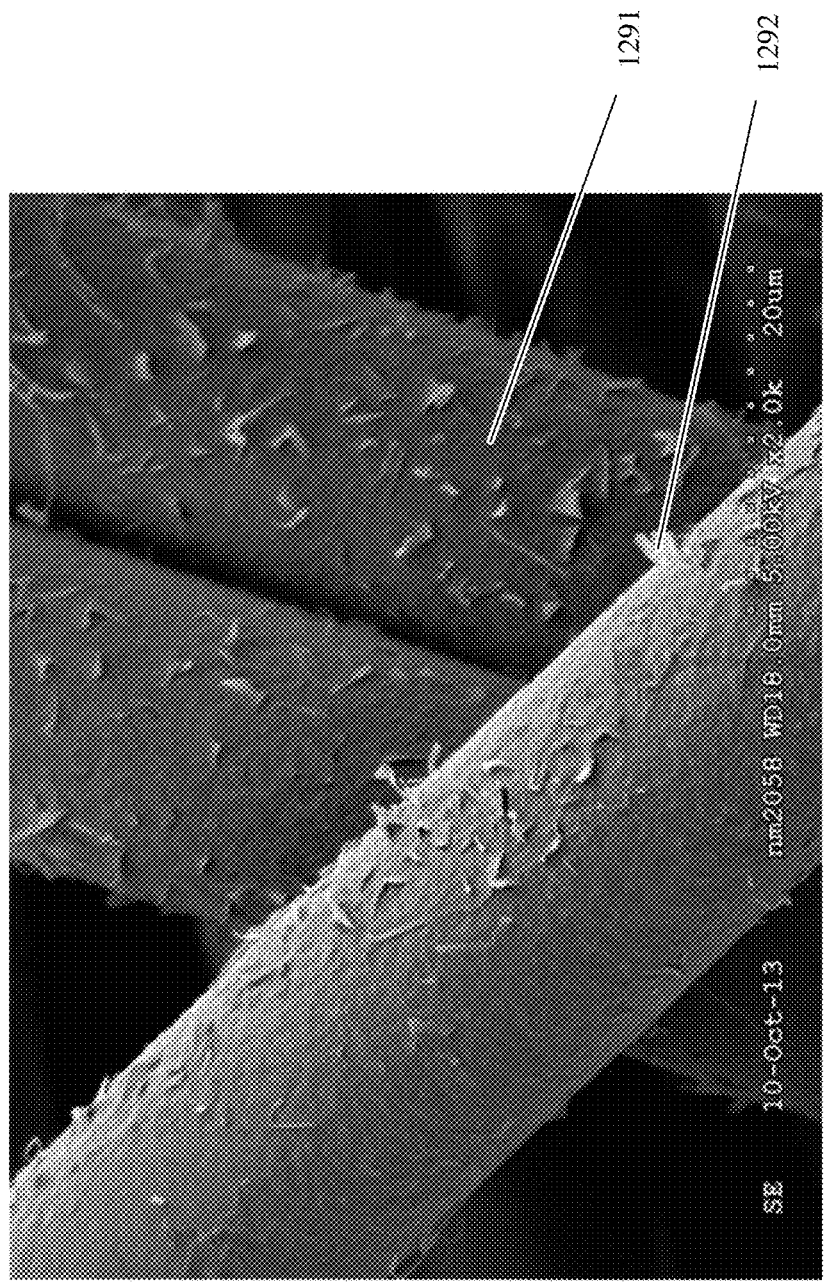
FIG. 12 is an SEM photo showing another nonwoven fiber with additive that has bloomed on the surface of the fiber.

FIG. 12 is an SEM photo of a bi-component fiber 1291 of polyethylene and polypropylene arranged in 30/70 sheath/core configuration—the polyethylene being the sheath. The additive (glycerol tristearate) was added to the fibers as a master batch (17% of Techmer PPM 17000 High Load Hydrophobic). The master batch comprised about 60 percent by weight polyethylene and about 40 percent by weight glycerol tristearate. The sheath of the fiber comprised 17 percent by weight master batch and 83 percent by weight polyethylene. As shown, the fiber 1291 comprises a plurality of fibrils 1292 extending therefrom.

Figure 13:
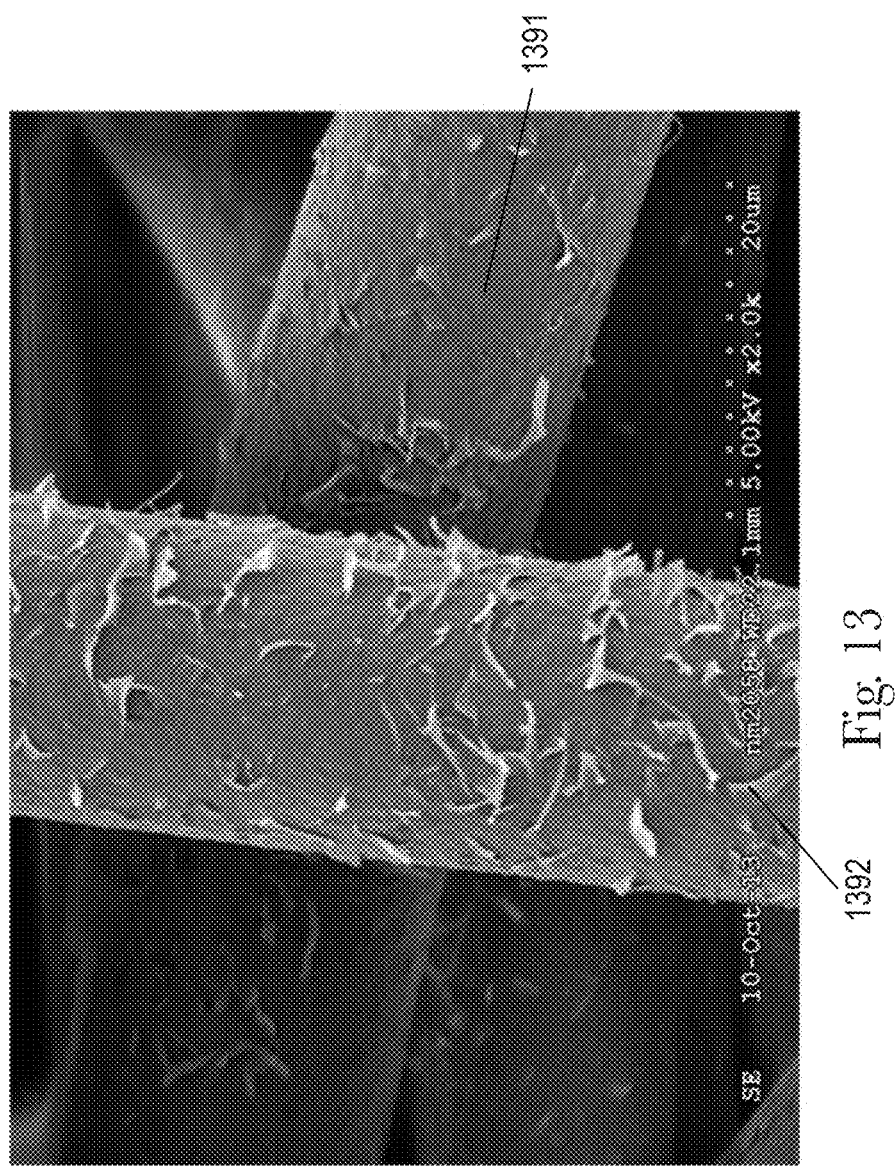
FIG. 13 is an SEM photo showing another nonwoven fiber with additive that has bloomed on the surface of the fiber.

FIG. 13 is an SEM photo of a bi-component fiber 1391 of polyethylene and polypropylene arranged in 30/70 sheath/core configuration—polyethylene being the sheath. The additive (glycerol tristearate) was added to the fibers as a master batch. The master batch comprised about 60 percent by weight polyethylene and about 40 percent by weight glycerol tristearate. The sheath of the fiber comprised 30 percent by weight master batch and 70 percent by weight polyethylene. As shown, the fiber 1391 comprises a plurality of fibrils 1392 extending therefrom.

Figure 14:
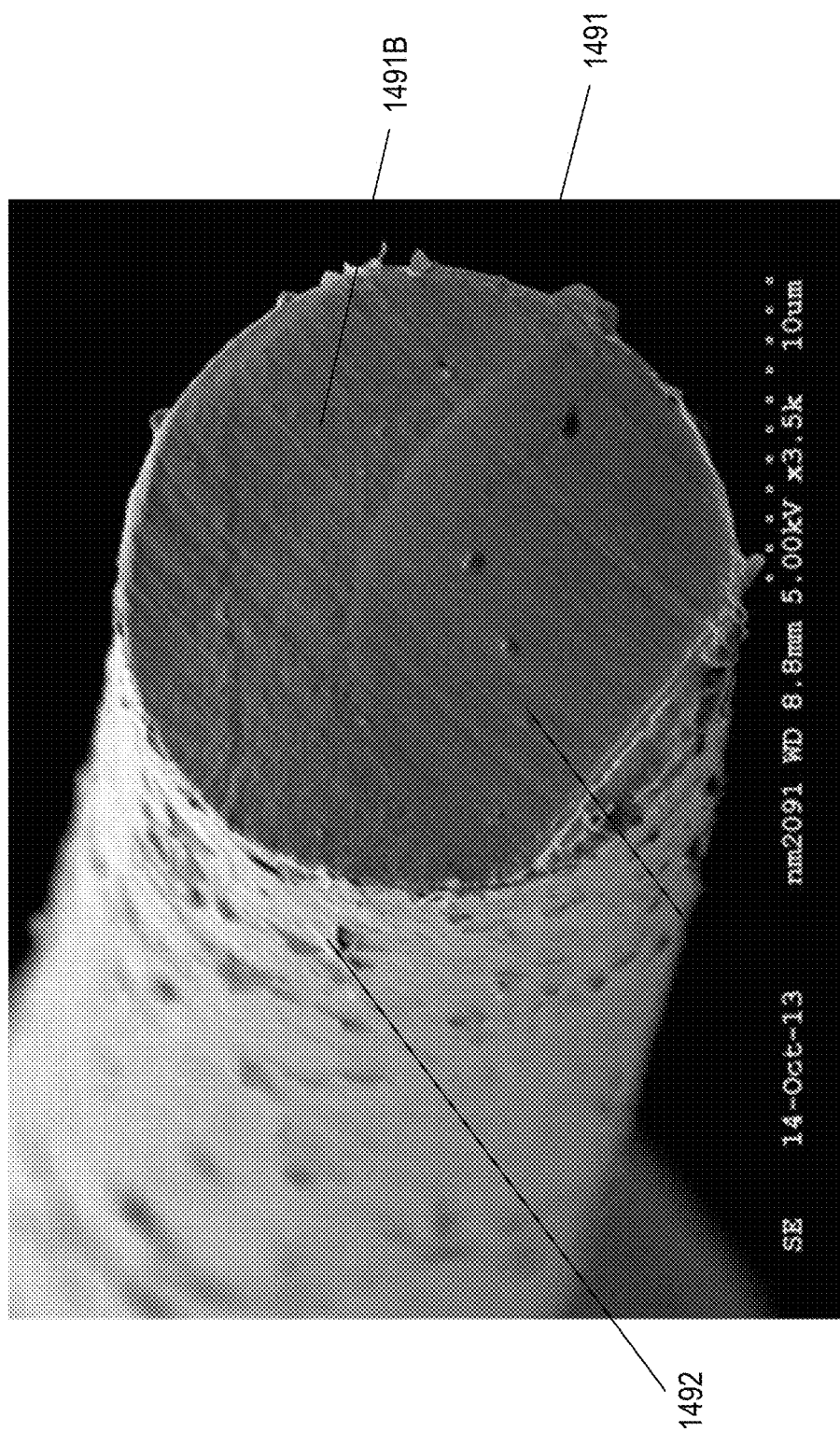
FIG. 14 is an SEM photo showing another nonwoven fiber with additive that has bloomed on the surface of the fiber.
Figure 15:
FIG. 15 is an SEM photo showing another nonwoven fiber with additive that has bloomed on the surface of the fiber.

FIGS. 14 and 15 demonstrate that the additive can be added variably with regard to differing components of a fiber. FIG. 14 is an SEM photo of a polypropylene/polyethylene bi-component fiber 1491 where the polypropylene and the polyethylene are configured side by side—polyethylene 1491A and polypropylene 1491B. The additive was added at varying levels as a master batch (Techmer PPM17000 High Load Hydrophobic)—10% master batch was added to the polypropylene component and 5% of the same master batch was added to the polyethylene component.

FIG. 15 is an SEM photo of a polypropylene/polyethylene bi-component fiber 1591 where the polypropylene and polyethylene are configured side by side—polypropylene 1591A and polyethylene 1591B comprising fibrils 1592. The additive was added at varying levels as a master batch (Techmer PPM17000 High Load Hydrophobic)—16% master batch was added to the polypropylene component and 8% master batch was added to the polyethylene component. In some instances, the additive may bloom more on one side of the bi-component fiber 1591 than the other.

Figure 16:
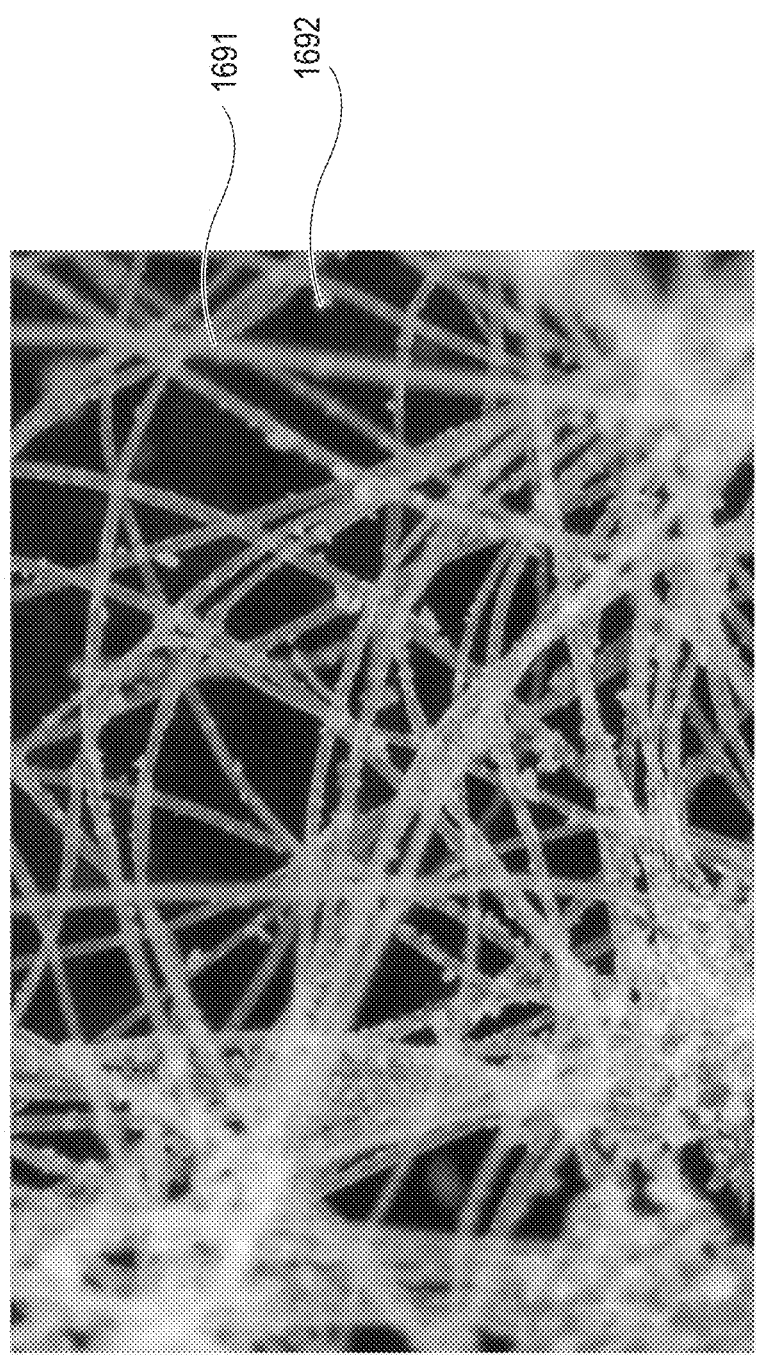
FIG. 16 is an SEM photo showing other nonwoven fibers with additive that has been applied to the fibers.

FIG. 16 is an SEM photo showing a plurality of fibers of a nonwoven where the additive has been applied post fiber production. As shown, the additive forms a plurality of droplets/particles 1692 on the surface of the fibers.

Figure 17:
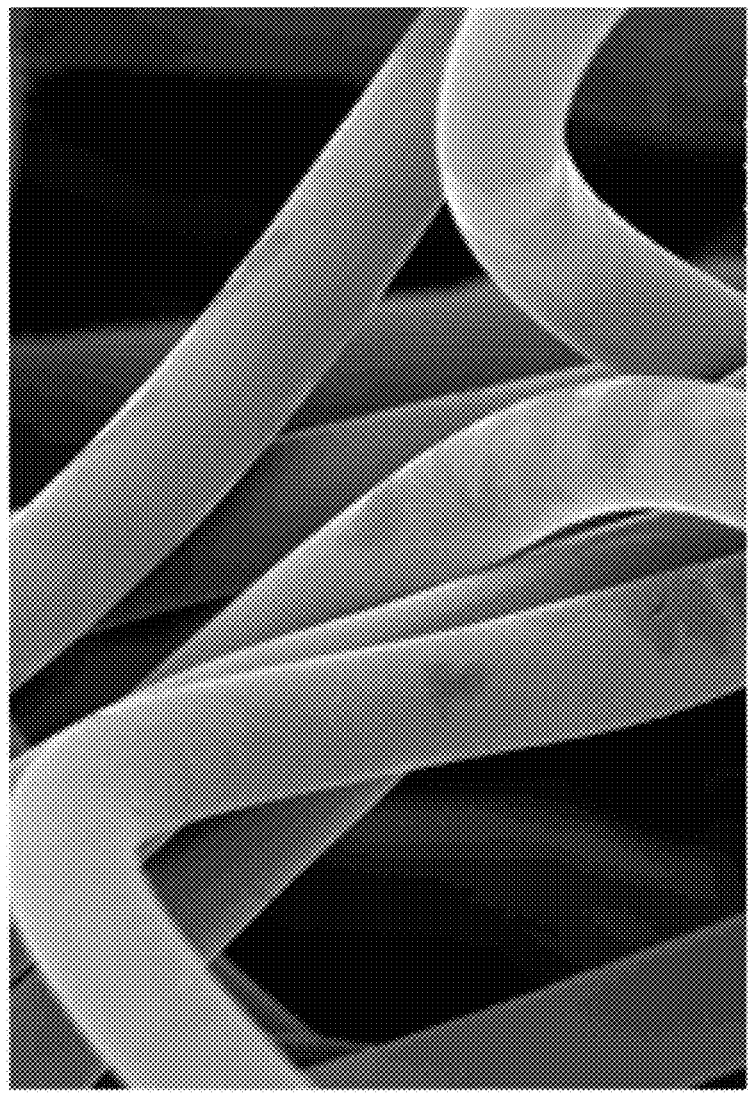
FIG. 17 is an SEM photo showing nonwoven fibers with additive that has formed a film on the surface of the fibers.
Figure 18:
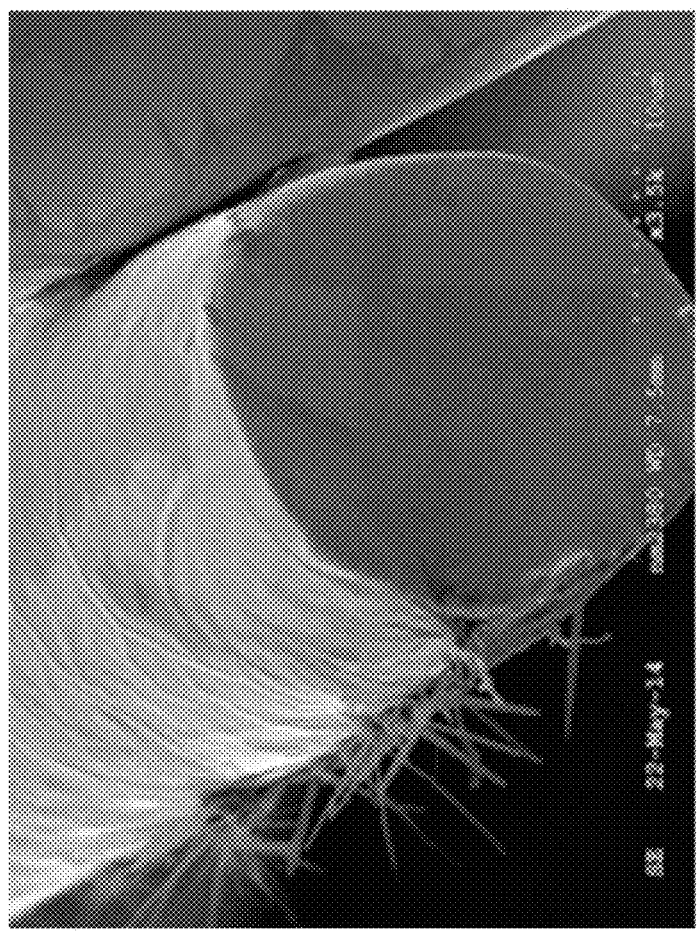
FIG. 18 is an SEM photo showing nonwoven fibers with additive that has formed a film and fibrils on the surface of the fibers.

FIGS. 17 and 18 are SEM photos showing fibers comprising a melt additive. In FIG. 17, the additive has bloomed to the surface of the fibers to form a film, and in FIG. 18, the additive has bloomed to the surface of the fiber to form a film/fibril combination. In FIG. 17, polypropylene fibers with 16 percent by weight master batch (Techmer PPM17000 High Load Hydrophobic) are shown.

In FIG. 18, the fibers are bi-component polypropylene/polyethylene fibers in a side by side configuration. The polypropylene comprises 16 percent by weight master batch (Techmer PPM17000 High Load Hydrophobic), and the polyethylene component comprises 8 percent by weight of the same master batch.

Figure 19A:
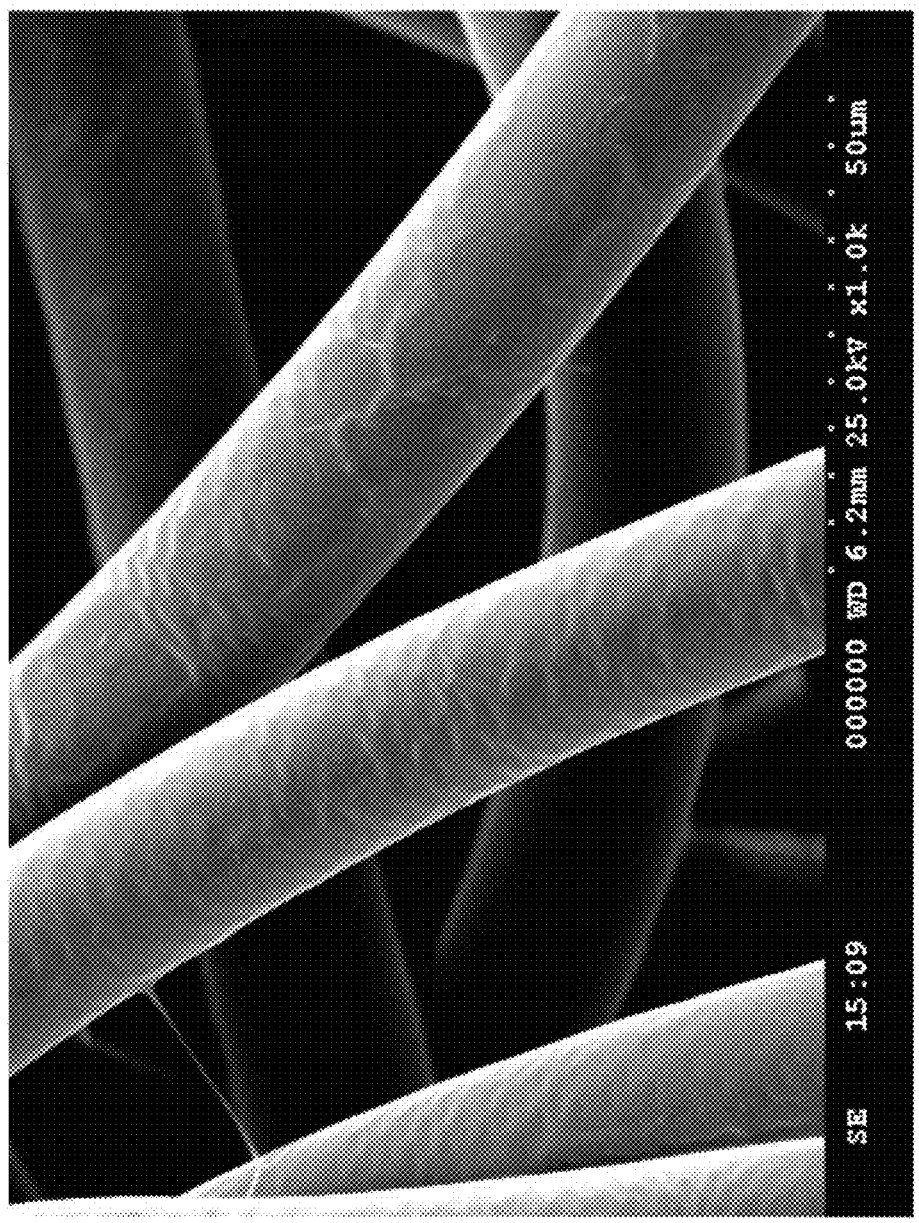
FIGS. 19A-19C are SEM photos showing crimped fiber nonwovens comprising melt additives.
Figure 19B:
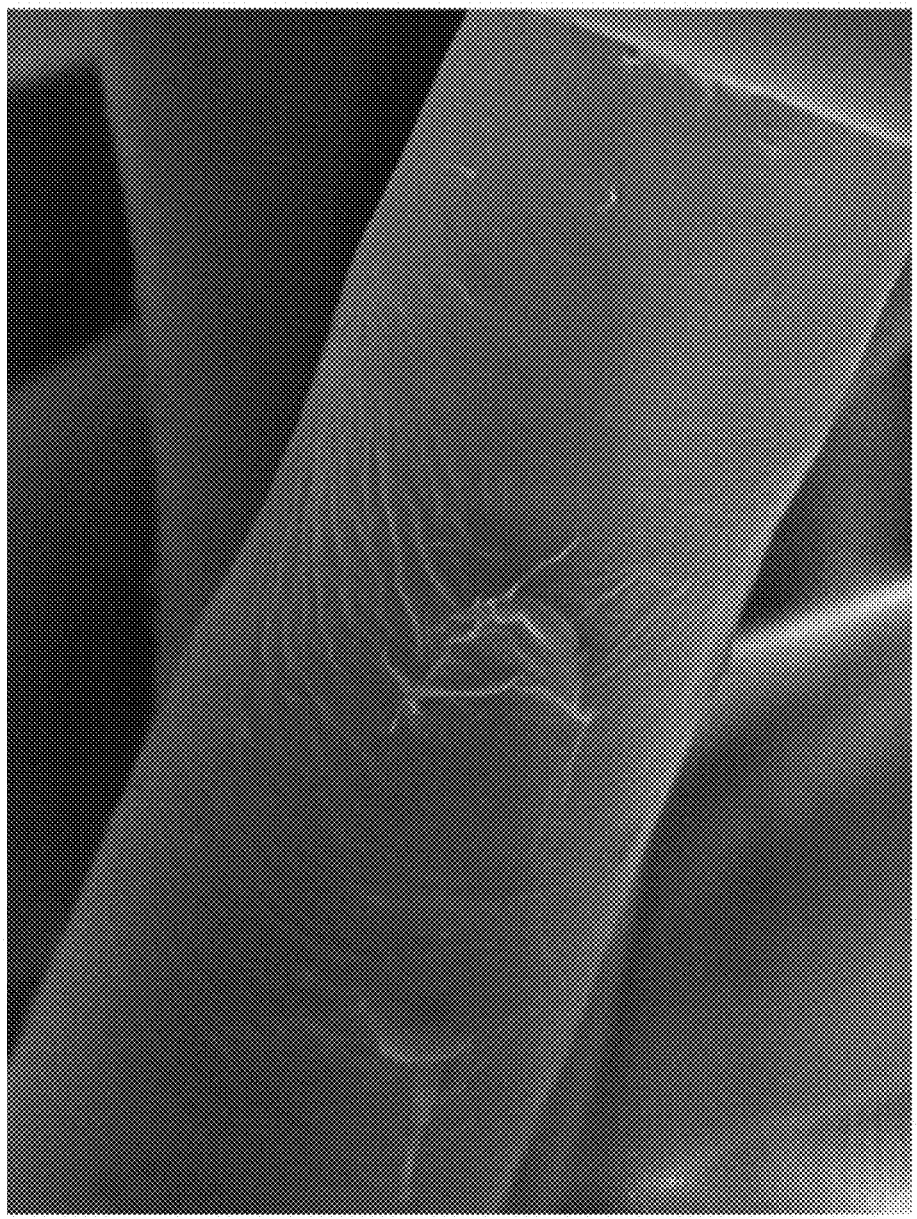
Figure 19C:
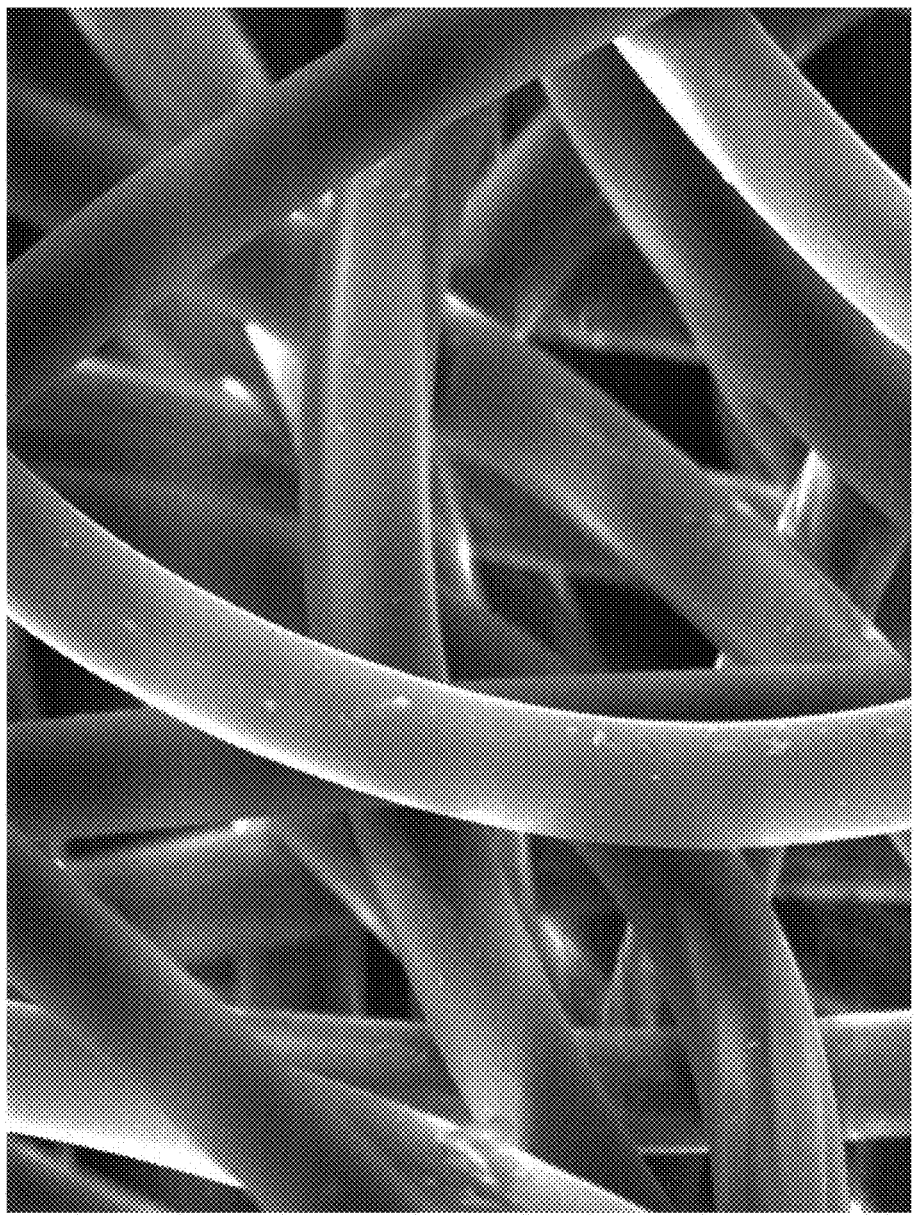

In FIGS. 19A-19C nonwoven layers comprising fibers with hydrophobic melt additive are shown; however, the melt additive did not present itself in the form of fibrils. In FIG. 19A, the fibers are 2.6 denier per filament and comprise 60/40 side/side polypropylene/polypropylene, using Lyondell Basell HP561R in the first component and Lyondell Basell HP552 R in the second component. Both components additionally comprise 16% Techmer PPM17000 High Load Hydrophobic masterbatch, and 1% of TiO$_2$ masterbatch (MBWhite009). In FIG. 19A, the hydrophobic melt additive creates a wrinkled texture on the fiber surface.

In FIGS. 19B and 19C, a nonwoven layer comprising fibers having a denier of 2.0 and comprise 60/40 side/side polypropylene/polypropylene, using Lyondell Basell HP561R in the first component and Lyondell Basell HP552 R in the second component. Both components additionally comprise 10% Techmer PPM17000 High Load Hydrophobic masterbatch, and 1% of TiO$_2$ masterbatch (MBWhite009). As shown, the lower amount of hydrophobic melt additive does not provide the same surface structure as that depicted with regard to FIG. 19A. But some wrinkled structures are seen in FIG. 19B.

Figure 20A:
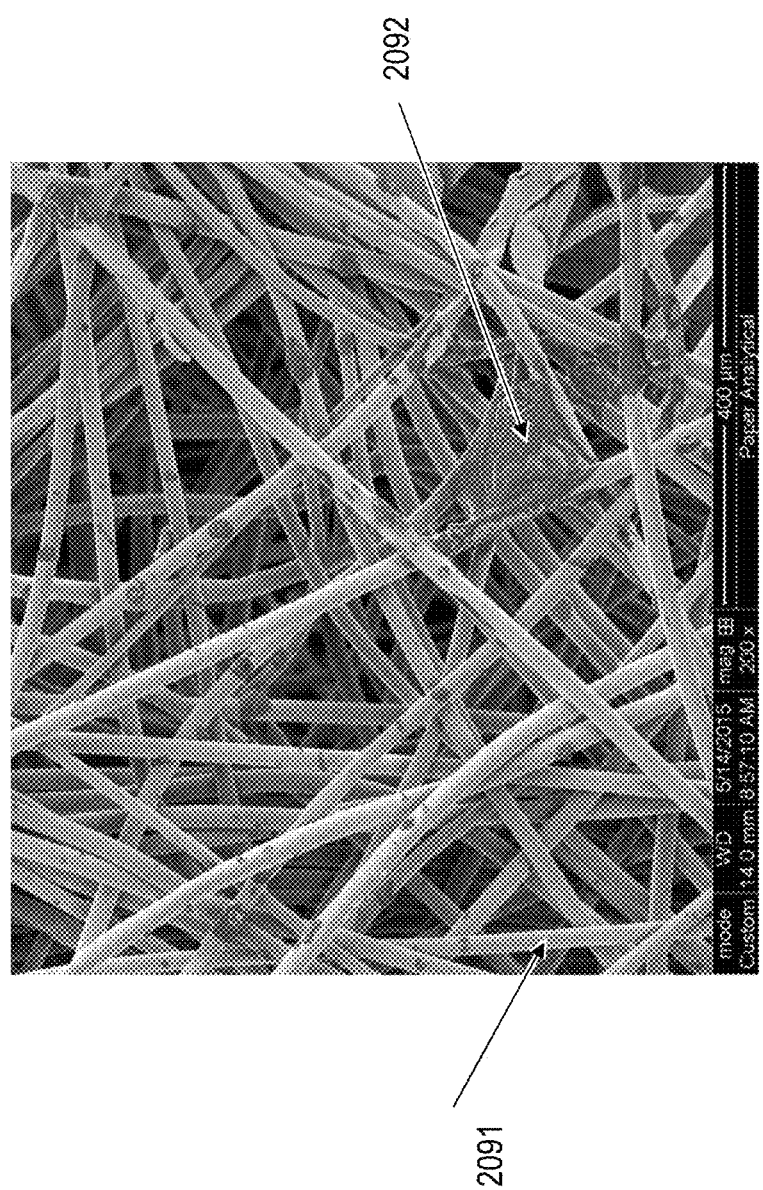
FIGS. 20A-20C are SEM photos showing a sprayed on topical hydrophobic treatment at varying basis weights.
Figure 20B:
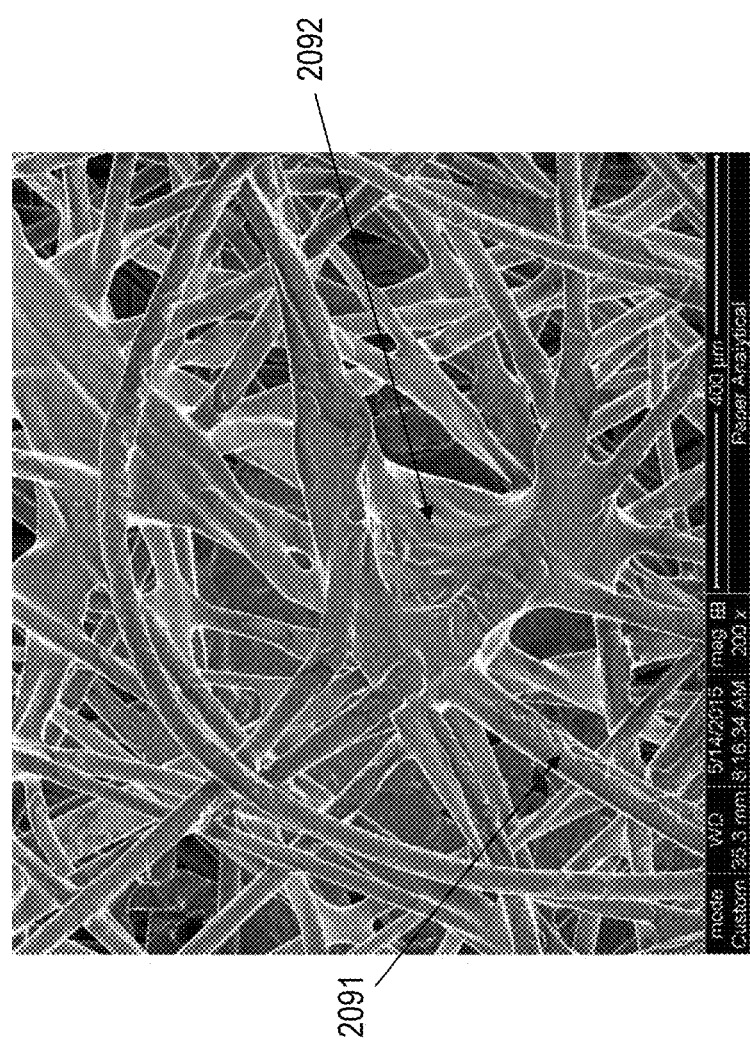
Figure 20C:
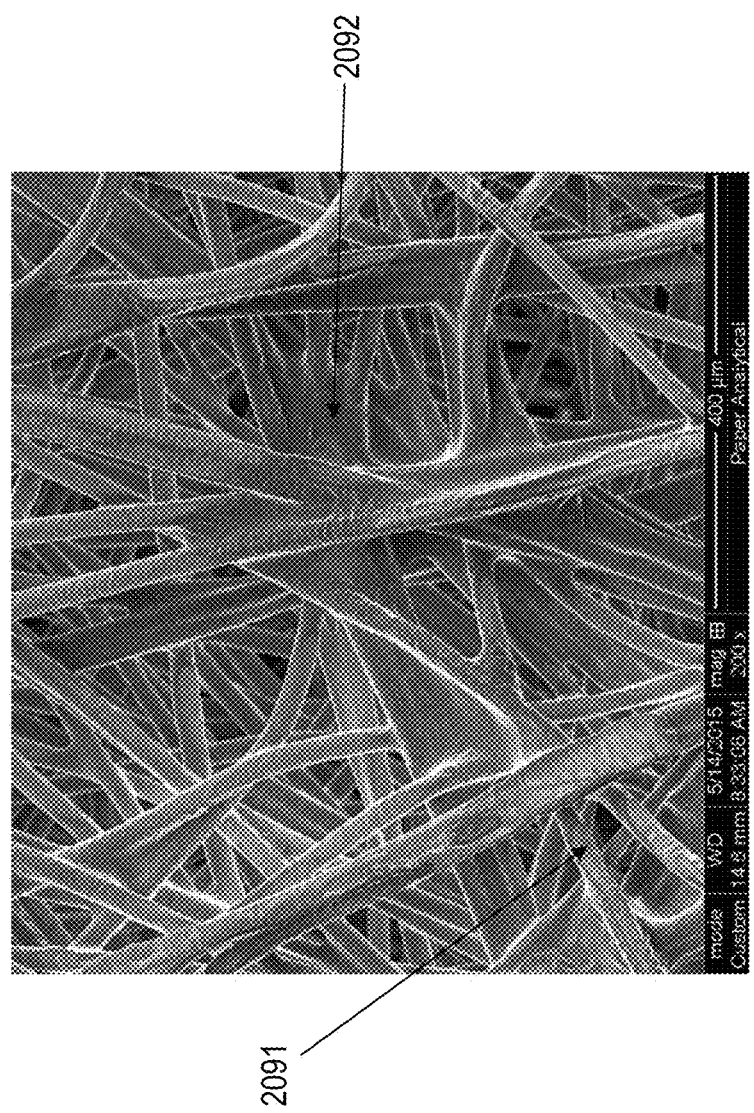

FIGS. 20A-20C show examples of nonwoven webs comprising a spray on hydrophobic additive. For example, as shown in FIG. 20A, fibers 2091 of a nonwoven web were spray coated with glycerol tristearate 2092 at a basis weight of about 5 gsm. It is worth noting that the spray application appears to leave large portions of the fibers 2091 uncovered. Regarding FIG. 20B, the fibers 2091 were spray coated with glycerol tristearate 2092 at a basis weight of about 10 gsm. Regarding FIG. 20C, the fibers 2091 were spray coated with glycerol tristearate 2092 at a basis weight of about 20 gsm.

Laminates Comprising Examples.

Four total laminates were made, two of the laminates comprised examples above. Rewet data was gathered for the laminates post a cumulative liquid insult of about 21 ml of artificial menstrual fluid.

Laminate 1 was a 25 gsm spubond bi-component fiber nonwoven. The filaments were 2.5 denier per filament and comprised a 50/50 sheath core configuration of polyethylene/polypropylene. The lower layer was as described with regard to Laminate 2.

Laminate 2 comprised an upper layer which was described with regard to FIG. 12 and a lower layer comprising bi-component fibers spunbond with topical hydrophilic surfactant. The basis weight of the lower layer was 28 gsm, 2.8 denier per filament, 50/50 sheath/core, polyethylene/polypropylene. The web was coated with 0.4% by weight Silastol PHP26 surfactant made by Schill & Seilacher, Germany.

Laminate 3 is the same as Laminate 4 but without the melt additive in the upper layer. Laminate 4 comprised an upper layer which was described with regard to FIGS. 19B and 19C and a lower layer comprising crimped fiber spunbond with topical hydrophilic surfactant. The lower layer comprised fibers having 2.6 denier per filament, 70/30 side/side, polypropylene/polypropylene, using Lyondell Basell HP561R in the first component and Lyondell Basell HP552 R in the second component. Both components additionally comprise 1% of TiO$_2$ masterbatch (MBWhite009). The lower layer was coated with 0.4% by weight Silastol PHP26 surfactant made by Schill & Seilacher, Germany.

Laminates 2 and 4 had lower rewet scores than laminates 1 and 3. Because Laminates 2 and 4 comprised an upper nonwoven layer which comprised a hydrophobic melt additive, it is believed that the hydrophobic melt additive can provide laminates with a rewet benefit.

Tests

HLB (Hydrophilic/Lipophilic Balance)

The term "HLB" or "HLB value" of a surfactant refers to the Hydrophilic-Lipophilic Balance and is a measure of the degree to which it is hydrophilic or lipophilic, determined by calculating values for the different regions of the molecule. For nonionic surfactants the HLB=20*Mb/M, where M is the molecular mass of the whole molecule and Mb is the molecular mass of the hydrophilic portion of the Molecule. An HLB value of 0 corresponds to a completely lipidphilic/hydrophobic molecule, and a value of 20 corresponds to a completely hydrophilic/lipidphobic molecule. The above represents the Griffin method of HLB calculation which is well known in the art.

Basis Weight Test

A 9.00 cm$^2$ large piece of nonwoven substrate, i.e., 1.0 cm wide by 9.0 cm long, is used. The sample may be cut out of a consumer product, such as a wipe or an absorbent article or a packaging material therefor. The sample needs to be dry and free from other materials like glue or dust. Samples are conditioned at 23° Celsius (±2° C.) and at a relative humidity of about 50% (±5%) for 2 hours to reach equilibrium. The weight of the cut nonwoven substrate is measured on a scale with accuracy to 0.0001 g. The resulting mass is divided by the specimen area to give a result in g/m$^2$ (gsm). Repeat the same procedure for at least 20 specimens from 20 identical consumer products or packaging materials therefor. If the consumer product or packaging materials therefor are large enough, more than one specimen can be obtained from each. An example of a sample is a portion of a topsheet of an absorbent article. If the local basis weight variation test is done, those same samples and data are used for calculating and reporting the average basis weight.

Fiber Diameter and Denier Test

The diameter of fibers in a sample of a nonwoven substrate is determined by using a Scanning Electron Microscope (SEM) and image analysis software. A magnification of 500 to 10,000 times is chosen such that the fibers are suitably enlarged for measurement. The samples are sputtered with gold or a palladium compound to avoid electric charging and vibrations of the fibers in the electron beam. A manual procedure for determining the fiber diameters is used. Using a mouse and a cursor tool, the edge of a randomly selected fiber is sought and then measured across its width (i.e., perpendicular to fiber direction at that point) to the other edge of the fiber. For non-circular fibers, the area of the cross-section is measured using the image analysis software. The effective diameter is then calculated by calculating the diameter as if the found area was that of a circle. A scaled and calibrated image analysis tool provides the scaling to get actual reading in micrometers (μm). Several fibers are thus randomly selected across the sample of the nonwoven substrate using the SEM. At least two specimens from the nonwoven substrate are cut and tested in this manner. Altogether, at least 100 such measurements are made and then all data is recorded for statistical analysis. The recorded data is used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

Fiber Diameter in denier=Cross-sectional area (in m2)*density (in kg/m3)*9000 m*1000 g/kg.

For round fibers, the cross-sectional area is defined by the equation:

$A=\pi*(D/2)^2$.

The density for polypropylene, for example, may be taken as 910 kg/m3.

Given the fiber diameter in denier, the physical circular fiber diameter in meters (or micrometers) is calculated from these relationships and vice versa. We denote the measured diameter (in microns) of an individual circular fiber as D.

In case the fibers have non-circular cross-sections, the measurement of the fiber diameter is determined as and set equal to the hydraulic diameter, as discussed above.

Specific Surface Area

The specific surface area of the nonwoven substrates of the present disclosure is determined by Krypton gas adsorption using a Micromeritic ASAP 2420 or equivalent instrument, using the continuous saturation vapor pressure ($P_o$) method (according to ASTM D-6556-10), and following the principles and calculations of Brunauer, Emmett, and Teller, with a Kr-BET gas adsorption technique including automatic degas and thermal correction. Note that the specimens should not be degassed at 300 degrees Celsius as the method recommends, but instead should be degassed at room temperature. The specific surface area should be reported in m$^2$/g.

Obtaining Samples of Nonwoven Substrates

Each surface area measurement is taken from a specimen totaling 1 g of the nonwoven substrate of the present disclosure. In order to achieve 1 g of material, multiple specimens may be taken from one or more absorbent articles, one or more packages, or one or more wipes, depending on whether absorbent articles, packages, or wipes are being tested. Wet wipe specimens will be dried at 40 degrees C. for two hours or until liquid does not leak out of the specimen under light pressure. The specimens are cut from the absorbent articles, packages, or wipes (depending on whether absorbent articles, packages, or wipes are being tested) in areas free of, or substantially free of, adhesives using scissors. An ultraviolet fluorescence analysis cabinet is then used on the specimens to detect the presence of adhesives, as the adhesives will fluoresce under this light. Other methods of detecting the presence of adhesives may also be used. Areas of the specimens showing the presence of adhesives are cut away from the specimens, such that the specimens are free of the adhesives. The specimens may now be tested using the specific surface areafibrils method above.

Fibril Length Measurement Test

1) Using a software program such as Image J software, measure the number of pixels within the length of the legend on an SEM image of a nonwoven substrate using a straight line (i.e., a line with a length and no thickness). Record the length of the line and the number of microns that the legend corresponds to.
2) Pick a fibril and measure its length from its free end to the end originating out of the fiber as best visualized. Record the length of the line.
3) Divide this length by the length of the legend in pixels and then multiply by the length of the legend in microns to get the length of the fibril in microns.

If the fibrils are long and curly, then the length of such fibrils is taken in linear increments.

Fibril Width Measurement Test

1) Using a software program such as Image J software, measure the number of pixels within the length of the legend on an SEM image of a nonwoven substrate using a straight line (i.e., a line with a length and no thickness). Record the length of the line and the number of microns that the legend corresponds to.

2) Pick a fibril and measure its width as best visualized. Record the length of the line.

3) Divide this width by the length of the legend in pixels and then multiply by the length of the legend in microns to get the width of the fibril in microns.

If the fibrils are curved, then the width of such fibrils is taken in linear increments.

Fibril Thickness Measurement Test

1) Using a software program such as Image J software, measure the number of pixels within the length of the legend on an SEM image of a nonwoven substrate using a straight line (i.e., a line with a length and no thickness). Record the length of the line and the number of microns that the legend corresponds to.

2) Pick a fibril and measure its thickness as best visualized. Record the length of the line.

3) Divide this thickness by the length of the legend in pixels and then multiply by the length of the legend in microns to get the thickness of the fibril in microns.

If the fibril has variable thickness across its width, then the thickness of such fibril is taken as numeric average of measurements across its width.

Fibril Separation Measurement Test

1) Using a software program such as Image J software, measure the number of pixels within the length of the legend on an SEM image of a nonwoven substrate using a straight line (i.e., a line with a length and no thickness). Record the length of the line and the number of microns that the legend corresponds to.

2) Pick a fibril and measure its distance from one of its nearest neighbor as best visualized. Record the length of the line.

3) Divide this thickness by the length of the legend in pixels and then multiply by the length of the legend in microns to get the thickness of the fibril in microns.

Repeat steps (2) and (3) above to measure distance of the fibril from the rest of its nearest neighbors. Take numeric average of the measured distances to calculate average separation distance of the fibrils.

Mass-Average Diameter

The mass-average diameter of fibers is calculated as follows:

mass average diameter, $$d_{mass} = \frac{\sum_{i=1}^{n}(m_i \cdot d_i)}{\sum_{i=1}^{n} m_i} = \frac{\sum_{i=1}^{n}(\rho \cdot V_i \cdot d_i)}{\sum_{i=1}^{n}(\rho \cdot V_i)} = \frac{\sum_{i=1}^{n}\left(\rho \cdot \frac{\pi d_i^2 \cdot \partial x}{4} \cdot d_i\right)}{\sum_{i=1}^{n}\left(\rho \cdot \frac{\pi d_i^2 \cdot \partial x}{4}\right)} = \frac{\sum_{i=1}^{n} d_i^3}{\sum_{i=1}^{n} d_i^2}$$

where fibers in the sample are assumed to be circular/cylindrical, $d_i$=measured diameter of the $i^{th}$ fiber in the sample, $\partial x$=infinitesimal longitudinal section of fiber where its diameter is measured, same for all the fibers in the sample, $m_i$=mass of the $i^{th}$ fiber in the sample, n=number of fibers whose diameter is measured in the sample $\rho$=density of fibers in the sample, same for all the fibers in the sample $V_i$=volume of the $i^{th}$ fiber in the sample.

The mass-average fiber diameter should be reported in µm.

Gravimetric Weight Loss Test

The Gravimetric Weight Loss Test is used to determine the amount of lipid ester (e.g., GTS) in a nonwoven substrate of the present disclosure. One or more samples of the nonwoven substrate are placed, with the narrowest sample dimension no greater than 1 mm, into acetone at a ratio of 1 g nonwoven substrate sample per 100 g of acetone using a refluxing flask system. First, the sample is weighed before being placed into the reflux flask, and then the mixture of the sample and the acetone is heated to 60° C. for 20 hours. The sample is then removed and air dried for 60 minutes and a final weight of the sample is determined. The equation for calculating the weight percent lipid ester in the sample is:

weight % lipid ester=([initial mass of the sample−final mass of the sample]/[initial mass of the sample])×100%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web for use in an absorbent article, the nonwoven web comprising:

a first spunlace, carded nonwoven layer consisting essentially of a first plurality of fibers, wherein the first plurality of fibers consists essentially of a thermoplastic polymer and a melt additive consisting essentially of a glycerol fatty acid ester derived from a C8 to C30 fatty acid, the glycerol fatty acid ester having a HLB value between 0 and 4, a generally planar first surface and a generally planar second surface opposed to the first surface, wherein the first spunlace, carded nonwoven layer comprises a plurality of apertures and the additive is disposed, at least in part, on at least a portion of the first plurality of fibers; and wherein the additive forms a plurality of droplets or fibrils on the surface of the first plurality of fibers, wherein the fibrils or droplets have a color which is different than that of the first plurality of fibers, and a second spunlace, carded nonwoven layer comprising a second plurality of fibers, a generally planar first surface and a generally planar second surface opposed to the first surface, wherein the second spunlace, carded nonwoven layer is attached to the first nonwoven layer such that at least a portion of the second plurality of fibers are in liquid communication with the first spunlace, carded nonwoven layer, wherein the first spunlace, carded nonwoven layer is hydrophobic and the second spunlace, carded nonwoven layer is hydrophilic.

2. The nonwoven web of claim 1, wherein the first plurality of fibers comprises polypropylene or polyethylene and the second plurality of fibers comprises rayon or cotton.

3. The nonwoven web of claim 1, wherein the first plurality of fibers comprises monocomponent fibers.

4. The nonwoven web of claim 1, wherein the first plurality of fibers comprises bicomponent fibers.

5. The nonwoven web of claim 4, wherein the bi-component fibers comprise a first polypropylene and a second polypropylene arranged in a side by side configuration and are crimped.

6. The nonwoven web of claim 5, wherein the additive is provided at different levels in each component.

7. The nonwoven web of claim 1, wherein the first plurality of fibers comprises bi-component fibers comprising polyethylene and polypropylene arranged in a sheath/core configuration.

8. The nonwoven web of claim 1, wherein the additive is present in the first nonwoven layer at from between about 1 percent to about 15 percent by weight.

9. The nonwoven web of claim 1, wherein the additive has a melting point in the range of about 40 degrees C. to about 80 degrees C.

10. The nonwoven web of claim 9, wherein the additive comprises glycerol tristearate.

* * * * *